US012594397B2

(12) United States Patent
Hogg et al.

(10) Patent No.: US 12,594,397 B2
(45) Date of Patent: Apr. 7, 2026

(54) VENT SYSTEM FOR PATIENT INTERFACE

(71) Applicant: RESMED PTY LTD, Bella Vista (AU)

(72) Inventors: Michael Christopher Hogg, Sydney (AU); Luke Andrew Stanislas, Sydney (AU)

(73) Assignee: RESMED PTY LTD, Bella Vista (AU)

( * ) Notice: Subject to any disclaimer, the term of this patent is extended or adjusted under 35 U.S.C. 154(b) by 1187 days.

(21) Appl. No.: 17/433,835

(22) PCT Filed: Feb. 26, 2020

(86) PCT No.: PCT/AU2020/050167
§ 371 (c)(1),
(2) Date: Aug. 25, 2021

(87) PCT Pub. No.: WO2020/172708
PCT Pub. Date: Sep. 3, 2020

(65) Prior Publication Data
US 2022/0143358 A1     May 12, 2022

Related U.S. Application Data

(60) Provisional application No. 62/810,640, filed on Feb. 26, 2019.

(51) Int. Cl.
*A61M 16/20*     (2006.01)
*A61M 16/06*     (2006.01)

(52) U.S. Cl.
CPC ...... *A61M 16/208* (2013.01); *A61M 16/0666* (2013.01); *A61M 16/0683* (2013.01); *A61M 2202/0225* (2013.01); *A61M 2205/42* (2013.01)

(58) Field of Classification Search
CPC ............ A61M 16/0666; A61M 16/208; A61M 16/0683; A61M 16/0816; A61M 16/06; A61M 16/16; A61M 2205/42
See application file for complete search history.

(56) References Cited

U.S. PATENT DOCUMENTS 2,944,547 A     7/1960   Ziherl et al.
3,435,839 A *   4/1969   Elder ................. A61M 16/208
                                                                    128/205.24
(Continued)

FOREIGN PATENT DOCUMENTS

CN         101098727 A     1/2008
CN         101516300 A     8/2009
(Continued)

OTHER PUBLICATIONS

Extended European Search Report dated May 11, 2022 issued in European Application No. 20762807.4 (7 pages).
(Continued)

*Primary Examiner* — Colin W Stuart
*Assistant Examiner* — Douglas Y Sul
(74) *Attorney, Agent, or Firm* — NIXON & VANDERHYE, P.C.

(57)     ABSTRACT

A vent structure may include a vent housing comprising an inlet, an outlet, at least one exhaust gas orifice, and a membrane having a first end and a second end spaced apart, the membrane having a moveable portion between the first end and the second end. The moveable portion may be spaced radially from a membrane-facing surface inside of the vent housing to form an exhaust gas flow passage therebetween to allow exhaust gas to flow from the pressurised volume through the exhaust gas flow passage to atmosphere via the exhaust gas orifice. The moveable portion may be elastically deformable and configured to move radially relative to the membrane-facing surface in response to pressure differences between an interior side of the membrane and an exterior side of the membrane to change a cross-sectional area of the exhaust gas flow passage and regulate the vent flow of gas.

46 Claims, 33 Drawing Sheets

(56) References Cited

U.S. PATENT DOCUMENTS

| | | | | |
|---|---|---|---|---|
| 3,527,242 A | * | 9/1970 | Ansite | F16K 15/148 |
| | | | | 137/859 |
| 4,457,330 A | * | 7/1984 | Fields | F16K 15/141 |
| | | | | 137/107 |
| 4,458,679 A | | 7/1984 | Ward | |
| 4,782,832 A | | 11/1988 | Trimble et al. | |
| 4,944,310 A | | 7/1990 | Sullivan | |
| 4,997,217 A | | 3/1991 | Kunze | |
| 5,002,050 A | * | 3/1991 | McGinnis | A61M 16/208 |
| | | | | 128/205.24 |
| 5,271,601 A | | 12/1993 | Bonzer et al. | |
| 5,685,296 A | | 11/1997 | Zdrojkowski et al. | |
| 5,687,715 A | | 11/1997 | Landis | |
| 5,762,382 A | | 6/1998 | Pernetti et al. | |
| 5,896,857 A | | 4/1999 | Hely et al. | |
| 5,937,851 A | * | 8/1999 | Serowski | A61M 16/0825 |
| | | | | 128/205.25 |
| 5,979,444 A | | 11/1999 | Sherrod | |
| 6,189,532 B1 | | 2/2001 | Hely et al. | |
| 6,427,692 B1 | | 8/2002 | Höglund | |
| 6,532,959 B1 | | 3/2003 | Berthon-Jones | |
| 6,581,594 B1 | | 6/2003 | Drew et al. | |
| 6,584,977 B1 | * | 7/2003 | Serowski | A61M 16/08 |
| | | | | 128/207.12 |
| 6,662,803 B2 | | 12/2003 | Gradon et al. | |
| 7,089,939 B2 | | 8/2006 | Waker et al. | |
| 7,096,864 B1 | | 8/2006 | Mayer et al. | |
| 7,134,434 B2 | | 11/2006 | Truitt et al. | |
| 7,302,950 B2 | | 12/2007 | Berthon-Jones et al. | |
| 7,559,326 B2 | | 7/2009 | Smith et al. | |
| 7,866,944 B2 | | 1/2011 | Kenyon et al. | |
| 7,987,847 B2 | | 8/2011 | Wickham | |
| 7,987,851 B2 | | 8/2011 | Blom | |
| 8,353,293 B1 | | 1/2013 | Fuhrman | |
| 8,365,731 B2 | | 2/2013 | Ho et al. | |
| 8,439,035 B2 | | 5/2013 | Dantanarayana et al. | |
| 8,496,004 B2 | | 7/2013 | Lang et al. | |
| 8,544,465 B2 | | 10/2013 | Smith et al. | |
| 8,573,208 B2 | | 11/2013 | Ho | |
| 8,636,479 B2 | | 1/2014 | Kenyon et al. | |
| 8,638,014 B2 | | 1/2014 | Sears et al. | |
| 8,733,349 B2 | | 5/2014 | Bath et al. | |
| 9,808,594 B2 | | 11/2017 | Dantanarayana et al. | |
| 10,220,179 B2 | | 3/2019 | Dantanarayana et al. | |
| 10,265,496 B2 | | 4/2019 | Bugamelli et al. | |
| 2003/0005931 A1 | | 1/2003 | Jaffre et al. | |
| 2008/0142013 A1 | | 6/2008 | Hallett et al. | |
| 2009/0032022 A1 | | 2/2009 | Ho et al. | |
| 2009/0044808 A1 | | 2/2009 | Guney et al. | |
| 2009/0050156 A1 | | 2/2009 | Ng et al. | |
| 2009/0120434 A1 | | 5/2009 | Smith et al. | |
| 2009/0133694 A1 | | 5/2009 | Solci et al. | |
| 2010/0000534 A1 | | 1/2010 | Kooij et al. | |
| 2010/0083969 A1 | | 4/2010 | Crumblin et al. | |
| 2010/0282262 A1 | | 11/2010 | Boussignac | |
| 2011/0011397 A1 | * | 1/2011 | Ziv | A61M 16/06 |
| | | | | 128/207.18 |
| 2011/0067709 A1 | | 3/2011 | Doshi et al. | |
| 2012/0091381 A1 | | 4/2012 | Kern et al. | |
| 2012/0325205 A1 | | 12/2012 | Allum et al. | |
| 2012/0325218 A1 | | 12/2012 | Brambilla et al. | |
| 2013/0184602 A1 | | 7/2013 | Brambilla | |
| 2013/0213401 A1 | | 8/2013 | Haibach | |
| 2015/0114504 A1 | | 4/2015 | Cecka et al. | |
| 2015/0136137 A1 | | 5/2015 | Koninklijke et al. | |
| 2016/0051792 A1 | | 2/2016 | Hallet et al. | |
| 2016/0220781 A1 | * | 8/2016 | Arrowsmith | A61M 16/20 |
| 2017/0087329 A1 | * | 3/2017 | Huddart | A61M 16/209 |
| 2017/0259022 A1 | * | 9/2017 | Wong | A61M 16/0616 |
| 2017/0281898 A1 | * | 10/2017 | Dantanarayana | |
| | | | | A61M 16/0825 |
| 2018/0185607 A1 | | 7/2018 | Holley et al. | |
| 2018/0344953 A1 | | 12/2018 | Cegla | |

FOREIGN PATENT DOCUMENTS

| | | | |
|---|---|---|---|
| CN | 202951092 U | 5/2013 | |
| CN | 103974735 A | 8/2014 | |
| CN | 105148375 A | 12/2015 | |
| CN | 107921229 A | 4/2018 | |
| CN | 108025154 A | 5/2018 | |
| CN | 108136150 A | 6/2018 | |
| EP | 1027905 A2 | 8/2000 | |
| EP | 3320941 A1 | 5/2018 | |
| GB | 2500061 A1 | 9/2013 | |
| JP | 2004-522487 | 7/2004 | |
| JP | 2008-540056 | 11/2008 | |
| JP | 2010-535078 A | 11/2010 | |
| JP | 2015-516261 A | 6/2015 | |
| WO | WO 98/004310 A1 | 2/1998 | |
| WO | WO 98/034665 A1 | 8/1998 | |
| WO | 00/38772 | 7/2000 | |
| WO | WO 2000/078381 A1 | 12/2000 | |
| WO | 2002/051486 A1 | 7/2002 | |
| WO | WO 2004/073778 A1 | 9/2004 | |
| WO | 2005/063326 | 7/2005 | |
| WO | WO 2005/063328 A1 | 7/2005 | |
| WO | WO 2006/074513 A1 | 7/2006 | |
| WO | WO 2006/130903 A1 | 12/2006 | |
| WO | WO 2009/052560 A1 | 4/2009 | |
| WO | WO 2010/135785 A1 | 12/2010 | |
| WO | 2011/080604 | 7/2011 | |
| WO | WO 2012/171072 A1 | 12/2012 | |
| WO | WO 2013/020167 A1 | 2/2013 | |
| WO | 2014/097068 A1 | 6/2014 | |
| WO | 2014/138125 A1 | 9/2014 | |
| WO | 2014/205513 A1 | 12/2014 | |
| WO | 2015/013761 A1 | 2/2015 | |
| WO | 2015/041545 A1 | 3/2015 | |
| WO | 2015/052681 A1 | 4/2015 | |
| WO | 2015/177716 A1 | 11/2015 | |
| WO | 2016/041019 A1 | 3/2016 | |
| WO | 2016/141430 A1 | 9/2016 | |
| WO | 2017/049358 A1 | 3/2017 | |
| WO | 2018/033863 A1 | 2/2018 | |
| WO | 2018/052673 A1 | 3/2018 | |
| WO | 2018/053589 A1 | 3/2018 | |
| WO | 2018/126295 A1 | 7/2018 | |
| WO | 2019/180668 A1 | 9/2019 | |
| WO | 2019/280668 A1 | 9/2019 | |

OTHER PUBLICATIONS

Office Action dated Aug. 21, 2023 issued in Japanese Application No. 2022-549848 with English translation (13 pages).
Office Action dated Mar. 4, 2024 issued in Chinese Application No. 202080020546.7 with English translation (20 pages).
Examination Report dated Dec. 19, 2023 issued in New Zealand Application No. 785349 (4 pages).
Office Action dated Jan. 22, 2024 issued in Japanese Application No. 2021-549848 with English translation (4 pages).
Extended European Search Report dated Mar. 11, 2025 issued in European Application No. 25153920.1 (7 pages).
Office Action dated Feb. 13, 2025 issued in Mexican Application No. MX/a/2021/010249 with translation (11 pages).
International Search Report mailed Apr. 6, 2020 issued in International Application No. PCT/AU2020/050167 (6 pages).
Written Opinion of the International Searching Authority mailed Apr. 6, 2020 issued in issued in International Application No. PCT/AU2020/050167 (9 pages).
International Preliminary Report on Patentability mailed Jan. 21, 2021 issued in International Application No. PCT/AU2020/050167 (48 pages).
"*Respiratory Physiology*", by John B. West, Lippincott Wiliiams & Wilkins, 9th edition published 2012 (8 pages).
PCT/AU2017/051028.
PCT/Au2016/050893.
Office Action dated Dec. 13, 2020 issued in Chinese Application No. 201780067393.X with English translation (15 pages).

(56)     References Cited

OTHER PUBLICATIONS

Office Action dated Dec. 21, 2020 issued in Japanese Application No. 2019-515587 with English translation (13 pages).
Extended European Search Report dated Aug. 14, 2019 issued in European Application No. 17851991.4 (9 pages).
International Preliminary Report on Patentability mailed Mar. 26, 2019 issued in related International Application No. PCT/AU2017/051028 (6 pages).
International Search Report for PCT/AU2017/051028, mailed Dec. 19, 2017, 6 pages.
Written Opinion of the ISA for PCT/AU2017/051028, mailed Dec. 19, 2017, 5 pages.

* cited by examiner

Nasal cavity

Oral cavity

Larynx

Vocal folds

Oesophagus

Trachea

Bronchus

Lung

Heart

Diaphragm

Alveolar sacs

VENT SYSTEM FOR PATIENT INTERFACE

1 CROSS-REFERENCE TO RELATED APPLICATIONS

This application is the U.S. national phase of International Application No. PCT/AU2020/050167 filed Feb. 26, 2020 which designated the U.S. and claims priority to U.S. Provisional Application No. 62/810,640, filed Feb. 26, 2019, the entire contents of each of which are hereby incorporated by reference.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art

2.2.1 Human Respiratory System and its Disorders

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See *"Respiratory Physiology"*, by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/ or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising. However, these have a number of shortcomings.

2.2.2 Therapy

Various therapies, such as Continuous Positive Airway Pressure (CPAP) therapy, Non-invasive ventilation (NIV) and Invasive ventilation (IV) have been used to treat one or more of the above respiratory disorders.

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

Non-invasive ventilation (NIV) provides ventilatory support to a patient through the upper airways to assist the patient breathing and/or maintain adequate oxygen levels in the body by doing some or all of the work of breathing. The ventilatory support is provided via a non-invasive patient interface. NIV has been used to treat CSR and respiratory failure, in forms such as OHS, COPD, NMD and Chest Wall disorders. In some forms, the comfort and effectiveness of these therapies may be improved.

Invasive ventilation (IV) provides ventilatory support to patients that are no longer able to effectively breathe themselves and may be provided using a tracheostomy tube. In some forms, the comfort and effectiveness of these therapies may be improved.

2.2.3 Treatment Systems

These therapies may be provided by a treatment system or device. Such systems and devices may also be used to screen, diagnose, or monitor a condition without treating it.

A treatment system may comprise a Respiratory Pressure Therapy Device (RPT device), an air circuit, a humidifier, a patient interface, and data management.

Another form of treatment system is a mandibular repositioning device.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH₂O relative to ambient pressure. For other forms of therapy, such as the delivery of oxygen, the patient interface may not include a seal sufficient to facilitate delivery to the airways of a supply of gas at a positive pressure of about 10 cmH₂O.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus, a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to implement one or more of a number of therapies described above, such as by operating the device to generate a flow of air for delivery to an interface to the airways. The flow of air may be pressurised. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
|---|---|---|
| C-Series Tango ™ | 31.9 | 2007 |
| C-Series Tango ™ with Humidifier | 33.1 | 2007 |

-continued

| RPT Device name | A-weighted sound pressure level dB(A) | Year (approx.) |
|---|---|---|
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Humidifier

Delivery of a flow of air without humidification may cause drying of airways. The use of a humidifier with an RPT device and the patient interface produces humidified gas that minimizes drying of the nasal mucosa and increases patient airway comfort. In addition in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.4 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.5 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.6 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner of the patient, e.g. through noise or focused airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

((*) one specimen only, measured using test method specified in ISO 3744 in CPAP mode at 10 cmH$_2$O)

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |

-continued

| Object | A-weighted sound pressure dB(A) | Notes |
|---|---|---|
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a patient's condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

An aspect of certain forms of the present technology is a medical device that is easy to use, e.g., by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a medical device that may be washed in a home of a patient, e.g., in soapy water, without requiring specialised cleaning equipment.

Another aspect of the present technology is directed to a patient interface for providing respiratory therapy to a patient with a therapy flow of gas pressurized above ambient pressure and a vent system configured to discharge a flow of gas to atmosphere from a volume within the patient interface, the flow of gas being vented to atmosphere continuously throughout the patient's respiratory cycle.

Another aspect of the present technology is directed to a vent system for use with a patient interface for providing respiratory therapy to a patient with a therapy flow of gas pressurized above ambient pressure, for example by a respiratory pressure therapy device, throughout the patient's respiratory cycle, the vent system configured to discharge a vent flow of gas to atmosphere. The vent flow may be continuous throughout the patient's respiratory cycle. The vent system comprises a vent housing having a first end and a second end aligned along a longitudinal axis of the vent housing and at least one exhaust gas orifice configured to discharge exhaust gas to atmosphere; a membrane positioned within the vent housing, the membrane having a first end, a second end and a moveable portion, the first end of the membrane and the second end of the membrane spaced apart along a longitudinal axis of the membrane aligned with the longitudinal axis of the vent housing, the moveable portion of the membrane being spaced radially from a membrane-facing surface inside of the vent housing to form an exhaust gas flow passage between the moveable portion of the membrane and the membrane-facing surface, the exhaust gas flow passage being configured to allow the exhaust gas to flow from the volume through the exhaust gas flow passage to atmosphere via the at least one exhaust gas orifice during use.

3.1 Vent Structure with an Inlet, an Outlet and an Exhaust Gas Orifice

Another aspect of the present technology is directed to a vent system for use with a patient interface for providing respiratory therapy to a patient with a therapy flow of gas pressurised above ambient pressure within a therapeutic pressure range. The therapy flow of gas may be pressurised by a respiratory pressure therapy device and may be provided to the patient throughout the patient's respiratory cycle. The vent system may be configured to provide a vent flow of gas to discharge exhaust gas exhaled by the patient from a pressurised volume. The vent flow of gas may be continuous throughout the patient's respiratory cycle. The vent system may comprise: a vent housing comprising an inlet configured to receive a flow of gas from a respiratory pressure therapy device, an outlet configured to supply a therapy flow of gas to a patient interface, and at least one exhaust gas orifice configured to discharge exhaust gas to atmosphere, said at least one exhaust gas orifice being sized and shaped to maintain the therapeutic pressure in the plenum chamber in use; and a membrane positioned within the vent housing, the membrane having a first end and a second end spaced apart along a longitudinal axis of the membrane, the membrane having a moveable portion positioned between the first end of the membrane and the second end of the membrane and surrounding the longitudinal axis. The moveable portion of the membrane may be spaced radially, with respect to the longitudinal axis of the membrane, from a membrane-facing surface inside of the vent housing to form an exhaust gas flow passage between the moveable portion of the membrane and the membrane-facing surface, the exhaust gas flow passage being configured to allow gas to flow from the volume through the exhaust gas flow passage to atmosphere via the at least one exhaust gas orifice during use. The moveable portion of the membrane may be elastically deformable and configured to move radially relative to the membrane-facing surface in response to differences in pressure between an interior side of the membrane and an exterior side of the membrane, to change a cross-sectional area of the exhaust gas flow passage and regulate the vent flow of gas throughout a therapeutic pressure range.

According to another aspect of the present technology there is provided a patient interface comprising: a plenum chamber at least partially forming a volume pressurisable to a therapeutic pressure of at least 6 cmH$_2$O above ambient air pressure throughout a patient's respiratory cycle in use, said plenum chamber including a plenum chamber inlet port sized and structured to receive a therapy flow of gas for breathing by the patient, a seal-forming structure constructed and arranged to seal with a region of the patient's face surrounding an entrance to the patient's airways, said seal-forming structure having a hole therein such that the therapy flow of gas is delivered to at least an entrance to the patient's nares during use, the seal-forming structure being constructed and arranged to maintain said therapeutic pressure in the plenum chamber throughout the patient's respiratory cycle in use; a positioning and stabilising structure configured to hold the seal-forming structure in a therapeutically effective position on the patient's head; a vent structure configured to discharge a vent flow of gas to atmosphere, the vent flow of gas being continuous throughout the patient's respiratory cycle. The vent structure comprises: a vent housing comprising an inlet configured to receive a flow of gas from a respiratory pressure therapy device, an outlet configured to supply the therapy flow of gas to the plenum chamber inlet port, and at least one exhaust gas orifice configured to discharge the vent flow of gas to atmosphere, said at least one exhaust gas orifice being sized and shaped to maintain the therapeutic pressure in the plenum chamber in use; and a membrane positioned within the vent housing, the membrane having a first end and a second end spaced apart along a longitudinal axis of the membrane, the membrane having a moveable portion positioned between the first end of the membrane and the second end of the membrane and surrounding the longitudinal axis; wherein the moveable portion of the membrane is spaced radially, with respect to the longitudinal axis of the membrane, from a membrane-facing surface inside of the vent housing to form an exhaust gas flow passage between the moveable portion of the membrane and the membrane-facing surface, the exhaust gas flow passage being configured to allow gas to flow from the volume through the exhaust gas flow passage to atmosphere via the at least one exhaust gas orifice during use, wherein the moveable portion of the membrane is elastically deformable and is configured to move radially relative to the membrane-facing surface in response to differences in pressure between an interior side of the membrane and an exterior side of the membrane to change a cross-sectional area of the exhaust gas flow passage and regulate the vent flow of gas throughout the therapeutic pressure range; and wherein the patient interface is configured to allow the patient to breath from ambient through their mouth in the absence of a flow of pressurised air through the plenum chamber inlet port, or the patient interface is configured to leave the patient's mouth uncovered.

In examples of the above aspects, (a) the moveable portion of the membrane may be substantially cylindrical or frustoconical; the moveable portion of the membrane may be substantially cylindrical; (c) the vent housing may comprise a first end and a second end aligned along the longitudinal axis of the vent housing, the longitudinal axis of the membrane being aligned with the longitudinal axis of the vent housing; (d) the longitudinal axis of the membrane may be aligned substantially parallel to the direction of the flow of gas through the vent housing from the first end of the vent housing to the second end of the vent housing; (e) the moveable portion of the membrane may comprise one or more walls aligned parallel to the flow of gas through the vent housing from the first end of the vent housing to the second end of the vent housing; (f) the moveable portion of the membrane may comprise a cylindrical wall having an axis aligned parallel to the direction of the flow of gas through the vent housing from the first end of the vent housing to the second end of the vent housing; (g) the vent structure may comprise a membrane support on which the membrane is supported; (h) the membrane may be joined to the membrane support at the first end of the membrane; (i) the membrane support may be configured to connect to the vent housing; (j) the moveable portion of the membrane may be formed from silicone rubber; (k) the vent housing may comprise a first housing member at the first end of the vent housing and a second housing member at a second end of the vent housing, the first housing member and the second housing member being configured to connect together; (l) the first housing member may comprise an inlet connection portion configured to fluidly connect the vent structure to a supply conduit; (m) the inlet connection portion may be provided at or proximate the first end of the first housing portion; (n) the inlet connection portion may comprise a bayonet fitting configured to engage a corresponding fitting on the supply conduit; (o) the second housing member may comprise an outlet connection portion configured to fluidly connect the vent structure to a patient interface or to a tube configured to be connected to the patient interface; (p) the outlet connection portion may be configured to connect to the patient interface or a tube configured to be connected to the patient interface; (q) the outlet connection portion may comprise an internally threaded portion configured to engage a correspondingly threaded portion of the patient interface or patient interface tube; and/or (r) the exhaust gas flow passage may occupy a contiguous space around an entire circumference in the vent housing.

In further examples of the above aspects, (a) the vent structure may comprise a damping structure configured to damp vibration of the moveable portion of the membrane; (b) the damping structure may comprise a damping chamber within the vent housing configured to damp vibration of the moveable portion of the membrane; (c) the vent housing may at least partially form the damping chamber; (d) one of the interior side and the exterior side of the moveable portion of the membrane may face the membrane-facing surface and the other of the interior side and the exterior side of the moveable portion of the membrane may at least partially form the damping chamber; (e) the damping chamber may be in fluid communication with the pressurised volume in use; (f) the vent structure may be configured such that movement of the moveable portion of the membrane increases or decreases a volume of the damping chamber; (g) the vent housing and damping chamber may be configured to damp vibration of the moveable portion of the membrane by restricting gas exchange between the damping chamber and the pressurised volume; (h) the vent structure may comprise at least one damping orifice through which gas is able to flow into and out of the damping chamber from the pressurised volume, the damping orifice resisting gas exchange between the damping chamber and the pressurised volume; (i) the vent structure may comprise a plurality of damping orifices through which gas is able to flow into and out of the damping chamber from the pressurised volume, the plurality of damping orifices together resisting gas exchange between the damping chamber and pressurised volume; (j) the exhaust gas flow passage may comprise a region having a smaller cross-sectional area than adjacent regions of the exhaust gas flow passage; (k) the exhaust gas flow passage may comprise a restriction forming the region having a smaller cross-sectional area than adjacent regions; (l) the membrane-facing surface may be closest to the moveable portion of the membrane at the location of the restriction; (m) the membrane-facing surface may comprise a restrictor portion forming the restriction in the exhaust gas flow passage; (n) the membrane-facing surface may comprise contoured surfaces forming the restrictor portion; (o) the restrictor portion may comprise a rib in the membrane-facing surface; (p) the restrictor portion may comprise a region of increased material thickness; (q) the restrictor portion may be located centrally between the first end of the membrane and the second end of the membrane; (r) the damping chamber may comprise a first end proximate the first end of the membrane and a second end proximate the second end of the membrane, the restriction in the exhaust gas flow passage being aligned centrally between the first end of the damping chamber and the second end of the damping chamber; (s) the vent housing may be configured to reduce vibration of the moveable portion of the membrane in modes of vibration higher than a first mode of vibration; (t) the damping chamber may be further defined by one or more walls of the second housing member; and/or (u) the damping chamber may be further defined by one or more walls of the membrane support.

In further examples of the above aspects, (a) the vent housing may be configured to limit movement of the moveable portion of the membrane towards the membrane-facing surface; (b) the vent housing may be configured to contact an end of the membrane and prevent the end of the membrane from moving towards the membrane-facing surface; (c) the vent housing may comprise at least one projection configured to contact the end of the membrane and limit movement of the end of the membrane towards the membrane-facing surface; (d) the at least one projection may be positioned outside of the exhaust gas flow passage; and/or (e) the vent housing may comprise a plurality of projections and a plurality of damping orifices formed between the plurality of projections through which gas is able to flow into and out of a damping chamber from the volume, the damping orifice resisting gas exchange between the damping chamber and the volume to damp vibration of the moveable portion of the membrane.

In further examples of the above aspects, (a) the vent flow of gas may flow radially outwards at or proximate an entrance to the exhaust gas flow passage; (b) the vent flow of gas may change direction from the radial direction to an axial direction aligned with the longitudinal axis of the vent structure while passing through the entrance to the exhaust gas flow passage; (c) the vent housing may comprise a rounded surface at or proximate the entrance to the exhaust gas flow passage; (d) the rounded surface may facilitate the change in direction of the vent flow of gas at or proximate the entrance to the exhaust gas flow passage; (e) the vent housing may comprise a plurality of exhaust gas orifices; (f) the exhaust gas orifices may be spaced apart around a circumference of the vent housing; (g) the vent housing may comprise at least one diffused exhaust gas orifice and at least one undiffused exhaust gas orifice; (h) the vent housing may comprise a plurality of diffused exhaust gas orifices and a plurality of undiffused exhaust gas orifices; (i) the at least one diffused exhaust gas orifice and the at least one undiffused exhaust gas orifice may be spaced apart along the longitudinal axis of the vent housing; (j) the diffused exhaust gas orifice may be located at or proximate the first end of the vent housing; (k) the undiffused exhaust gas orifice may be located centrally between the first end of the vent housing and the second end of the vent housing; (l) the at least one diffused exhaust gas orifice may open in a lateral direction; (m) the at least one undiffused exhaust gas orifice may open in an oblique direction to the lateral direction, partially towards the second end of the vent housing; (n) the vent structure may comprise a diffuser member configured to diffuse and/or audibly muffle gas that contacts the diffuser member during use; (o) the diffuser member may be located in series with the at least one diffused exhaust gas orifice so as to require gas flowing through the at least one diffused exhaust gas orifice to flow through the diffuser member; (p) the vent structure may provide a diffused vent flow path through which gas is able to be vented through the diffuser member and the at least one diffused exhaust gas orifice; (q) the vent structure may provide an undiffused vent flow path through which gas is able to be vented through the at least one undiffused exhaust gas orifice; (r) the vent structure may be configured to allow gas to flow through the at least one undiffused exhaust gas orifice in the event the gas is unable to flow through the at least one diffused exhaust gas orifice; (s) the vent structure may be shaped to require the flow of gas to change direction to a greater extent to flow through the at least one undiffused exhaust gas orifice than through the diffused exhaust gas orifice; and/or (t) the vent structure may be shaped to require the flow of gas to change direction to flow through the undiffused exhaust gas orifice to a sufficient degree that a majority of the flow of exhaust gas passes through the diffuser member and through the diffused exhaust gas aperture unless the diffuser member becomes clogged.

In further examples of the above aspects, (a) the vent structure may comprise an exhaust gas orifice member comprising the at least one exhaust gas orifice; (b) the exhaust gas orifice member may comprise a plurality of exhaust gas orifices; (c) the exhaust gas orifice member may be configured to connect to the first housing member; (d) the exhaust gas orifice member may be formed in the shape of a ring; (e) the exhaust gas orifice member may comprise a plurality of exhaust gas orifices spaced apart around a circumference of the ring; (f) the at least one diffused exhaust gas orifice may be provided at or proximate a first end of the exhaust gas orifice member; (g) the at least one undiffused exhaust gas orifice may be provided at or proximate a second end of the exhaust gas orifice member opposite the first end of the exhaust gas orifice member; (h) the diffuser member may be retained in the vent structure by the exhaust gas orifice member; and/or (i) the diffuser member may be housed between the exhaust gas orifice member and the first housing member.

In further examples of the above aspects, (a) the moveable portion of the membrane may be positioned radially outward from the membrane-facing surface, with respect to the longitudinal axis of the membrane; (b) the moveable portion of the membrane may be configured to move inwardly to restrict the vent flow of gas; (c) the moveable portion of the membrane may be configured to constrict to move radially inwardly towards the membrane-facing surface; (d) the membrane-facing surface may be provided on an outer surface of the first housing member, the outer surface located within the vent housing; (e) the first housing member may comprise a shaft configured to project from a first end of the first housing member into the interior of the vent structure, the membrane-facing surface being provided on an outside surface of the shaft at or proximate the second end of the first housing member; (f) the shaft may be centrally located within the vent housing; (g) the shaft may be aligned with the longitudinal axis of the vent housing; (h) the rounded surface at or proximate the entrance to the exhaust gas flow passage may be a fillet on an outer periphery of the first housing member; (i) the rounded surface may be provided on the shaft at the second end of the first housing member; (j) the vent housing may comprise a plurality of projections and a plurality of damping orifices may be defined between the plurality of projections; (k) the at least one projection may be provided on the second housing member; (l) the at least one projection may be located inwardly of the membrane; (m) the at least one projection may project towards the first end of the vent housing; (n) the second housing member may comprise an inwardly extending membrane stop flange on which the at least one projection projects axially towards the first end of the vent housing; (o) the at least one projection may contact an inside surface of the membrane at the second end of the membrane; (p) the first housing member may comprise an outwardly extending flange on the shaft located at or proximate a first end of the first housing member; (q) the exhaust gas orifice member may be configured to connect to the outwardly extending flange on the first housing member facing towards the second end of the first housing member; (r) the membrane support may comprise a connection portion for connection to the vent housing; (s) the connection portion may be configured to connect directly or indirectly to the vent housing; (t) the connection portion may be cylindrically shaped and configured to fit around the exterior of the second housing member; (u) the connection portion may be concentric with the membrane; (v) the membrane support may comprise a membrane support flange formed as a flange extending inwardly from the interior of the connection portion of the membrane support; (w) the membrane may be moulded to the membrane support flange; (x) the membrane support flange may be spaced from the ends of the connection portion; (y) the exhaust gas orifice member and membrane support may be configured to connect together to connect the first housing member and the second housing member; (z) the connection portion of the membrane support may be configured to connect to the exhaust gas orifice member; (aa) the connection portion of the membrane support may be configured to be press fitted to the exterior of the exhaust gas orifice member; and/or (bb) when the membrane support is connected to both the exhaust gas orifice member and the second housing member, the membrane support flange may lie between the exhaust gas orifice member and the second housing member.

In further examples of the above aspects, (a) the moveable portion of the membrane may be supported inwardly of the membrane-facing surface; (b) the moveable portion of the membrane may be configured to move outwardly to restrict the vent flow of gas; (c) the moveable portion of the membrane may be configured to expand to move towards outwardly the membrane-facing surface; (d) the membrane-facing surface may be provided on an interior surface of the first housing member; (e) the membrane facing surface may be cylindrical or frustoconical; (f) the membrane support may comprise a baffle portion; (g) the baffle portion may be cylindrical; (h) the baffle portion may be concentric with the moveable portion of the membrane; (i) the baffle portion may be provided interior to the moveable portion of the membrane; (j) the baffle portion may have a first end connected to the moveable portion of the membrane at the first end of the membrane and a second end provided at or proximate the second end of the membrane; (k) the baffle portion may comprise an outwardly extending flange at the second end of the baffle portion; (l) the rounded surface at or proximate the entrance to the exhaust gas flow passage may be a fillet provided at the second end of the membrane support; (m) the rounded surface may be provided on the outwardly extending flange of the baffle portion of the membrane support; (n) the damping chamber may be partially defined by the baffle portion of the membrane support; (o) the damping chamber may be partially defined by the outwardly extending flange of the baffle portion; (p) the at least one projection may be provided on the first housing member; (q) the at least one projection may project radially inwardly from a cylindrical or conical surface of the first housing member; (r) the at least one projection may contact an outside surface of the membrane at the second end of the membrane; (s) the first housing member may comprise at least one intermediate exhaust gas orifice upstream of the diffuser member; (t) the diffuser member may be substantially cylindrically shaped and located over the intermediate exhaust gas orifice to diffuse and/or audibly muffle the vent flow of gas that contacts the diffuser member during use; (u) the second housing member may comprise a diffuser retaining portion; (v) the diffuser retaining portion may comprise a cylindrical sleeve configured to fit over the first housing member; (w) the first housing member may be substantially cylindrical with a second housing member connection portion at the second end of the first housing member and a diffuser support flange at the second end of the first housing member; (x) a diffuser may be retained in a diffuser channel between the diffuser support flange of the first housing member, the second housing member connection portion of the first housing member and the diffuser retaining portion of the second housing member; (y) the at least one exhaust gas orifice may be provided in the diffuser retaining portion of the second housing member or may be formed by a gap between the diffuser retaining portion of the second housing member and the diffuser support flange of the first housing member; and/or (z) a plurality of exhaust gas orifices may be provided in the diffuser retaining portion of the second housing member and/or at gaps between the diffuser retaining portion of the second housing member and the diffuser support flange of the first housing member.

3.2 Vent Structure Configured to Limit Movement of a Second End of a Moveable Membrane Another aspect of the present technology is directed to a vent system for use with a patient interface for providing respiratory therapy to a patient with a therapy flow of gas pressurised above ambient pressure within a therapeutic pressure range. The therapy flow of gas may be pressurised by a respiratory pressure therapy device and may be provided throughout the patient's respiratory cycle. The vent system may be configured to provide a vent flow of gas to discharge gas exhaled by the patient from a pressurised volume. The vent flow of gas may be continuous throughout the patient's respiratory cycle. The vent system may comprise: a vent housing comprising at least one exhaust gas orifice configured to allow exhaust gas to be discharged to atmosphere from the pressurised volume; and a membrane positioned within the vent housing, the membrane having a first end and a second end spaced apart along a longitudinal axis of the membrane, the membrane having a moveable portion positioned between the first end of the membrane and the second end of the membrane surrounding the longitudinal axis. The moveable portion of the membrane may be spaced radially, with respect to the longitudinal axis of the membrane, from a membrane-facing surface inside of the vent housing to form an exhaust gas flow passage between the moveable portion of the membrane and the membrane-facing surface, the exhaust gas flow passage configured to allow exhaust gas to flow from the pressurised volume through the exhaust gas flow passage to atmosphere via the at least one exhaust gas orifice during use. The moveable portion of the membrane may be elastically deformable and configured to move radially relative to the membrane-facing surface in response to differences in pressure between an interior side of the membrane and an exterior side of the membrane, to change a cross-sectional area of the exhaust gas flow passage and regulate the vent flow of gas throughout the therapeutic pressure range. The vent housing may be configured to limit movement of the second end of the membrane towards the membrane-facing surface.

According to another aspect of the present technology there is provided a patient interface comprising a plenum chamber at least partially forming a volume pressurisable to a therapeutic pressure of at least 6 cmH$_2$O above ambient air pressure throughout a patient's respiratory cycle in use, said plenum chamber including a plenum chamber inlet port sized and structured to receive a therapy flow of gas for breathing by a patient from the volume; a seal-forming structure constructed and arranged to seal with a region of the patient's face surrounding an entrance to the patient's airways, said seal-forming structure having a hole therein such that the therapy flow of gas is delivered to at least an entrance to the patient's nares during use, the seal-forming structure being constructed and arranged to maintain said therapeutic pressure in the plenum chamber throughout the patient's respiratory cycle in use; a positioning and stabilising structure configured to hold the seal-forming structure in a therapeutically effective position on the patient's head; a vent structure configured to discharge a vent flow of gas to atmosphere, the vent flow of gas being continuous throughout the patient's respiratory cycle. The vent structure comprising: a vent housing comprising at least one exhaust gas orifice to discharge gas to atmosphere, said at least one exhaust gas orifice being sized and shaped to maintain the therapeutic pressure in the plenum chamber in use; a membrane positioned within the vent housing, the membrane having a first end and a second end spaced apart along a longitudinal axis of the membrane, the membrane having a moveable portion positioned between the first end of the membrane and the second end of the membrane surrounding the longitudinal axis; wherein the moveable portion of the membrane is spaced radially, with respect to the longitudinal axis of the membrane, from a membrane-facing surface inside of the vent housing to form an exhaust gas flow passage between the moveable portion of the membrane and the membrane-facing surface, the exhaust gas flow passage being configured to allow exhaust gas to flow from the pressurised volume through the exhaust gas flow passage to atmosphere via the at least one exhaust gas orifice during use; wherein the moveable portion of the membrane is elastically deformable and is configured to move radially relative to the membrane-facing surface in response to differences in pressure between an interior side of the membrane and an exterior side of the membrane, to change a cross-sectional area of the exhaust gas flow passage and regulate the vent flow of gas throughout the therapeutic pressure range; wherein the first end of the membrane is fixed in position within the vent housing, and the vent housing is configured to limit movement of the second end of the membrane towards the membrane-facing surface; and wherein the patient interface is configured to allow the patient to breath from ambient through their mouth in the absence of a flow of pressurised air through the plenum chamber inlet port, or the patient interface is configured to leave the patient's mouth uncovered.

In examples of the above aspects, (a) the vent housing may contact the second end of the membrane and prevent the second end of the membrane from moving towards the membrane-facing surface; (b) the vent housing may comprise at least one projection configured to contact the second end of the membrane and limit movement of the second end of the membrane towards the membrane-facing surface; (c) the moveable portion of the membrane may be substantially cylindrical or frustoconical; (d) the vent housing may comprise a first end and a second end aligned along a longitudinal axis, the longitudinal axis of the membrane being aligned with the longitudinal axis of the vent housing; (e) the longitudinal axis of the membrane may be aligned substantially parallel to the direction of the flow of gas through the vent housing from the first end of the vent housing to the second end of the vent housing; (f) the moveable portion of the membrane may comprise one or more walls aligned parallel to the flow of gas through the vent housing from the first end of the vent housing to the second end of the vent housing; (g) the moveable portion of the membrane may comprise a cylindrical wall having an axis aligned parallel to the direction of the flow of gas through the vent housing from the first end of the vent housing to the second end of the vent housing; (h) the vent structure may comprise a membrane support on which the membrane is supported; (i) the membrane may be joined to the membrane support at the first end of the membrane; (j) the membrane support may be configured to connect to the vent housing; (k) the moveable portion of the membrane may be formed from silicone rubber; (l) the vent housing may comprise an inlet to receive a flow of gas from a respiratory pressure therapy device and an outlet to supply the therapy flow of gas to a patient interface; (m) the vent housing may comprise a first housing member at the first end of the vent housing and a second housing member at a second end of the vent housing, the first housing member and the second housing member being configured to connect together; (n) the first housing member may comprise the inlet and an inlet connection portion configured to fluidly connect the vent structure to a supply conduit; (o) the inlet connection portion may be provided at or proximate the first end of the first housing portion; (p) the inlet connection portion may comprise a bayonet fitting configured to engage a corresponding fitting on the supply conduit; (q) the second housing member may comprise the outlet and an outlet connection portion configured to fluidly connect the vent structure to a patient interface; (r) the outlet connection portion may be configured to connect to the patient interface or a tube configured to be connected to the patient interface; (s) the outlet connection portion may comprise an internally threaded portion configured to engage a correspondingly threaded portion of the patient interface or a tube configured to be connected to the patient interface; and/or (t) the exhaust gas flow passage may occupy a contiguous space around an entire circumference in the vent housing.

In further examples of the above aspects, (a) the vent structure may comprise a damping structure configured to damp vibration of the moveable portion of the membrane; (b) the damping structure may comprise a damping chamber within the vent housing; (c) the vent housing may at least partially form the damping chamber; (d) one of the interior side and the exterior side of the moveable portion of the membrane may face the membrane-facing surface and the other of the interior side and the exterior side of the moveable portion of the membrane may at least partially form the damping chamber; (e) the damping chamber may be in fluid communication with the pressurised volume in use; (f) the vent structure may be configured such that movement of the moveable portion of the membrane increases or decreases a volume of the damping chamber; (g) the vent housing and damping chamber may be configured to damp vibration of the moveable portion of the membrane by restricting gas exchange between the damping chamber and the pressurised volume; (h) the vent structure may comprise at least one damping orifice through which gas is able to flow into and out of the damping chamber from the pressurised volume, the damping orifice resisting gas exchange between the damping chamber and the pressurised volume; (i) the vent structure may comprise a plurality of damping orifices through which gas is able to flow into and out of the damping chamber from the pressurised volume, the plurality of damping orifices together resisting gas exchange between the damping chamber and pressurised volume; (j) the exhaust gas flow passage may comprise a region having a smaller cross-sectional area than adjacent regions of the exhaust gas flow passage; (k) the exhaust gas flow passage may comprise a restriction forming the region having a smaller cross-sectional area; (l) the membrane-facing surface may be closest to the moveable portion of the membrane at the location of the restriction; (m) the membrane-facing surface may comprise a restrictor portion forming the restriction in the exhaust gas flow passage; (n) the membrane-facing surface may comprise contoured surfaces forming the restrictor portion; (o) the restrictor portion may comprise a rib in the membrane-facing surface; (p) the restrictor portion may comprise a region of increased material thickness; (q) the restrictor portion may be located centrally between the first end of the membrane and the second end of the membrane; (r) the damping chamber may comprise a first end proximate the first end of the membrane and a second end proximate the second end of the membrane; (s) the restriction in the exhaust gas flow passage may be aligned centrally between the first end of the damping chamber and the second end of the damping chamber; (t) the vent housing may be configured such that vibration of the moveable portion of the membrane occurs predominantly in a first mode of vibration; (u) the damping chamber may be further defined by one or more walls of the second housing member; and/or (v) the damping chamber may be further defined by one or more walls of the membrane support.

In further examples of the above aspects, (a) the vent flow of gas may flow radially outwards at or proximate an entrance to the exhaust gas flow passage; (b) the vent flow of gas may change direction from a radial direction to an axial direction aligned with the longitudinal axis of the vent structure at or proximate the entrance to the exhaust gas flow passage; (c) the vent housing may comprise a rounded surface at or proximate the entrance to the exhaust gas flow passage; (d) the rounded surface may be configured to facilitate the change in direction of the vent flow of gas at or proximate the entrance to the exhaust gas flow passage; (e) the vent housing may comprise a plurality of exhaust gas orifices; (f) the exhaust gas orifices may be spaced apart around a circumference of the vent housing; (g) the vent housing may comprise at least one diffused exhaust gas orifice and at least one undiffused exhaust gas orifice; (h) the vent housing may comprise a plurality of diffused exhaust gas orifices and a plurality of undiffused exhaust gas orifices; (i) the at least one diffused exhaust gas orifice and the at least one undiffused exhaust gas orifice may be spaced apart along the longitudinal axis of the vent housing; (j) the diffused exhaust gas orifice may be located at or proximate the first end of the vent housing; (k) the undiffused exhaust gas orifice may be located centrally between the first end of the membrane and the second end of the vent housing; (l) the at least one diffused exhaust gas orifice may open in a lateral direction; (m) the at least one undiffused exhaust gas orifice may open in a direction partially laterally and partially towards the second end of the vent housing; (n) the vent structure may comprise a diffuser member configured to diffuse and/or audibly muffle gas that contacts the diffuser member during use; (o) the diffuser member may be located in series with the at least one diffused exhaust gas orifice so as to require gas flowing through the at least one diffused exhaust gas orifice to flow through the diffuser member; (p) the vent structure may provide a diffused vent flow path through which gas is able to be vented through the diffuser member and the at least one diffused exhaust gas orifice; (q) the vent structure may provide an undiffused vent flow path through which gas is able to be vented through the at least one undiffused exhaust gas orifice; (r) the vent structure may be configured to allow gas to flow through the at least one undiffused exhaust gas orifice in the event the gas is unable to flow through the at least one diffused exhaust gas orifice; (s) the vent structure may be shaped to require the flow of gas to change direction to a greater extent to flow through the at least one undiffused exhaust gas orifice than through the diffused exhaust gas orifice; and/or (t) the vent structure may be shaped to require the flow of gas to change direction to flow through the undiffused exhaust gas orifice to a sufficient degree that a majority of the flow of exhaust gas passes through the diffuser member and through the diffused exhaust gas aperture unless the diffuser member becomes clogged.

In further examples of the above aspects, (a) the vent structure may comprise an exhaust gas orifice member comprising the at least one exhaust gas orifice; (b) the exhaust gas orifice member may comprise a plurality of exhaust gas orifices; (c) the exhaust gas orifice member may be configured to connect to the first housing member; (d) the exhaust gas orifice member may be formed in the shape of a ring; (e) the exhaust gas orifice member may comprise a plurality of exhaust gas orifices spaced apart around a circumference of the ring; (f) the at least one diffused exhaust gas orifice may be provided at or proximate a first end of the exhaust gas orifice member; (g) the at least one undiffused exhaust gas orifice may be provided at or proximate a second end of the exhaust gas orifice member opposite the first end of the exhaust gas orifice member; (h) the diffuser member may be retained in the vent structure by the exhaust gas orifice member; and/or (i) the diffuser member may be housed between the exhaust gas orifice member and the first housing member.

In further examples of the above aspects, (a) the moveable portion of the membrane may be positioned radially outward from the membrane-facing surface, with respect to the longitudinal axis of the membrane; (b) the moveable portion of the membrane may be configured to move inwardly to restrict the vent flow of gas; (c) the moveable portion of the membrane may be configured to constrict to move inwardly towards the membrane-facing surface; (d) the membrane-facing surface may be provided on an outer surface, located within the vent housing, of the first housing member; (e) the at least one projection may be provided outside of the exhaust gas flow passage; (f) the vent housing may comprise a plurality of projections and a plurality of damping orifices defined between the plurality of projections through which gas is able to flow into and out of a damping chamber from the pressurised volume, the damping orifice resisting gas exchange between the damping chamber and the pressurised volume during use to damp vibration of the moveable portion of the membrane; (g) the first housing member may comprise a shaft configured to project from a first end of the first housing member into the interior of the vent structure, the membrane-facing surface being provided on the outside surface of the shaft at or proximate the second end of the first housing member; (h) the shaft may be centrally located within the vent housing; (i) the shaft may be aligned with the longitudinal axis of the vent housing; (j) the rounded surface at or proximate the entrance to the exhaust gas flow passage may be a fillet on an outer periphery of the first housing member; (k) the rounded surface may be provided on the shaft at the second end of the first housing member; (l) the vent housing may comprise a plurality of projections and a plurality of damping orifices may be defined between the plurality of projections; (m) the at least one projection may be provided on the second housing member; (n) the at least one projection may be located inwardly of the membrane; (o) the at least one projection may project towards the first end of the vent housing; (p) the second housing member may comprise an inwardly extending membrane stop flange on which the at least one projection projects axially towards the first end of the vent housing; (q) the at least one projection may contact an inside surface of the membrane at the second end of the membrane; (r) the first housing member may comprise an outwardly projecting flange on the shaft located at or proximate a first end of the first housing member; (s) the exhaust gas orifice member may be configured to connect to the outwardly extending flange on the first housing member facing towards the second end of the first housing member; (t) the membrane support may comprise a connection portion for connection to the vent housing; (u) the connection portion may be configured to connect directly or indirectly to the vent housing; (v) the connection portion may be cylindrically shaped and configured to fit around the exterior of the second housing member; (w) the connection portion may be concentric with the membrane; (x) the membrane support may comprise a membrane support flange formed as a flange extending inwardly from the interior of the connection portion of the membrane support; (y) the membrane may be moulded to the membrane support flange; (z) the membrane support flange may be spaced from the ends of the connection portion; (aa) the exhaust gas orifice member and membrane support may be configured to connect together to connect the first housing member and the second housing member; (ab) the connection portion of the membrane support may be configured to connect to the exhaust gas orifice member; (ac) the connection portion of the membrane support may be configured to form press fit with the exterior of the exhaust gas orifice member; and/or (ad) when the membrane support is connected to both the exhaust gas orifice member and the second housing member, the membrane support flange may lie between the exhaust gas orifice member and the second housing member.

In further examples of the above aspects, (a) the moveable portion of the membrane may be supported radially inward from the membrane-facing surface, with respect to the longitudinal axis of the membrane; (b) the moveable portion of the membrane may be configured to move outwardly to restrict the vent flow of gas; (c) the moveable portion of the membrane may be configured to expand to move towards outwardly the membrane-facing surface; (d) the membrane-facing surface may be provided on an interior surface of the first housing member; (e) the membrane facing surface may be cylindrical or frustoconical; (f) the membrane support may comprise a baffle portion; (g) the baffle portion may be cylindrical; (h) the baffle portion may be concentric with the moveable portion of the membrane; (i) the baffle portion may be provided interior to the moveable portion of the membrane; (j) the baffle portion may have a first end connected to the moveable portion of the membrane at the first end of the membrane and a second end provided at or proximate the second end of the membrane; (k) the baffle portion may comprise an outwardly extending flange at the second end of the baffle portion; (l) the rounded surface at or proximate the entrance to the exhaust gas flow passage may be a fillet provided at the second end of the membrane support; (m) the rounded surface may be provided on the outwardly extending flange of the baffle portion of the membrane support; (n) the damping chamber may be partially defined by the baffle portion of the membrane support; (o) the damping chamber may be partially defined by the outwardly extending flange of the baffle portion; (p) the at least one projection may be provided on the first housing member; (q) the at least one projection may project radially inwardly from a cylindrical or conical surface of the first housing member; (r) the at least one projection may contact an outside surface of the membrane at the second end of the membrane; (s) the first housing member may comprise at least one intermediate exhaust gas orifice upstream of the diffuser member; (t) the diffuser member may be substantially cylindrically shaped and located over the intermediate exhaust gas orifice to diffuse and/or audibly muffle the vent flow of gas; (u) the second housing member may comprise a diffuser retaining portion; (v) the diffuser retaining portion may comprise a cylindrical sleeve configured to fit over the first housing member; (w) the first housing member may be substantially cylindrical with a second housing member connection portion at the second end of the first housing member and a diffuser support flange at the second end of the first housing member; (x) a diffuser may be retained in a diffuser channel between the diffuser support flange of the first housing member, the second housing member connection portion of the first housing member and the diffuser retaining portion of the second housing member; (y) the at least one exhaust gas orifice may be provided in the diffuser retaining portion of the second housing member or may be formed by a gap between the diffuser retaining portion of the second housing member and the diffuser support flange of the first housing member; and/or (z) a plurality of exhaust gas orifices may be provided in the diffuser retaining portion of the second housing member and/or at gaps between the diffuser retaining portion of the second housing member and the diffuser support flange of the first housing member.

3.3 Vent Structure Having a Damping Structure to Damp Vibration of a Membrane Another aspect of the present technology is directed to a vent system for use with a patient interface for providing respiratory therapy to a patient with a therapy flow of gas pressurised above ambient pressure within a therapeutic pressure range. The therapy flow of gas may be pressurised by a respiratory pressure therapy device and may be provided throughout the patient's respiratory cycle. The vent system may be configured to provide a vent flow of gas to discharge gas exhaled by the patient from a pressurised volume. The vent flow of gas may be continuous throughout the patient's respiratory cycle. The vent system may comprise: a vent housing comprising at least one exhaust gas orifice configured to allow exhaust gas to be discharged to atmosphere from the pressurised volume; a membrane positioned within the vent housing, the membrane having a moveable portion spaced from a membrane-facing surface inside of the vent housing to form an exhaust gas flow passage between the moveable portion of the membrane and the membrane-facing surface, the exhaust gas flow passage being configured to allow exhaust gas to flow from the pressurised volume to atmosphere via the at least one exhaust gas orifice; and a damping structure configured to damp vibration of the moveable portion of the membrane, the damping structure comprising a damping chamber within the vent housing. The moveable portion of the membrane may be elastically deformable and configured to move relative to the membrane-facing surface in response to differences in pressure between a first side of the membrane and a second side of the membrane, to change a cross-sectional area of the exhaust gas flow passage and regulate the vent flow of gas throughout a therapeutic pressure range. The first side of the moveable portion of the membrane may face the membrane-facing surface and the second side of the moveable portion of the membrane partially defines the damping chamber.

A patient interface comprising: a plenum chamber at least partially forming a volume pressurisable to a therapeutic pressure of at least 6 cmH$_2$O above ambient air pressure throughout a patient's respiratory cycle in use, said plenum chamber including a plenum chamber inlet port sized and structured to receive a therapy flow of gas for breathing by the patient; a seal-forming structure constructed and arranged to seal with a region of the patient's face surrounding an entrance to the patient's airways, said seal-forming structure having a hole therein such that the therapy flow of gas is delivered to at least an entrance to the patient's nares during use, the seal-forming structure being constructed and arranged to maintain said therapeutic pressure in the plenum chamber throughout the patient's respiratory cycle in use; a positioning and stabilising structure configured to hold the seal-forming structure in a therapeutically effective position on the patient's head; a vent structure to discharge a vent flow of gas to atmosphere, the vent flow of gas being continuous throughout the patient's respiratory cycle. The vent structure comprising: a vent housing comprising at least one exhaust gas orifice to discharge gas to atmosphere, said at least one exhaust gas orifice being sized and shaped to maintain the therapeutic pressure in the plenum chamber in use; and a membrane positioned within the vent housing, the membrane having a moveable portion spaced from a membrane-facing surface inside of the vent housing to form an exhaust gas flow passage between the moveable portion of the membrane and the membrane-facing surface, the exhaust gas flow passage being configured to allow exhaust gas to flow from the pressurised volume to atmosphere via the at least one exhaust gas orifice, a damping structure configured to damp vibration of the moveable portion of the membrane, the damping structure comprising a damping chamber within the vent housing; wherein the moveable portion of the membrane is elastically deformable and is configured to move relative to the membrane-facing surface in response to differences in pressure between a first side of the membrane and a second side of the membrane, to change a cross-sectional area of the exhaust gas flow passage and regulate the vent flow of gas throughout a therapeutic pressure range; wherein the first side of the moveable portion of the membrane faces the membrane-facing surface and the second side of the moveable portion of the membrane partially defines the damping chamber; and wherein the patient interface is configured to allow the patient to breath from ambient through their mouth in the absence of a flow of pressurised air through the plenum chamber inlet port, or the patient interface is configured to leave the patient's mouth uncovered.

In examples of the above aspects, (a) the vent housing may partially define the damping chamber; (b) the damping chamber may be in fluid communication with the pressurised volume in use; (c) the vent structure may be configured such that movement of the moveable portion of the membrane increases or decreases a volume of the damping chamber; (d) the vent housing and damping chamber may be configured to damp vibration of the moveable portion of the membrane by restricting gas exchange between the damping chamber and the pressurised volume; (e) the vent structure may comprise at least one damping orifice through which gas is able to flow into and out of the damping chamber from the pressurised volume, the damping orifice resisting gas exchange between the damping chamber and the pressurised volume; (f) the vent structure may comprise a plurality of damping orifices through which gas is able to flow into and out of the damping chamber from the pressurised volume, the plurality of damping orifices together resisting gas exchange between the damping chamber and pressurised volume; (g) the damping chamber may comprise a first end proximate the first end of the membrane and a second end proximate the second end of the membrane; (h) the exhaust gas flow passage may comprise a region having a smaller cross-sectional area than adjacent regions of the exhaust gas flow passage; (i) the exhaust gas flow passage may comprise a restriction forming the region having a smaller cross-sectional area; (j) the membrane-facing surface may be closest to the moveable portion of the membrane at the location of the restriction; (k) the restriction in the exhaust gas flow passage may be aligned centrally between the first end of the damping chamber and the second end of the damping chamber; (l) the membrane-facing surface may comprise a restrictor portion forming the restriction in the exhaust gas flow passage; (m) the membrane-facing surface may comprise contoured surfaces forming the restrictor portion; (n) the restrictor portion may comprise a rib in the membrane-facing surface; (o) the restrictor portion may comprise a region of increased material thickness; (p) the restrictor portion may be located centrally between the first end of the membrane and the second end of the membrane; (q) the damping chamber may comprise a first end proximate the first end of the membrane and a second end proximate the second end of the membrane, the restriction in the exhaust gas flow passage being aligned centrally between the first end of the damping chamber and the second end of the damping chamber; (r) the vent housing may be configured to reduce vibration of the moveable portion of the membrane in modes of vibration higher than a first mode of vibration; (s) the vent housing may comprise an inlet to receive a flow of gas from a respiratory pressure therapy device and an outlet to supply the therapy flow of gas to the patient interface; (t) the vent housing may comprise a first housing member at a first end of the vent housing and a second housing member at a second end of the vent housing, the first housing member and the second housing member being configured to connect together; (u) the first housing member may comprise the inlet and an inlet connection portion configured to fluidly connect the vent structure to a supply conduit; and/or (v) the second housing member may comprise the outlet and an outlet connection portion configured to fluidly connect the vent structure to a patient interface; and/or (w) the exhaust gas flow passage may occupy a contiguous space about an entire circumference in the vent housing.

3.4 Vent Housing that Reduces Vibration of the Membrane in Modes Higher than the First Mode Another aspect of the present technology is directed to a vent system for use with a patient interface for providing respiratory therapy to a patient with a therapy flow of gas pressurised above ambient pressure within a therapeutic pressure range. The therapy flow of gas may be pressurised by a respiratory pressure therapy device and may be provided throughout the patient's respiratory cycle. The vent system may be configured to provide a vent flow of gas to discharge gas exhaled by the patient from a pressurised volume. The vent flow of gas may be continuous throughout the patient's respiratory cycle. The vent system may comprise: a vent housing comprising at least one exhaust gas orifice configured to allow exhaust gas to be discharged to atmosphere from the pressurised volume; and a membrane within the vent housing, the membrane having a moveable portion. The moveable portion of the membrane may be spaced from a membrane-facing surface inside of the vent housing to form an exhaust gas flow passage between the moveable portion of the membrane and the membrane-facing surface, the exhaust gas flow passage being configured to allow exhaust gas to flow from the pressurised volume through the exhaust gas flow passage to atmosphere via the at least one exhaust gas orifice. The moveable portion of the membrane may be elastically deformable and configured to move relative to the membrane-facing surface, in response to differences in pressure between a first side of the membrane and a second side of the membrane, to change a cross-sectional area of the exhaust gas flow passage and regulate the vent flow of gas throughout the therapeutic pressure range. The vent housing may be configured to reduce vibration of the moveable portion of the membrane in modes higher than a first mode of vibration.

According to another aspect of the present technology there is provided a patient interface comprising a plenum chamber at least partially defining a pressurised volume of the patient interface pressurisable to a therapeutic pressure of at least 6 cmH$_2$O above ambient air pressure throughout the patient's respiratory cycle in use, said plenum chamber including a plenum chamber inlet port sized and structured to receive a therapy flow of gas for breathing by a patient from the pressurised volume; a seal-forming structure constructed and arranged to form a seal with a region of the patient's face surrounding an entrance to the patient's airways, said seal-forming structure having a hole therein such that the therapy flow of gas is delivered to at least an entrance to the patient's nares, the seal-forming structure constructed and arranged to maintain said therapeutic pressure in the plenum chamber throughout the patient's respiratory cycle in use; a positioning and stabilising structure to provide a force to hold the seal-forming structure in a therapeutically effective position on the patient's head; a vent structure to allow a vent flow of gas to discharge exhaust gas exhaled by the patient from the pressurised volume to ambient, the vent flow of gas being continuous throughout the patient's respiratory cycle, said vent structure being sized and shaped to maintain the therapeutic pressure in the plenum chamber in use. The vent structure comprises: a vent housing comprising at least one exhaust gas orifice to allow exhaust gas to be discharged to atmosphere from the pressurised volume; a membrane within the vent housing, the membrane having a moveable portion; wherein the moveable portion of the membrane is spaced from a membrane-facing surface inside of the vent housing to form an exhaust gas flow passage between the moveable portion of the membrane and the membrane-facing surface, the exhaust gas flow passage allowing exhaust gas to flow from the pressurised volume through the exhaust gas flow passage to atmosphere via the at least one exhaust gas orifice during use; wherein the moveable portion of the membrane is elastically deformable and is configured to move relative to the membrane-facing surface, in response to differences in pressure between a first side of the membrane and a second side of the membrane, to change a cross-sectional area of the exhaust gas flow passage and regulate the vent flow of gas throughout the therapeutic pressure range, wherein the vent housing is configured to reduce vibration of the moveable portion of the membrane in modes of vibration higher than a first mode of vibration; and wherein the patient interface is configured to allow the patient to breath from ambient through their mouth in the absence of a flow of pressurised air through the plenum chamber inlet port, or the patient interface is configured to leave the patient's mouth uncovered.

In examples of the above aspects, (a) the vent structure may comprise a damping structure configured to damp vibration of the moveable portion of the membrane; (b) the damping structure may comprise a damping chamber within the vent housing; (c) the vent housing may partially define the damping chamber; (d) the first side of the moveable portion of the membrane may face the membrane-facing surface and the second side of the moveable portion of the membrane may partially define the damping chamber; (e) the damping chamber may be in fluid communication with the pressurised volume in use; (f) the vent structure may be configured such that movement of the moveable portion of the membrane increases or decreases a volume of the damping chamber; (g) the vent housing and damping chamber may be configured to damp vibration of the moveable portion of the membrane by restricting gas exchange between the damping chamber and the pressurised volume; (h) the vent structure may comprise at least one damping orifice through which gas is able to flow into and out of the damping chamber from the pressurised volume, the damping orifice resisting gas exchange between the damping chamber and the pressurised volume; (i) the vent structure may comprise a plurality of damping orifices through which gas is able to flow into and out of the damping chamber from the pressurised volume, the plurality of damping orifices together resisting gas exchange between the damping chamber and pressurised volume; (j) the damping chamber may comprise a first end proximate a first end of the membrane and a second end proximate a second end of the membrane; (k) the exhaust gas flow passage may comprise a region having a smaller cross-sectional area than adjacent regions of the exhaust gas flow passage; (l) the exhaust gas flow passage may comprise a restriction forming the region having a smaller cross-sectional area; (m) the membrane-facing surface may be closest to the moveable portion of the membrane at the location of the restriction; (n) the membrane-facing surface may comprise a restrictor portion forming the restriction in the exhaust gas flow passage; (o) the membrane-facing surface may comprise contoured surfaces forming the restrictor portion; (p) the restrictor portion may comprise a rib in the membrane-facing surface; (q) the restrictor portion may comprise a region of increased material thickness; (r) the restrictor portion may be located centrally between the first end of the membrane and the second end of the membrane; (s) the restriction in the exhaust gas flow passage may be aligned centrally between the first end of the damping chamber and the second end of the damping chamber; (t) the vent housing may comprise an inlet to receive a flow of gas from a respiratory pressure therapy device and an outlet to supply the therapy flow of gas to the patient interface; (u) the vent housing may comprise a first housing member at a first end of the vent housing and a second housing member at a second end of the vent housing, the first housing member and the second housing member being configured to connect together; (v) the first housing member may comprise the inlet and an inlet connection portion configured to fluidly connect the vent structure to a supply conduit; (w) the second housing member may comprise the outlet and an outlet connection portion configured to fluidly connect the vent structure to the patient interface; (x) the exhaust gas flow passage may occupy a contiguous space about an entire circumference in the vent housing.

3.5 Vent Housing with Stagnant Air Cavity

Another aspect of the present technology is directed to a vent system for use with a patient interface for providing respiratory therapy to a patient with a therapy flow of gas pressurised above ambient pressure within a therapeutic pressure range. The therapy flow of gas may be pressurised by a respiratory pressure therapy device and may be provided throughout the patient's respiratory cycle. The vent system configured to provide a vent flow of gas to discharge gas exhaled by the patient from a pressurised volume. The vent flow of gas may be continuous throughout the patient's respiratory cycle. The vent system may comprise: a vent housing comprising at least one exhaust gas orifice to allow exhaust gas to be discharged to atmosphere from the pressurised volume; a membrane within the vent housing, the membrane having a moveable portion having a first side and a second side; and a stagnant air cavity within the vent housing on the first side of the moveable portion of the membrane, the moveable portion of the membrane at least partially defining the stagnant air cavity. The moveable portion of the membrane may be spaced from a membrane-facing surface inside of the vent housing to form an exhaust gas flow passage on the second side of the membrane between the moveable portion of the membrane and the membrane-facing surface, the exhaust gas flow passage allowing exhaust gas to flow from the pressurised volume through the exhaust gas flow passage to atmosphere via the at least one exhaust gas orifice. The moveable portion of the membrane may be elastically deformable and is configured to move relative to the membrane-facing surface, in response to differences in pressure between the first side of the membrane and the second side of the membrane, to change a cross-sectional area of the exhaust gas flow passage and regulate the vent flow of gas throughout the therapeutic pressure range.

According to another aspect of the present technology there is provided a patient interface comprising: a plenum chamber at least partially forming a volume pressurisable to a therapeutic pressure of at least 6 cmH$_2$O above ambient air pressure throughout a patient's respiratory cycle in use, said plenum chamber including a plenum chamber inlet port sized and structured to receive a therapy flow of gas for breathing by the patient; a seal-forming structure constructed and arranged to seal with a region of the patient's face surrounding an entrance to the patient's airways, said seal-forming structure having a hole therein such that the therapy flow of gas is delivered to at least an entrance to the patient's nares during use, the seal-forming structure being constructed and arranged to maintain said therapeutic pressure in the plenum chamber throughout the patient's respiratory cycle in use; a positioning and stabilising structure configured to hold the seal-forming structure in a therapeutically effective position on the patient's head; a vent structure configured to discharge a vent flow of gas to atmosphere, the vent flow of gas being continuous throughout the patient's respiratory cycle. The vent structure comprises: a vent housing comprising at least one exhaust gas orifice to discharge gas to atmosphere, said at least one exhaust gas orifice being sized and shaped to maintain the therapeutic pressure in the plenum chamber in use; a membrane positioned within the vent housing, the membrane having a moveable portion having a first side and a second side; a stagnant air cavity positioned within the vent housing on the first side of the moveable portion of the membrane, the moveable portion of the membrane at least partially forming the stagnant air cavity; wherein the moveable portion of the membrane is spaced from a membrane-facing surface inside of the vent housing to form an exhaust gas flow passage on the second side of the membrane between the moveable portion of the membrane and the membrane-facing surface, the exhaust gas flow passage being configured to allow exhaust gas to flow from the pressurised volume through the exhaust gas flow passage to atmosphere via the at least one exhaust gas orifice during use, wherein the moveable portion of the membrane is elastically deformable and is configured to move relative to the membrane-facing surface, in response to differences in pressure between the first side of the membrane and the second side of the membrane, to change a cross-sectional area of the exhaust gas flow passage and regulate the vent flow of gas throughout the therapeutic pressure range; and wherein the patient interface is configured to allow the patient to breath from ambient through their mouth in the absence of a flow of pressurised air through the plenum chamber inlet port, or the patient interface is configured to leave the patient's mouth uncovered.

In examples of the above aspects, (a) the vent housing may partially define the stagnant air cavity; (b) the stagnant air cavity may comprise a damping chamber configured to damp vibration of the moveable portion of the membrane; (c) the vent housing may partially define the damping chamber; (d) one of the first side and the second side of the moveable portion of the membrane may face the membrane-facing surface and the other of the first side and the second side of the moveable portion of the membrane may partially define the damping chamber; (e) the damping chamber may be in fluid communication with the pressurised volume in use; (f) the vent structure may be configured such that movement of the moveable portion of the membrane increases or decreases a volume of the damping chamber; (g) the vent housing and damping chamber may be configured to damp vibration of the moveable portion of the membrane by restricting gas exchange between the damping chamber and the pressurised volume; (h) the vent structure may comprise at least one damping orifice through which gas is able to flow into and out of the damping chamber from the pressurised volume, the damping orifice resisting gas exchange between the damping chamber and the pressurised volume; (i) the vent structure may comprise a plurality of damping orifices through which gas is able to flow into and out of the damping chamber from the pressurised volume, the plurality of damping orifices together resisting gas exchange between the damping chamber and pressurised volume; (j) the damping chamber may comprise a first end proximate a first end of the membrane and a second end proximate a second end of the membrane; (k) the exhaust gas flow passage may comprise a region having a smaller cross-sectional area than adjacent regions of the exhaust gas flow passage; (l) the exhaust gas flow passage may comprise a restriction forming the region having a smaller cross-sectional area; (m) the membrane-facing surface may be closest to the moveable portion of the membrane at the location of the restriction; (n) the membrane-facing surface may comprise a restrictor portion forming the restriction in the exhaust gas flow passage; (o) the membrane-facing surface may comprise contoured surfaces forming the restrictor portion; (p) the restrictor portion may comprise a rib in the membrane-facing surface; (q) the restrictor portion may comprise a region of increased material thickness; (e) the restrictor portion may be located centrally between the first end of the membrane and the second end of the membrane; (s) the restriction in the exhaust gas flow passage may be aligned centrally between the first end of the damping chamber and the second end of the damping chamber; (t) the vent housing may comprise an inlet to receive a flow of gas from a respiratory pressure therapy device and an outlet to supply the therapy flow of gas to the patient interface; (u) the vent housing may comprise a first housing member at a first end of the vent housing and a second housing member at a second end of the vent housing, the first housing member and the second housing member being configured to connect together; (v) the first housing member may comprise the inlet and an inlet connection portion configured to fluidly connect the vent structure to a supply conduit; (w) the second housing member may comprise the outlet and an outlet connection portion configured to fluidly connect the vent structure to the patient interface; (x) the vent housing may be configured such that vibration of the moveable portion of the membrane occurs predominantly in a first mode of vibration; and/or (y) the exhaust gas flow passage may occupy a contiguous space about an entire circumference in the vent housing.

In further examples of the above aspects: (a) the first side of the moveable portion of the membrane faces radially inward and the second side of the moveable portion of the membrane faces radially outward; (b) the first side of the moveable portion of the membrane faces radially outward and the second side of the moveable portion of the membrane faces radially inward; and/or (c) the membrane has a first end and a second end spaced apart along a longitudinal axis of the membrane, the moveable portion being located between the first end of the membrane and the second end of the membrane surrounding the longitudinal axis.

3.6 Exhaust Gas Flow Passage Comprising a Region of Smaller Cross-Sectional Area than Adjacent Regions Another aspect of the present technology is directed to a vent system for use with a patient interface for providing respiratory therapy to a patient with a therapy flow of gas pressurised above ambient pressure within a therapeutic pressure range. The therapy flow of gas may be pressurised by a respiratory pressure therapy device and may be provided throughout the patient's respiratory cycle. The vent system may be configured to provide a vent flow of gas to discharge gas exhaled by the patient from a pressurised volume, the vent system comprising: a vent housing comprising at least one exhaust gas orifice to allow exhaust gas to be discharged to atmosphere from the pressurised volume; a membrane within the vent housing, the membrane having a moveable portion having a first side and a second side, wherein the moveable portion of the membrane is spaced from a membrane-facing surface inside of the vent housing to form an exhaust gas flow passage on the second side of the membrane between the moveable portion of the membrane and the membrane-facing surface, the exhaust gas flow passage allowing exhaust gas to flow from the pressurised volume through the exhaust gas flow passage to atmosphere via the at least one exhaust gas orifice during use; wherein the exhaust gas flow passage comprises a region having a smaller cross-sectional area than at adjacent regions of the exhaust gas flow passage, and wherein the moveable portion of the membrane is elastically deformable and is configured to move relative to the membrane-facing surface, in response to differences in pressure between the first side of the membrane and the second side of the membrane, to change a cross-sectional area of the exhaust gas flow passage and regulate the vent flow of gas throughout the therapeutic pressure range.

A patient interface comprising: a plenum chamber at least partially forming a volume pressurisable to a therapeutic pressure of at least 6 cmH$_2$O above ambient air pressure throughout the patient's respiratory cycle in use, said plenum chamber including a plenum chamber inlet port sized and structured to receive a therapy flow of gas for breathing by a patient from the volume; a seal-forming structure constructed and arranged to seal with a region of the patient's face surrounding an entrance to the patient's airways, said seal-forming structure having a hole therein such that the therapy flow of gas is delivered to at least an entrance to the patient's nares during use, the seal-forming structure constructed and arranged to maintain said therapeutic pressure in the plenum chamber throughout the patient's respiratory cycle in use; a positioning and stabilising structure configured to hold the seal-forming structure in a therapeutically effective position on the patient's head; a vent structure configured to discharge a vent flow of gas to atmosphere, the vent flow of gas being continuous throughout the patient's respiratory cycle. The vent structure comprising: a vent housing comprising at least one exhaust gas orifice configured to discharge gas to atmosphere, said at least one exhaust gas orifice being sized and shaped to maintain the therapeutic pressure in the plenum chamber in use; a membrane positioned within the vent housing, the membrane having a first end and a second end spaced apart along a longitudinal axis of the membrane, the membrane having a moveable portion positioned between the first end of the membrane and the second end of the membrane surrounding the longitudinal axis, wherein the moveable portion of the membrane comprises a first side and a second side and is spaced radially, with respect to the longitudinal axis of the membrane, from a membrane-facing surface inside of the vent housing to form an exhaust gas flow passage on the second side of the membrane between the moveable portion of the membrane and the membrane-facing surface, the exhaust gas flow passage being configured to allow exhaust gas to flow from the pressurised volume through the exhaust gas flow passage to atmosphere via the at least one exhaust gas orifice during use; wherein the exhaust gas flow passage comprises a region between the moveable portion of the membrane and the membrane-facing surface having a smaller cross-sectional area than adjacent regions of the exhaust gas flow passage, and wherein the moveable portion of the membrane is elastically deformable and is configured to move radially relative to the membrane-facing surface, in response to differences in pressure between the first side of the membrane and the second side of the membrane, to change a cross-sectional area of the exhaust gas flow passage and regulate the vent flow of gas throughout the therapeutic pressure range; and wherein the patient interface is configured to allow the patient to breath from ambient through their mouth in the absence of a flow of pressurised air through the plenum chamber inlet port, or the patient interface is configured to leave the patient's mouth uncovered In examples of the above aspects, (a) the exhaust gas flow passage may comprise a restriction forming the region having a smaller cross-sectional area; (b) the membrane-facing surface may be closest to the moveable portion of the membrane at the location of the restriction; (c) the membrane-facing surface may comprise a restrictor portion forming the restriction in the exhaust gas flow passage; (d) the membrane-facing surface may comprise contoured surfaces forming the restrictor portion; (e) the restrictor portion may comprise a rib in the membrane-facing surface; (f) the restrictor portion may be located centrally between a first end of the membrane and a second end of the membrane; (g) the vent structure may comprise a damping chamber within the vent housing configured to damp vibration of the moveable portion of the membrane, wherein the damping chamber comprises a first end proximate the first end of the membrane and a second end proximate the second end of the membrane, the restriction in the exhaust gas flow passage being aligned centrally between the first end of the damping chamber and the second end of the damping chamber; (h) the vent housing may comprise an inlet to receive a flow of gas from a respiratory pressure therapy device and an outlet to supply the therapy flow of gas to the patient interface; (i) the vent housing may comprise a first housing member at a first end of the vent housing and a second housing member at a second end of the vent housing, the first housing member and the second housing member being configured to connect together; (j) the first housing member may comprise the inlet and an inlet connection portion configured to fluidly connect the vent structure to a supply conduit; (k) the second housing member may comprise the outlet and an outlet connection portion configured to fluidly connect the vent structure to the patient interface; and/or (l) the exhaust gas flow passage may occupy a contiguous space about an entire circumference in the vent housing.

3.7 Vent Structure Having Radially Outward Deforming Membrane

Another aspect of the present technology is directed to a vent system for use with a patient interface for providing respiratory therapy to a patient with a therapy flow of gas pressurised above ambient pressure within a therapeutic pressure range. The therapy flow of gas may be pressurised by a respiratory pressure therapy device and may be provided throughout the patient's respiratory cycle. The vent system may be configured to provide a vent flow of gas to discharge gas exhaled by the patient from a pressurised volume. The vent flow of gas may be continuous throughout the patient's respiratory cycle. The vent system may comprise: a vent housing comprising at least one exhaust gas orifice to allow exhaust gas to be discharged to atmosphere from the pressurised volume; and a membrane within the vent housing, the membrane having a first end and a second end spaced apart along a longitudinal axis of the membrane, the membrane having a moveable portion between the first end of the membrane and the second end of the membrane surrounding the longitudinal axis. The moveable portion of the membrane may be spaced radially inward, with respect to the longitudinal axis of the membrane, from a membrane-facing surface inside of the vent housing to form an exhaust gas flow passage between the moveable portion of the membrane and the membrane-facing surface, the exhaust gas flow passage allowing exhaust gas to flow from the pressurised volume through the exhaust gas flow passage to atmosphere via the at least one exhaust gas orifice during use. The moveable portion of the membrane is elastically deformable and is configured to move radially relative to the membrane-facing surface in response to differences in pressure between an interior side of the membrane and an exterior side of the membrane, to change a cross-sectional area of the exhaust gas flow passage and regulate the vent flow of gas throughout the therapeutic pressure range.

According to another aspect of the present technology there is provided a patient interface comprising: a plenum chamber at least partially forming a volume pressurisable to a therapeutic pressure of at least 6 cmH$_2$O above ambient air pressure throughout a patient's respiratory cycle in use, said plenum chamber including a plenum chamber inlet port sized and structured to receive a therapy flow of gas for breathing by a patient from the pressurised volume; a seal-forming structure constructed and arranged to seal with a region of the patient's face surrounding an entrance to the patient's airways, said seal-forming structure having a hole therein such that the therapy flow of gas is delivered to at least an entrance to the patient's nares, the seal-forming structure constructed and arranged to maintain said therapeutic pressure in the plenum chamber throughout the patient's respiratory cycle in use; a positioning and stabilising structure configured to hold the seal-forming structure in a therapeutically effective position on the patient's head; a vent structure configured to discharge a vent flow of gas to atmosphere, the vent flow of gas being continuous throughout the patient's respiratory cycle. The vent structure comprises: a vent housing comprising at least one exhaust gas orifice configured to discharge gas to atmosphere, said at least one exhaust gas orifice being sized and shaped to maintain the therapeutic pressure in the plenum chamber in use; a membrane positioned within the vent housing, the membrane having a first end and a second end spaced apart along a longitudinal axis of the membrane, the membrane having a moveable portion positioned between the first end of the membrane and the second end of the membrane surrounding the longitudinal axis; wherein the moveable portion of the membrane is spaced radially inward, with respect to the longitudinal axis of the membrane, from a membrane-facing surface inside of the vent housing to form an exhaust gas flow passage between the moveable portion of the membrane and the membrane-facing surface, the exhaust gas flow passage being configured to allow exhaust gas to flow from the pressurised volume through the exhaust gas flow passage to atmosphere via the at least one exhaust gas orifice during use, wherein the moveable portion of the membrane is elastically deformable and is configured to move radially relative to the membrane-facing surface in response to differences in pressure between an interior side of the membrane and an exterior side of the membrane, to change a cross-sectional area of the exhaust gas flow passage and regulate the vent flow of gas throughout the therapeutic pressure range; and wherein the patient interface is configured to allow the patient to breath from ambient through their mouth in the absence of a flow of pressurised air through the plenum chamber inlet port, or the patient interface is configured to leave the patient's mouth uncovered.

In examples of the above aspects, (a) the moveable portion of the membrane may be substantially cylindrical or frustoconical; (b) the vent housing may comprise a first end and a second end aligned along the longitudinal axis of the vent housing, the longitudinal axis of the membrane being aligned with the longitudinal axis of the vent housing; (c) the longitudinal axis of the membrane may be aligned substantially parallel to the direction of the flow of gas through the vent housing from the first end of the vent housing to the second end of the vent housing; (d) the moveable portion of the membrane may comprise one or more walls aligned parallel to the flow of gas through the vent housing from the first end of the vent housing to the second end of the vent housing; (e) the moveable portion of the membrane may comprise a cylindrical wall having an axis aligned parallel to the direction of the flow of gas through the vent housing from the first end of the vent housing to the second end of the vent housing; (f) the vent structure may comprise a membrane support on which the membrane is supported; (g) the membrane may be moulded to the membrane support at the first end of the membrane; (h) the membrane support may be configured to connect to the vent housing; (i) the moveable portion of the membrane may be formed from silicone rubber; (j) the vent housing may comprise a first housing member at the first end of the vent housing and a second housing member at a second end of the vent housing, the first housing member and the second housing member being configured to connect together; (k) the first housing member may comprise an inlet connection portion configured to fluidly connect the vent structure to a supply conduit; (l) the inlet connection portion may be provided at or proximate the first end of the first housing portion; (m) the inlet connection portion may comprise a bayonet fitting configured to engage a corresponding fitting on the supply conduit; (n) the second housing member may comprise an outlet connection portion configured to fluidly connect the vent structure to a patient interface; (o) the outlet connection portion may be configured to connect to the patient interface or a tube connected to the patient interface; (p) the outlet connection portion may comprise an internally threaded portion configured to engage a correspondingly threaded portion of the patient interface or patient interface tube; and/or (q) the exhaust gas flow passage may occupy a contiguous space about an entire circumference in the vent housing.

In further examples of the above aspects, (a) the vent structure may comprise a damping structure configured to damp vibration of the moveable portion of the membrane; (b) the damping structure may comprise a damping chamber within the vent housing; (c) the vent housing may partially define the damping chamber; (d) one of the interior side and the exterior side of the membrane may face the membrane-facing surface and the other of the interior side and the exterior side of the membrane partially defines the damping chamber; (e) the damping chamber may be in fluid communication with the pressurised volume in use; (f) the vent structure may be configured such that movement of the moveable portion of the membrane increases or decreases a volume of the damping chamber; (g) the vent housing and damping chamber may be configured to damp vibration of the moveable portion of the membrane by restricting gas exchange between the damping chamber and the pressurised volume; (h) the vent structure may comprise at least one damping orifice through which gas is able to flow into and out of the damping chamber from the pressurised volume, the damping orifice resisting gas exchange between the damping chamber and the pressurised volume; (i) the vent structure may comprise a plurality of damping orifices through which gas is able to flow into and out of the damping chamber from the pressurised volume, the plurality of damping orifices together resisting gas exchange between the damping chamber and pressurised volume; (j) the exhaust gas flow passage may comprise a region having a smaller cross-sectional area than adjacent regions of the exhaust gas flow passage; (k) the exhaust gas flow passage may comprise a restriction forming the region having a smaller cross-sectional area; (l) the membrane-facing surface may be closest to the moveable portion of the membrane at the location of the restriction; (m) the membrane-facing surface may comprise a restrictor portion forming the restriction in the exhaust gas flow passage; (n) the membrane-facing surface may comprise contoured surfaces forming the restrictor portion; (o) the restrictor portion may comprise a rib in the membrane-facing surface; (p) the restrictor portion may comprise a region of increased material thickness; (q) the restrictor portion may be located centrally between the first end of the membrane and the second end of the membrane; (r) the damping chamber may comprise a first end proximate the first end of the membrane and a second end proximate the second end of the membrane; (s) the restriction in the exhaust gas flow passage may be aligned centrally between the first end of the damping chamber and the second end of the damping chamber; (t) the vent housing may be configured such that vibration of the moveable portion of the membrane occurs predominantly in a first mode of vibration; (u) the damping chamber may be further defined by one or more walls of the second housing member; and/or (v) the damping chamber may be further defined by one or more walls of the membrane support.

In further examples of the above aspects, (a) the vent housing may be configured to limit movement of the moveable portion of the membrane towards the membrane-facing surface; (b) the vent housing may contact an end of the membrane and prevent the end of the membrane from moving towards the membrane-facing surface; (c) the vent housing may comprise at least one projection configured to contact the end of the membrane and limit movement of the end of the membrane towards the membrane-facing surface; (d) the at least one projection is provided outside of the exhaust gas flow passage; and/or (e) the vent housing may comprise a plurality of projections and a plurality of damping orifices may be defined between the plurality of projections through which gas is able to flow into and out of a damping chamber from the pressurised volume, the damping orifices resisting gas exchange between the damping chamber and the pressurised volume to damp vibration of the moveable portion of the membrane.

In further examples of the above aspects, (a) the vent flow of gas may flow radially outwards at or proximate an entrance to the exhaust gas flow passage; (b) the vent flow of gas may change direction from the radial direction to an axial direction aligned with the longitudinal axis of the vent structure while passing through the entrance to the exhaust gas flow passage; (c) the vent housing may comprise a rounded surface at or proximate the entrance to the exhaust gas flow passage; (d) the rounded surface may facilitate the change in direction of the vent flow of gas proximate the entrance to the exhaust gas flow passage; (e) the vent housing may comprise a plurality of exhaust gas orifices; (f) the exhaust gas orifices may be spaced apart around a circumference of the vent housing; (g) the vent housing may comprise at least one diffused exhaust gas orifice and at least one undiffused exhaust gas orifice; (h) the vent housing may comprise a plurality of diffused exhaust gas orifices and a plurality of undiffused exhaust gas orifices; (i) the at least one diffused exhaust gas orifice and the at least one undiffused exhaust gas orifice may be spaced apart along the longitudinal axis of the vent housing; (j) the diffused exhaust gas orifice may be located at or proximate the first end of the vent housing; (k) the undiffused exhaust gas orifice may be located centrally between the first end of the vent housing and the second end of the vent housing; (l) the at least one diffused exhaust gas orifice may open in a lateral direction; (m) the at least one undiffused exhaust gas orifice may open in an oblique direction to the lateral direction, partially towards the second end of the vent housing; (n) the vent structure may comprise a diffuser member configured to diffuse and/or audibly muffle exhaust gas; (o) the diffuser member may be located in series with the at least one diffused exhaust gas orifice so as to require gas flowing through the at least one diffused exhaust gas orifice to flow through the diffuser member; (p) the vent structure may provide a diffused vent flow path through which exhaust gas is able to be vented through the diffuser member and the at least one diffused exhaust gas orifice; (q) the vent structure may provide an undiffused vent flow path through which exhaust gas is able to be vented through the at least one undiffused exhaust gas orifice; (r) the vent structure may be configured to allow exhaust gas to flow through the at least one undiffused exhaust gas orifice in the event the exhaust gas is unable to flow through the at least one diffused exhaust gas orifice; (s) the vent structure may be shaped to require the flow of exhaust gas to change direction to a greater extent to flow through the at least one undiffused exhaust gas orifice than through the diffused exhaust gas orifice; and/or (t) the vent structure may be shaped to require the flow of exhaust gas to change direction to flow through the undiffused exhaust gas orifice to a sufficient degree that a majority of the flow of exhaust gas passes through the diffuser member and through the diffused exhaust gas aperture unless the diffuser member becomes clogged.

In further examples of the above aspects, (a) the vent structure may comprise an exhaust gas orifice member comprising the at least one exhaust gas orifice; (b) the exhaust gas orifice member may comprise a plurality of exhaust gas orifices; (c) the exhaust gas orifice member may be configured to connect to the first housing member; (d) the exhaust gas orifice member may be formed in the shape of a ring; (e) the exhaust gas orifice member may comprise a plurality of exhaust gas orifices spaced apart around a circumference of the ring; (f) the at least one diffused exhaust gas orifice may be provided at or proximate a first end of the exhaust gas orifice member; (g) the at least one undiffused exhaust gas orifice may be provided at or proximate a second end of the exhaust gas orifice member opposite the first end of the exhaust gas orifice member; (h) the diffuser member may be retained in the vent structure by the exhaust gas orifice member; and/or (i) the diffuser member may be housed between the exhaust gas orifice member and the first housing member.

In further examples of the above aspects, (a) the moveable portion of the membrane may be supported radially inward from the membrane-facing surface, with respect to the longitudinal axis of the membrane; (b) the moveable portion of the membrane may be configured to move outwardly to restrict the vent flow of gas; (c) the moveable portion of the membrane may be configured to expand to move towards outwardly the membrane-facing surface; (d) the membrane-facing surface may be provided on an interior surface of the first housing member; (e) the membrane facing surface may be cylindrical or frustoconical; (f) the membrane support may comprise a baffle portion; (g) the baffle portion may be cylindrical; (h) the baffle portion may be concentric with the moveable portion of the membrane; (i) the baffle portion may be provided interior to the moveable portion of the membrane; (j) the baffle portion may have a first end connected to the moveable portion of the membrane at the first end of the membrane and a second end provided at or proximate the second end of the membrane; (k) the baffle portion may comprise an outwardly extending flange at the second end of the baffle portion; (l) the rounded surface at or proximate the entrance to the exhaust gas flow passage may be a fillet provided at the second end of the membrane support; (m) the rounded surface may be provided on the outwardly extending flange of the baffle portion of the membrane support; (n) the damping chamber may be partially defined by the baffle portion of the membrane support; (o) the damping chamber may be partially defined by the outwardly extending flange of the baffle portion; (p) the at least one projection may be provided on the first housing member; (q) the at least one projection may project radially inwardly from a cylindrical or conical surface of the first housing member; (r) the at least one projection may contact an outside surface of the membrane at the second end of the membrane; (s) the first housing member may comprise at least one intermediate exhaust gas orifice upstream of the diffuser member; (t) the diffuser member may be substantially cylindrically shaped and located over the intermediate exhaust gas orifice to diffuse and/or audibly muffle the vent flow of gas; (u) the second housing member may comprise a diffuser retaining portion; (v) the diffuser retaining portion may comprise a cylindrical sleeve configured to fit over the first housing member; (w) the first housing member may be substantially cylindrical with a second housing member connection portion at the second end of the first housing member and a diffuser support flange at the second end of the first housing member; (x) a diffuser may be retained in a diffuser channel between the diffuser support flange of the first housing member, the second housing member connection portion of the first housing member and the diffuser retaining portion of the second housing member; (y) the at least one exhaust gas orifice may be provided in the diffuser retaining portion of the second housing member or may be formed by a gap between the diffuser retaining portion of the second housing member and the diffuser support flange of the first housing member; and/or (z) a plurality of exhaust gas orifices may be provided in the diffuser retaining portion of the second housing member and/or at gaps between the diffuser retaining portion of the second housing member and the diffuser support flange of the first housing member.

Another aspect of one form of the present technology is a vent system configured to regulate a flow of pressurised breathable gas comprising a moveable membrane having an elongate shape that surrounds an axis of the membrane. The membrane may be generally cylindrical, frustroconical or the like.

Another aspect of one form of the present technology is a vent system configured to regulate a flow of pressurised breathable gas comprising a moveable membrane having a first end and second end spaced apart along a longitudinal axis, the membrane having a moveable portion between the first end and the second end surrounding the longitudinal axis, the vent system comprising a housing configured to limit movement of the second end of the membrane towards a membrane-facing surface.

Another aspect of one form of the present technology is a vent system configured to regulate a flow of pressurised breathable gas, the vent system comprising a membrane having a moveable portion, the vent system further comprising a damping structure configured to damp vibration of the moveable portion of the membrane.

Another aspect of one form of the present technology is a vent system configured to regulate a flow of pressurised breathable gas comprising a membrane having a moveable portion, the vent system comprising a vent housing configured to reduce vibration of the moveable portion of the membrane in modes of vibration higher than a first mode of vibration.

Another aspect of one form of the present technology is a vent system configured to regulate a flow of pressurised breathable gas comprising a membrane having a moveable portion having a first side and a second side, an exhaust gas flow passage provided on the first side of the moveable portion and a stagnant air cavity provided on the second side of the moveable portion.

Another aspect of one form of the present technology is a vent system configured to regulate a flow of pressurised breathable gas comprising a membrane having a moveable portion, and an exhaust gas flow passage comprising a region having a smaller cross-sectional area than adjacent regions of the exhaust gas flow passage.

Another aspect of one form of the present technology is a vent system configured to regulate a flow of pressurised breathable gas comprising a membrane having a first end and a second end spaced apart along a longitudinal axis, and a moveable portion surrounding the longitudinal axis between the first end and the second end, the moveable portion being provided radially inward, with respect to the longitudinal axis, of a membrane-facing surface, between which is an exhaust gas flow passage.

Another aspect of the present technology is directed to a patient interface comprising: a seal-forming structure configured to seal to a patient's face including at least around the patient's nares; a plenum chamber connected to the seal-forming structure; a positioning and stabilising structure to secure the patient interface on the patient in use; and a vent system according to any of the above aspects and/or examples of the technology.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Treatment Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

FIG. 2A shows an overview of a human respiratory system including the nasal and oral cavities, the larynx, vocal folds, oesophagus, trachea, bronchus, lung, alveolar sacs, heart and diaphragm.

4.3 Patient Interface

FIG. 3A shows a patient interface in the form of a nasal mask in accordance with one form of the present technology.

4.4 RPT Device

FIG. 4A shows an RPT device in accordance with one form of the present technology.

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Humidifier

4.6 Breathing Waveforms

Figure 6A:
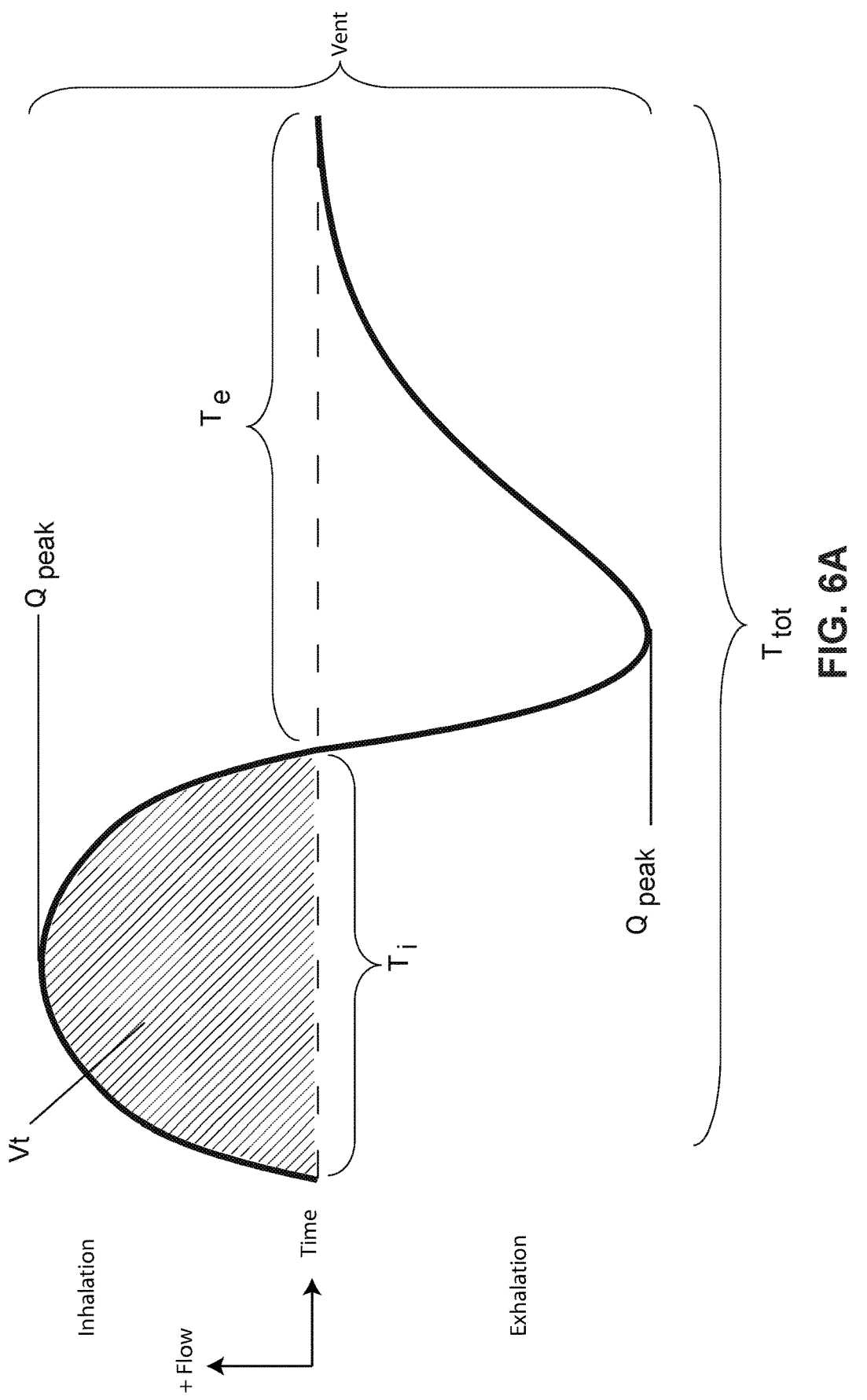

FIG. 6A shows a model typical breath waveform of a person while sleeping.

4.7 Screening, Diagnosis and Monitoring Systems

Figure 7A:
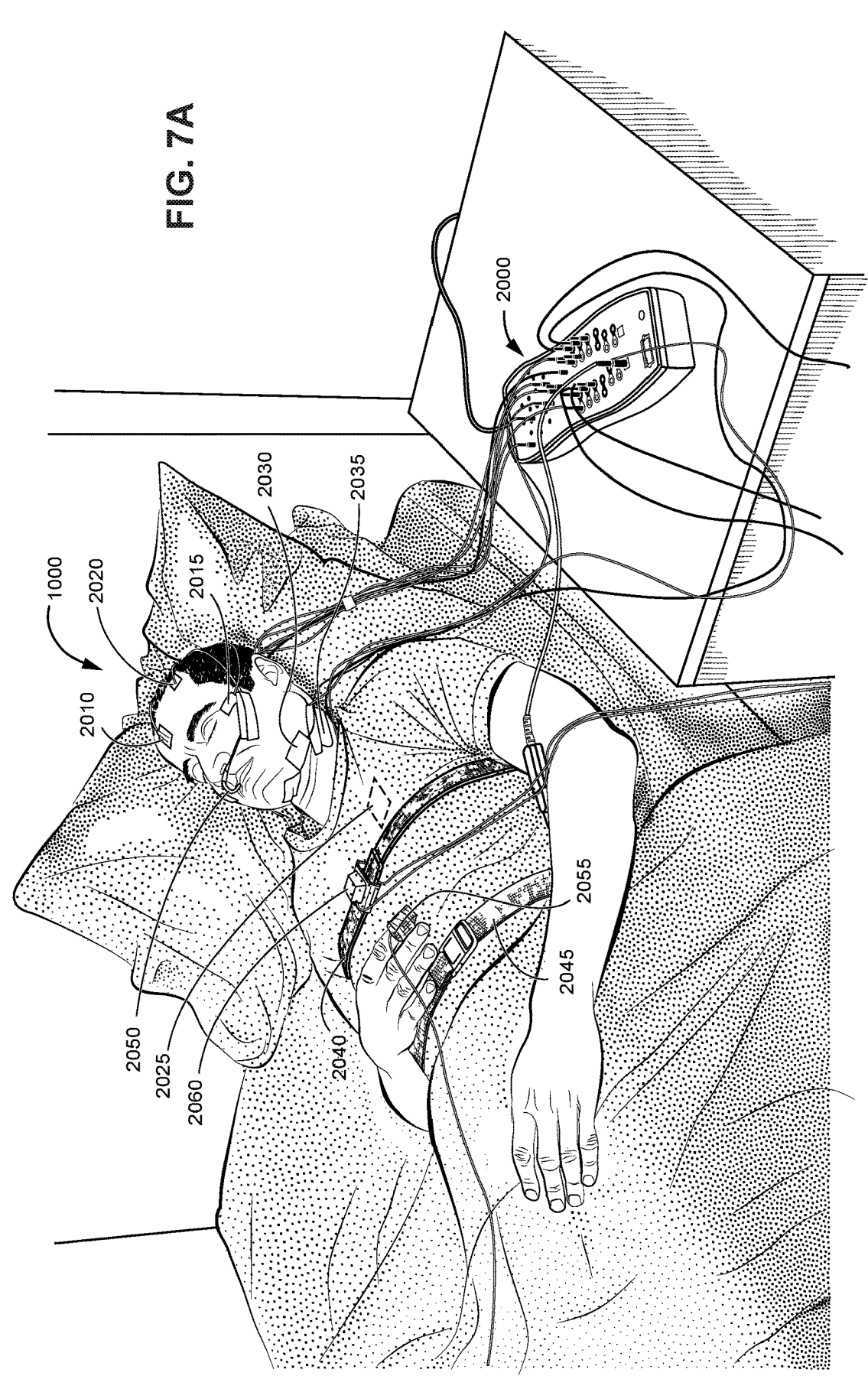

FIG. 7A shows a patient undergoing polysomnography (PSG). The patient is sleeping in a supine sleeping position.

Figure 7B:
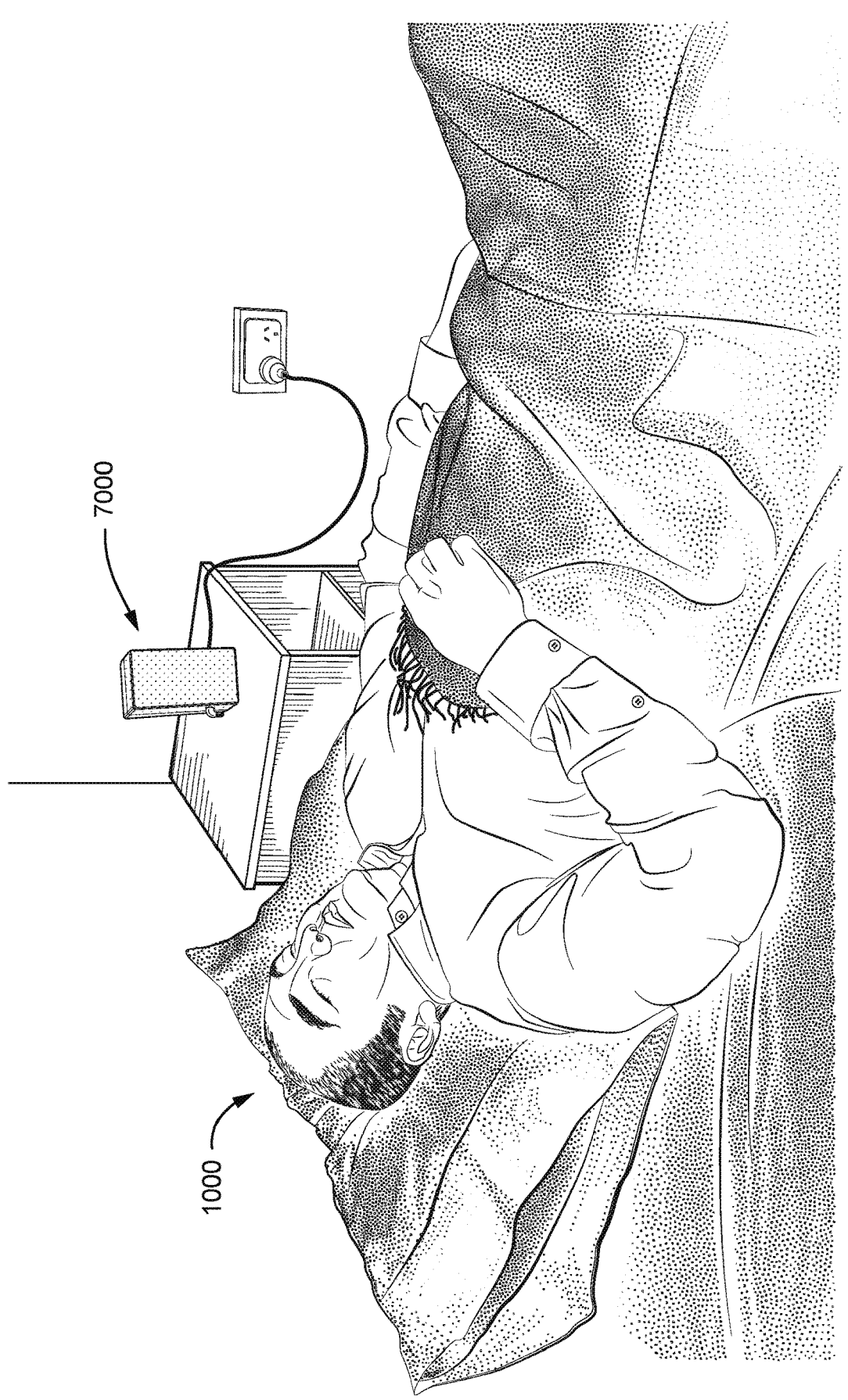

FIG. 7B shows a monitoring apparatus for monitoring the condition of a patient. The patient is sleeping in a supine sleeping position.

4.8 Vent System

Figure 8:
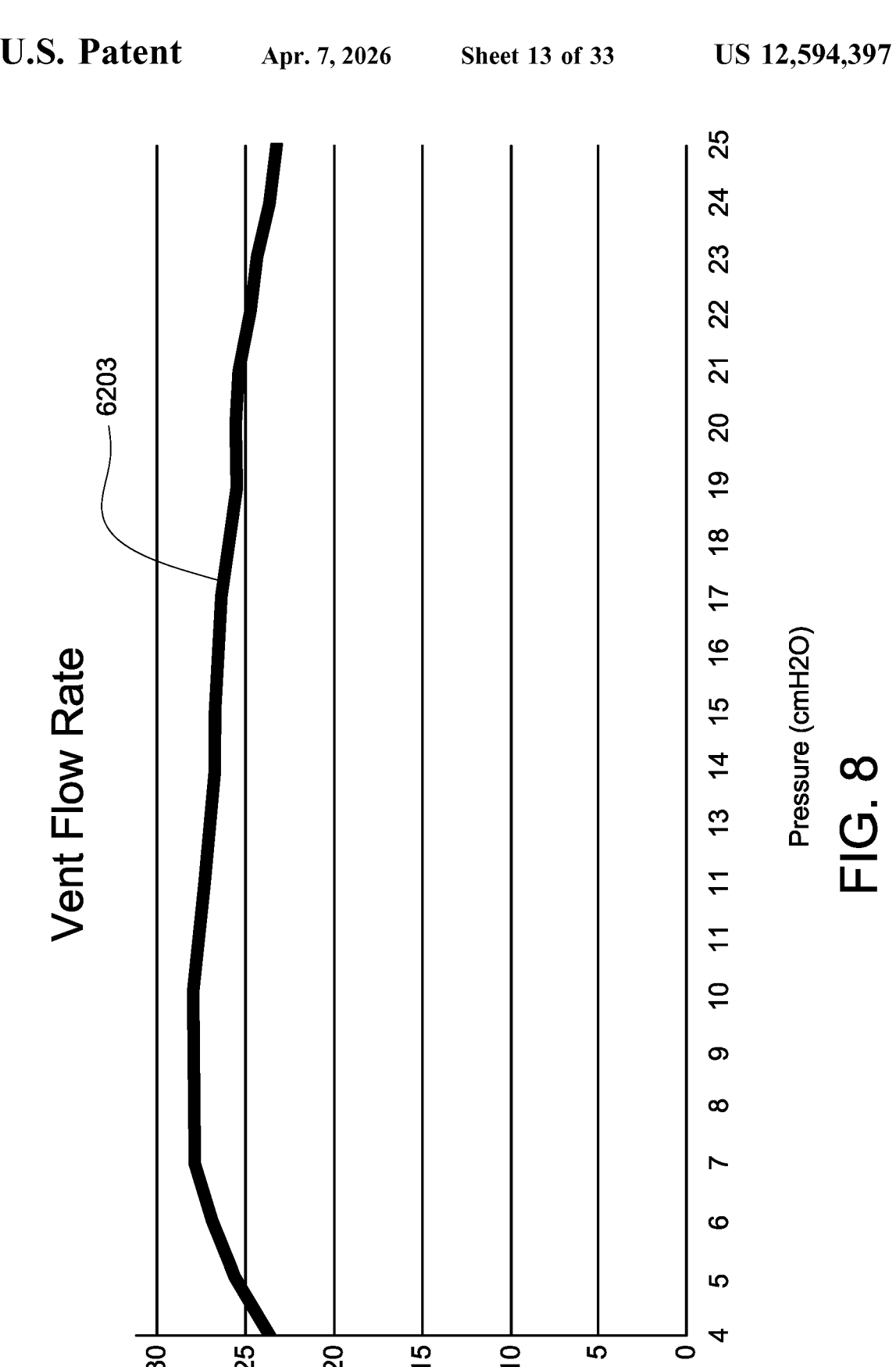

FIG. 8 shows a plot of flow rate of vent flow of gas through a vent system 3400 according to one example of the present technology, across a range of therapy pressures.

Figure 9A:
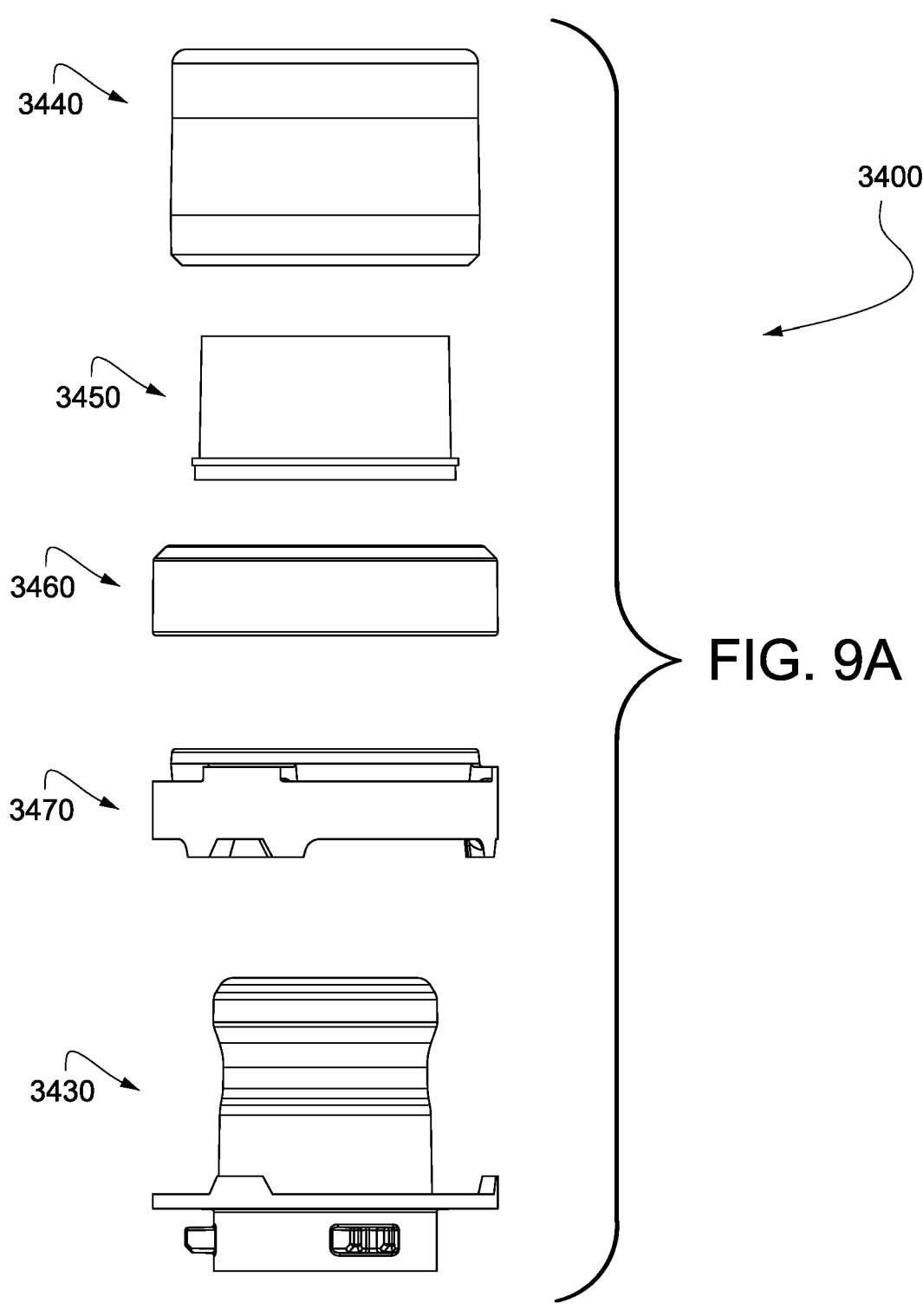

FIG. 9A shows an exploded view illustration of a vent system 3400 according to one example of the present technology.

Figure 9B:
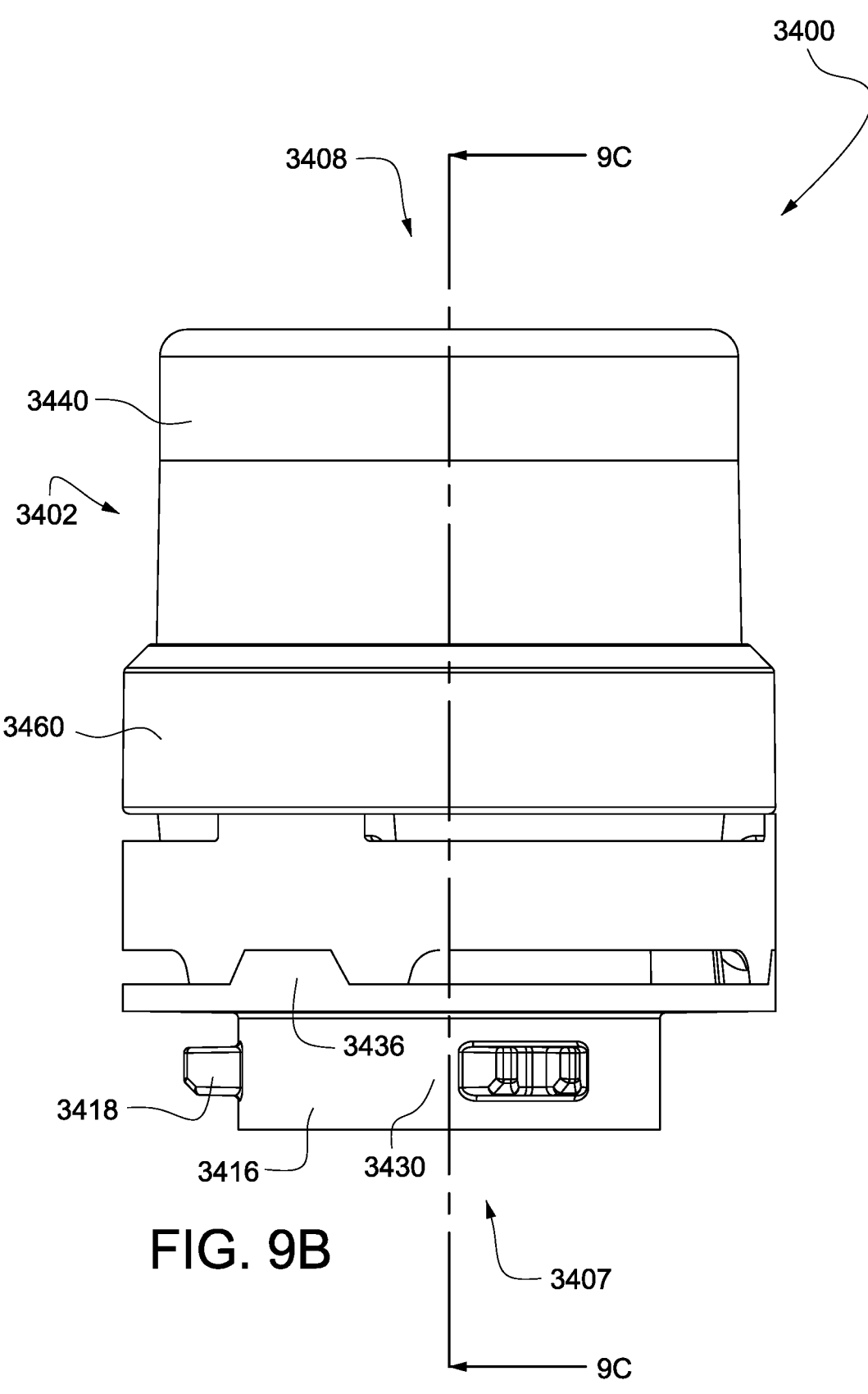

FIG. 9B shows a side view illustration of the vent system 3400 shown in FIG. 9A.

Figure 9C:
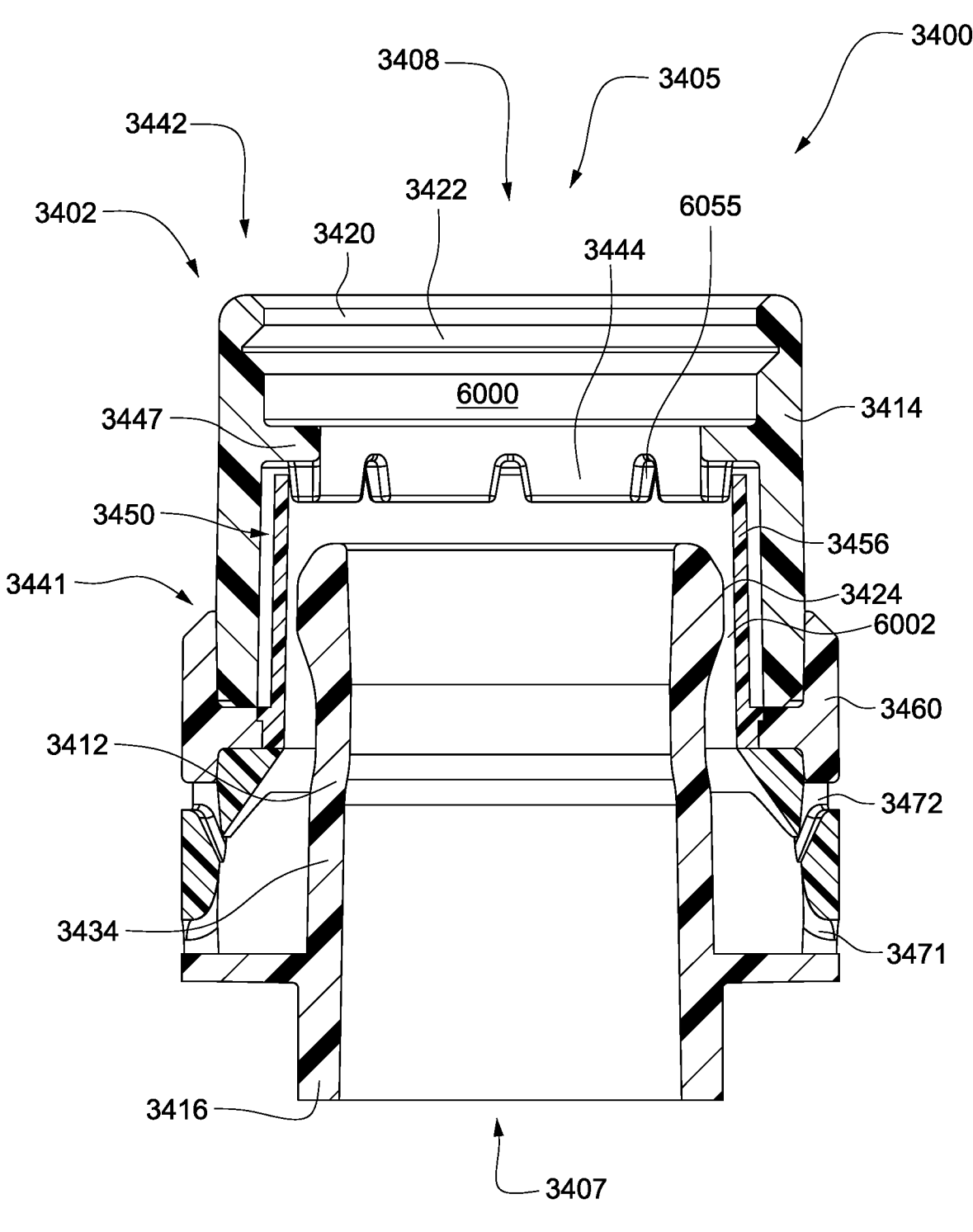

FIG. 9C shows a cross-section view illustration of the vent system 3400 shown in FIG. 9A.

Figure 9D:
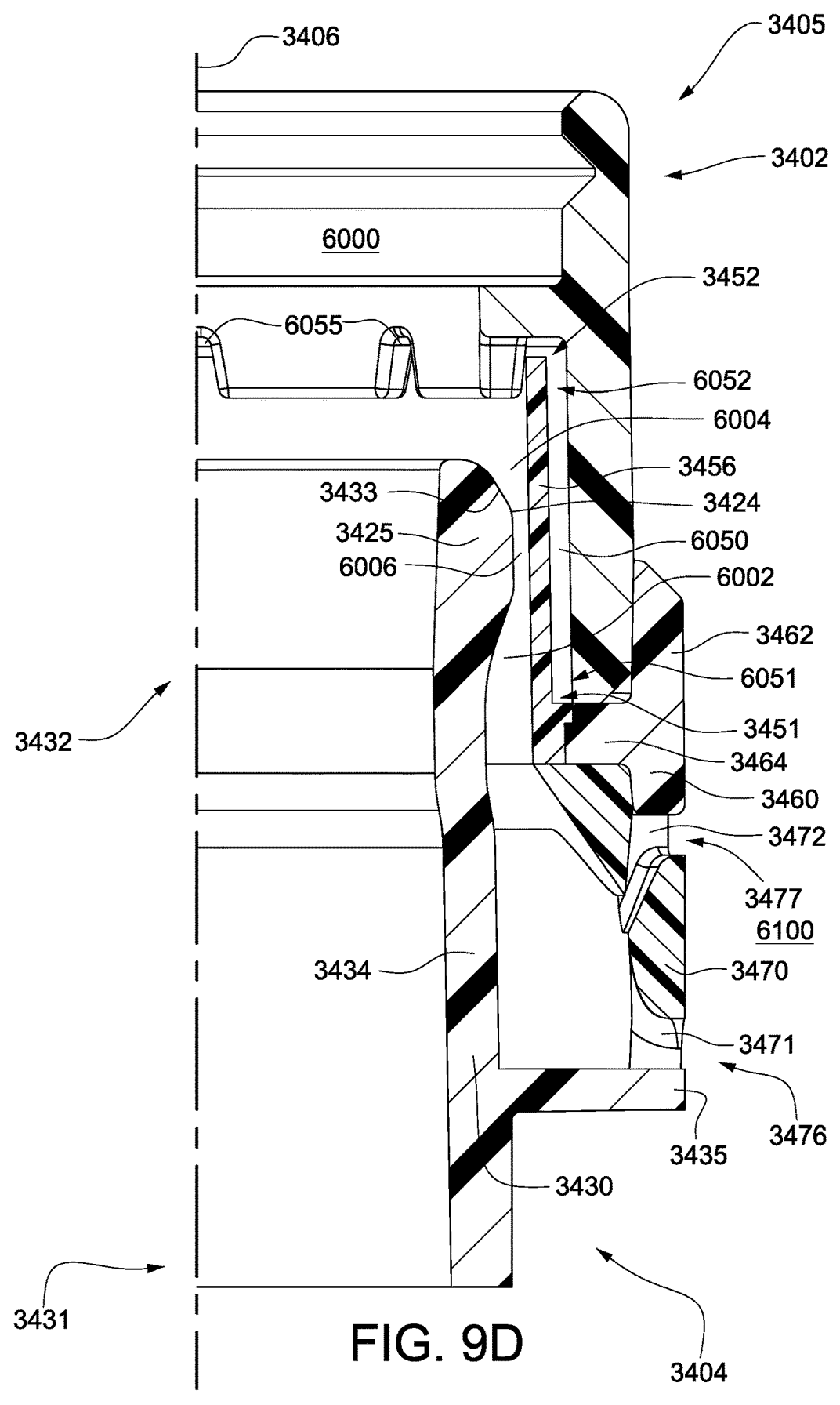

FIG. 9D shows another cross-section view illustration of the vent system 3400 shown in FIG. 9A.

Figure 9E:
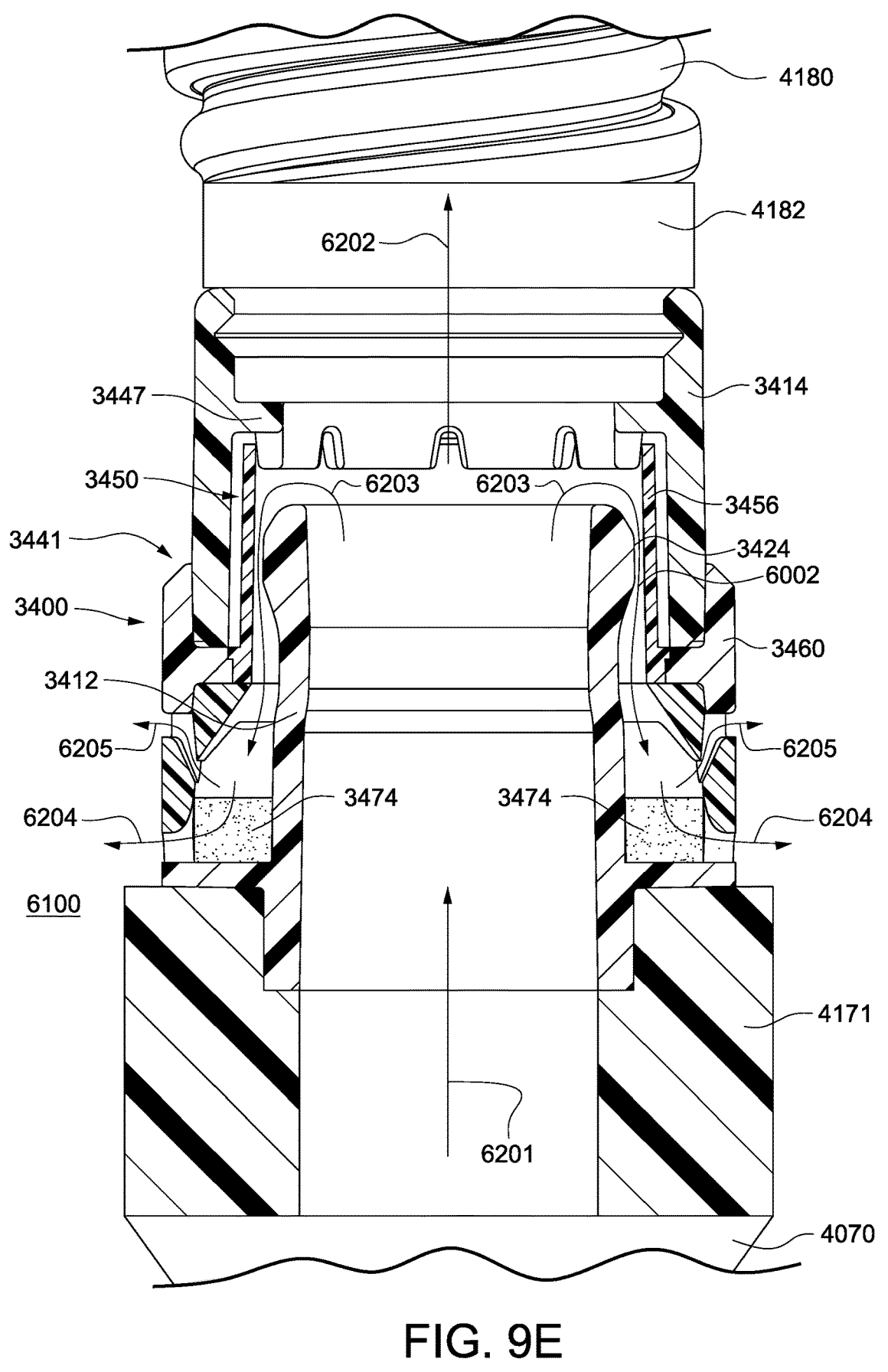

FIG. 9E shows another cross-section view illustration of the vent system 3400 shown in FIG. 9A when connected to upstream and downstream components.

Figure 9F:
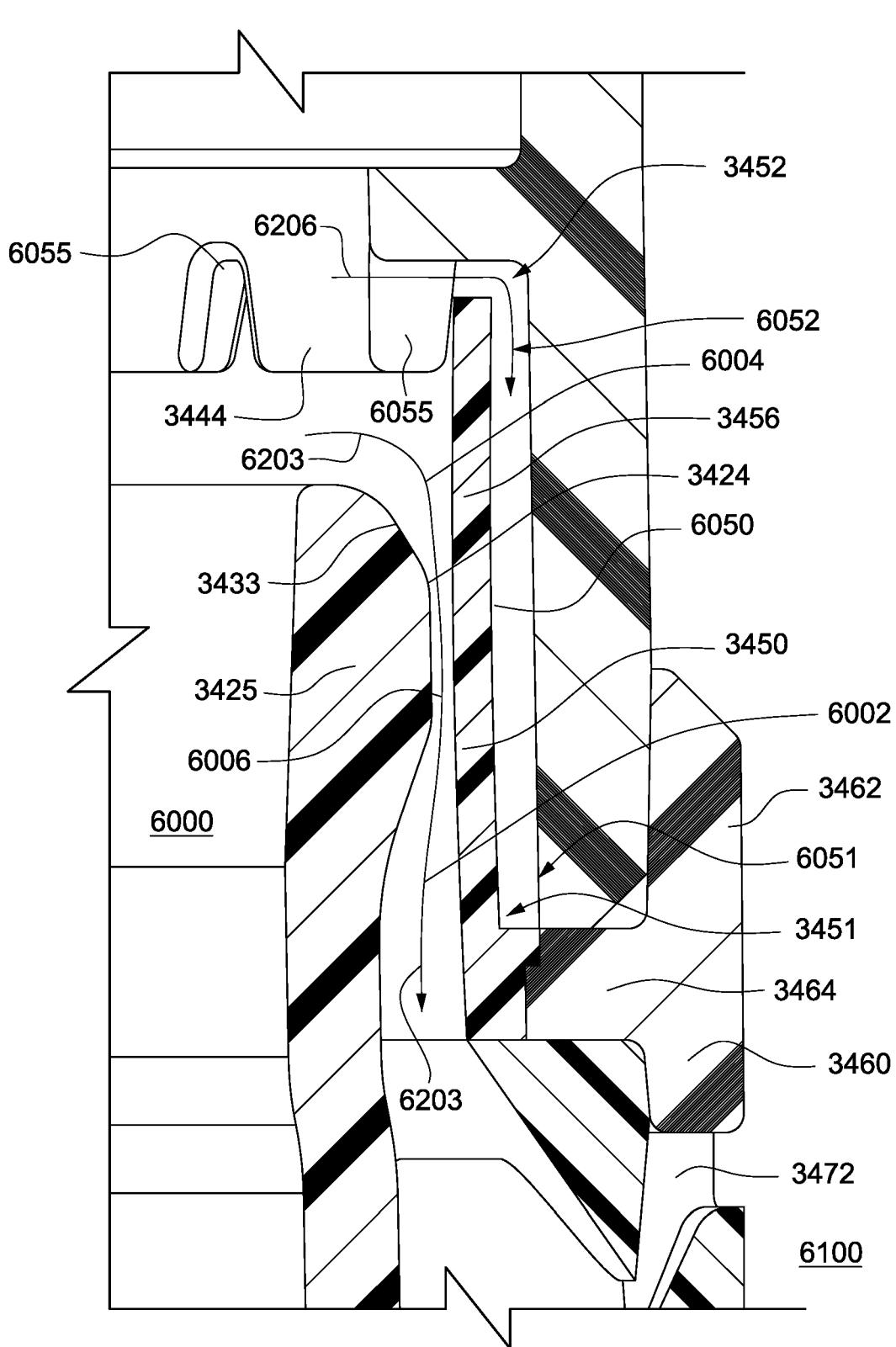

FIG. 9F shows another cross-section view illustration of a portion of the vent system 3400 shown in FIG. 9A in use during therapy with a low therapy pressure.

Figure 9G:
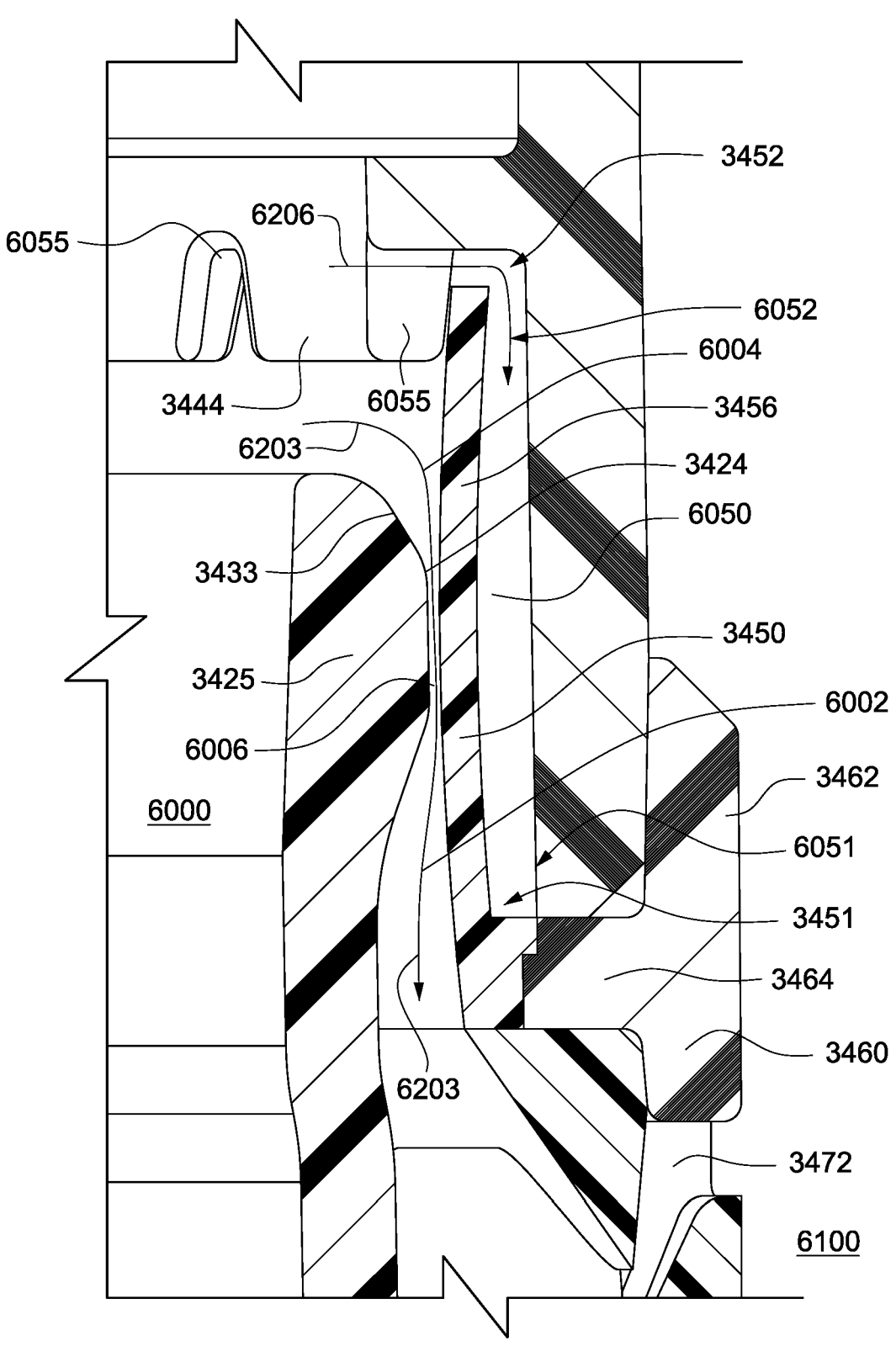

FIG. 9G shows another cross-section view illustration of a portion of the vent system 3400 shown in FIG. 9A in use during therapy with a high therapy pressure.

Figure 10A:
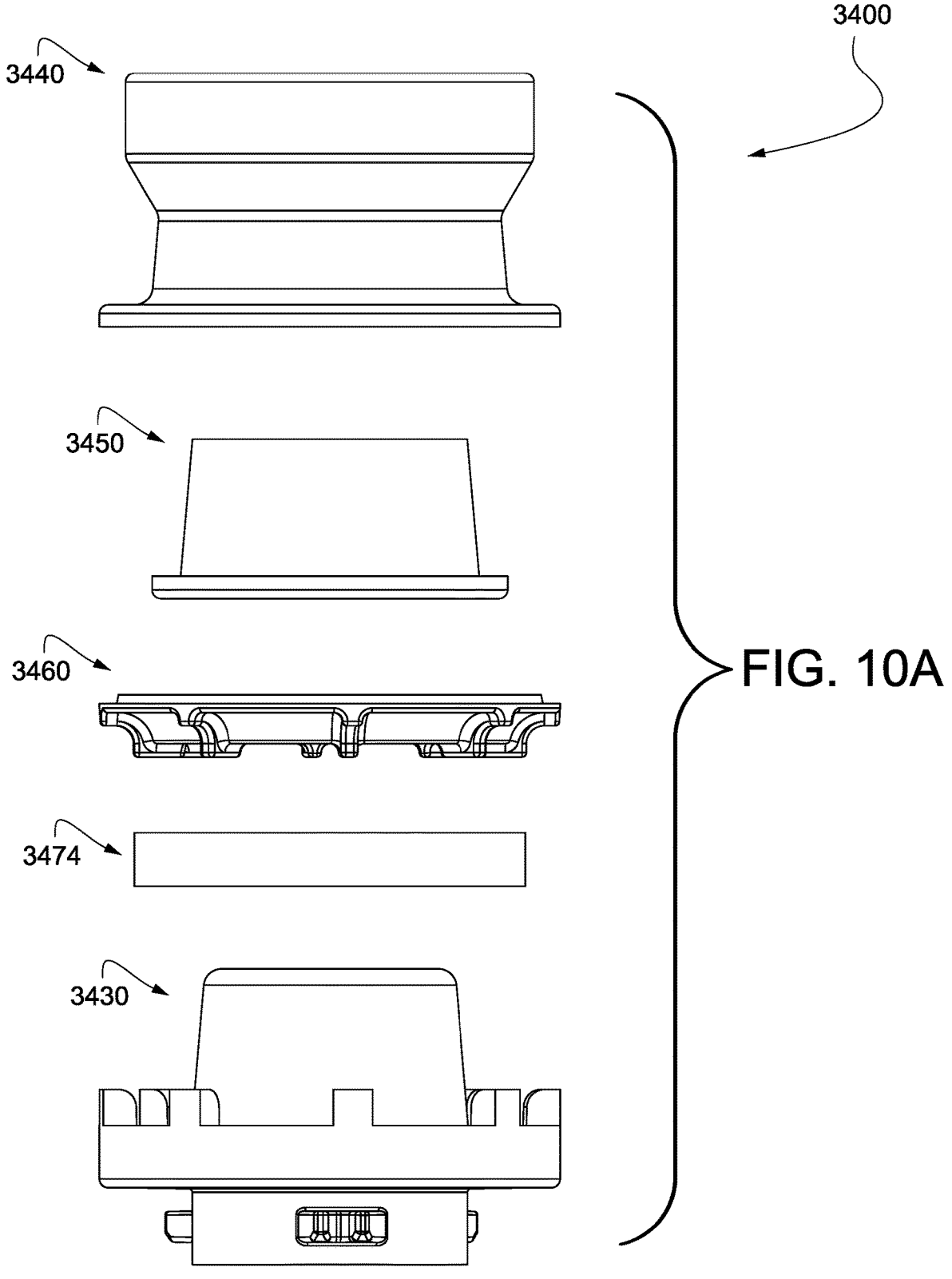

FIG. 10A shows an exploded view illustration of a vent system 3400 according to another example of the present technology.

Figure 10B:
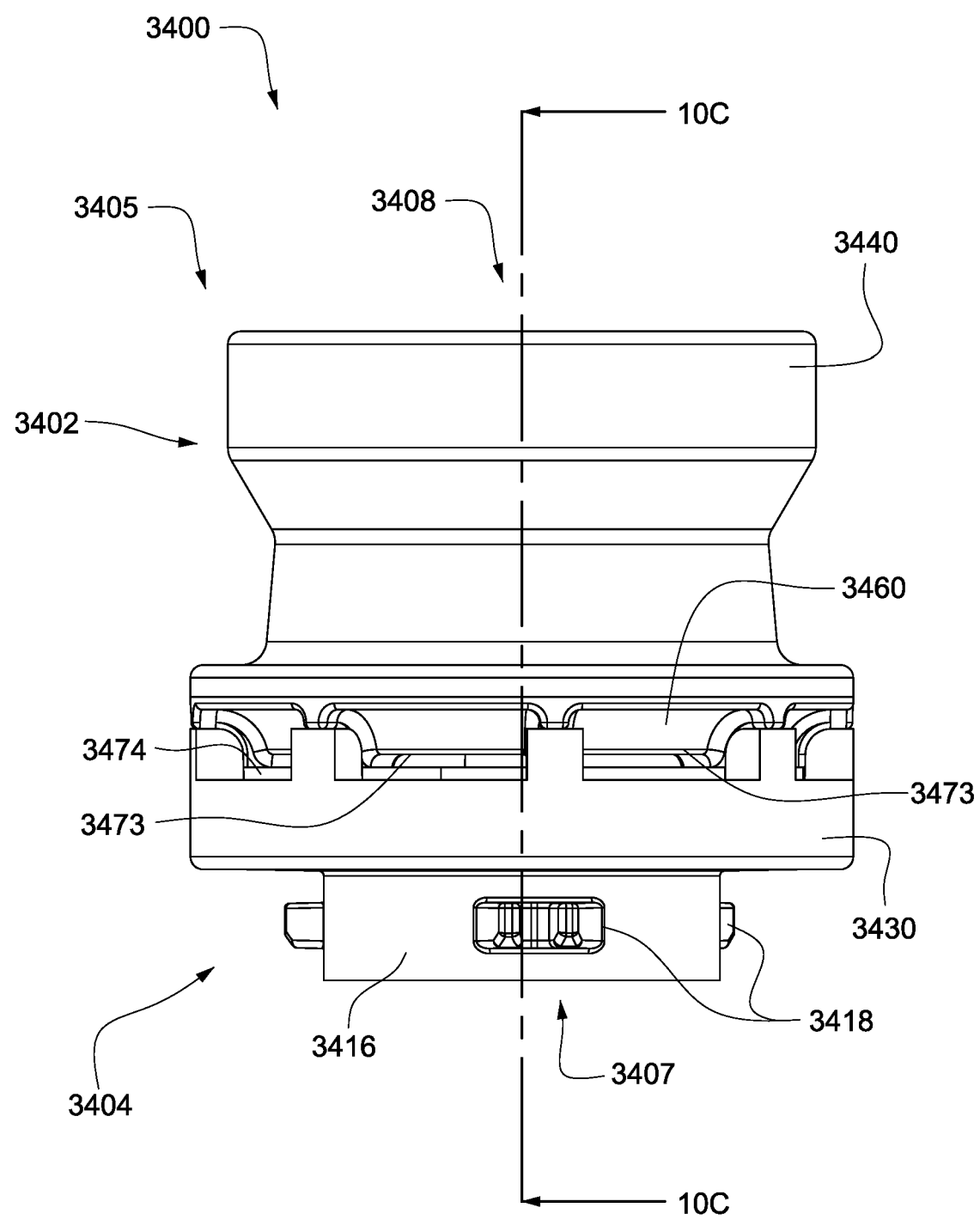

FIG. 10B shows a side view illustration of the vent system 3400 shown in FIG. 10A.

Figure 10C:
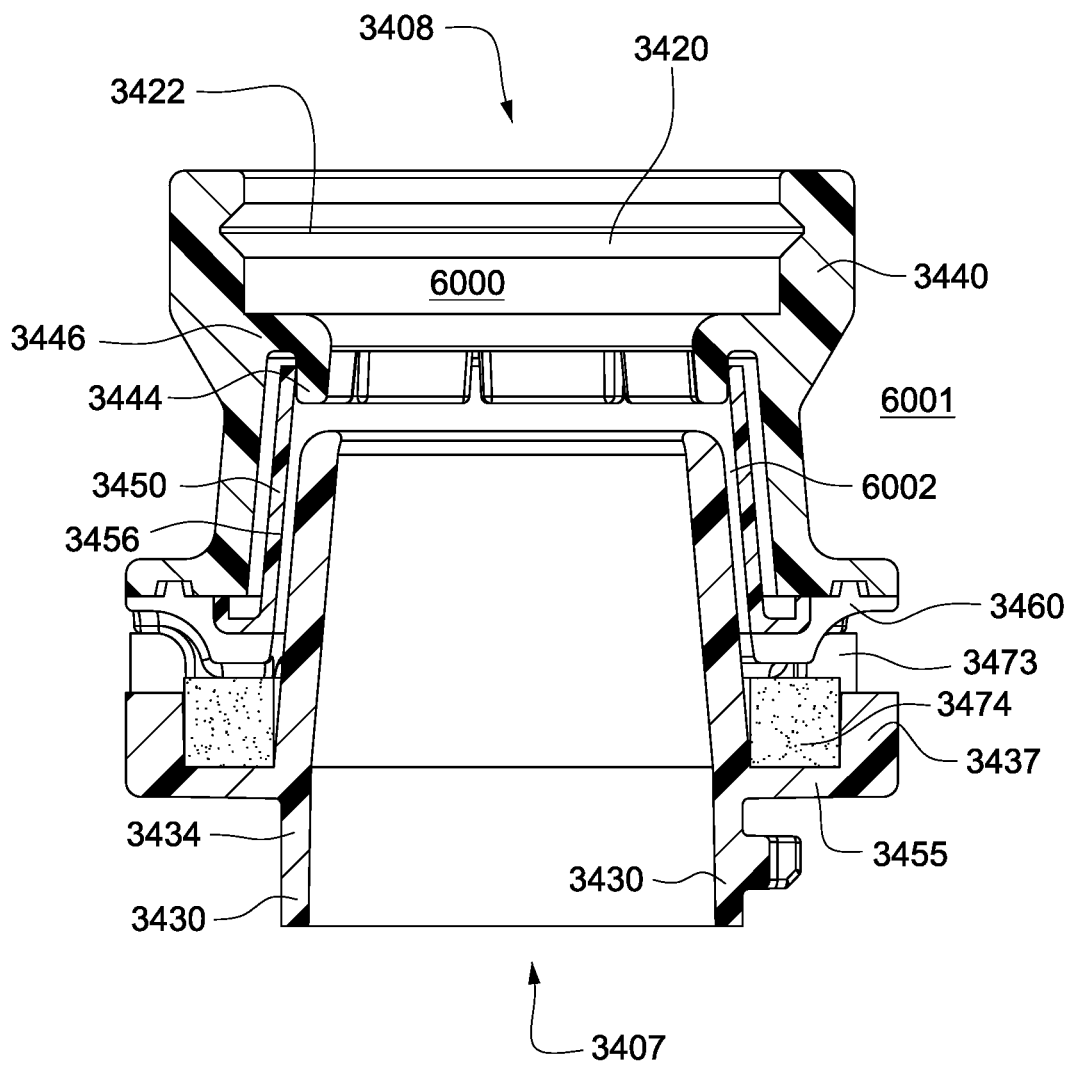

FIG. 10C shows a cross-section view illustration of the vent system 3400 shown in FIG. 10A.

Figure 10D:
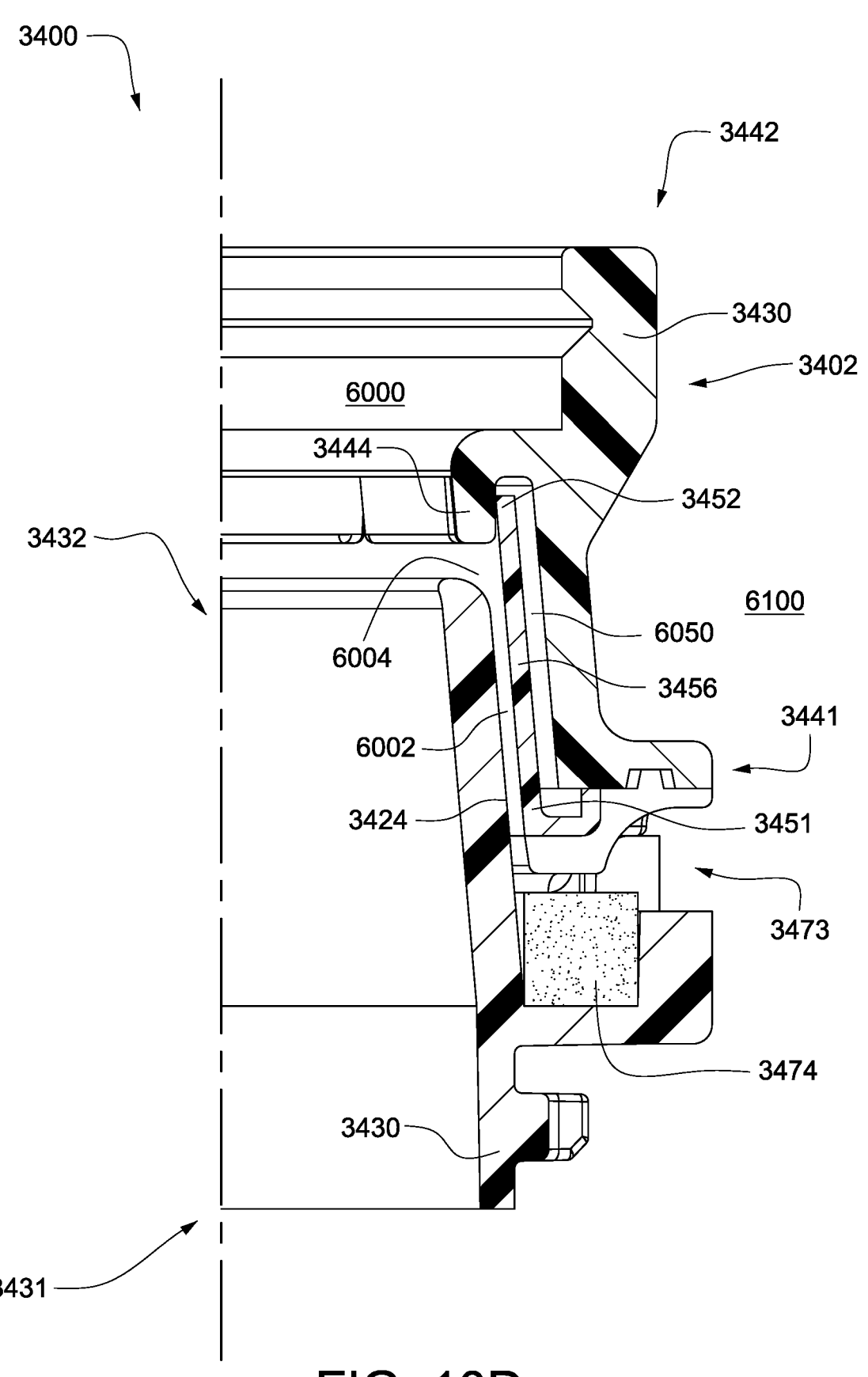

FIG. 10D shows another cross-section view illustration of the vent system 3400 shown in FIG. 10A.

Figure 11A:
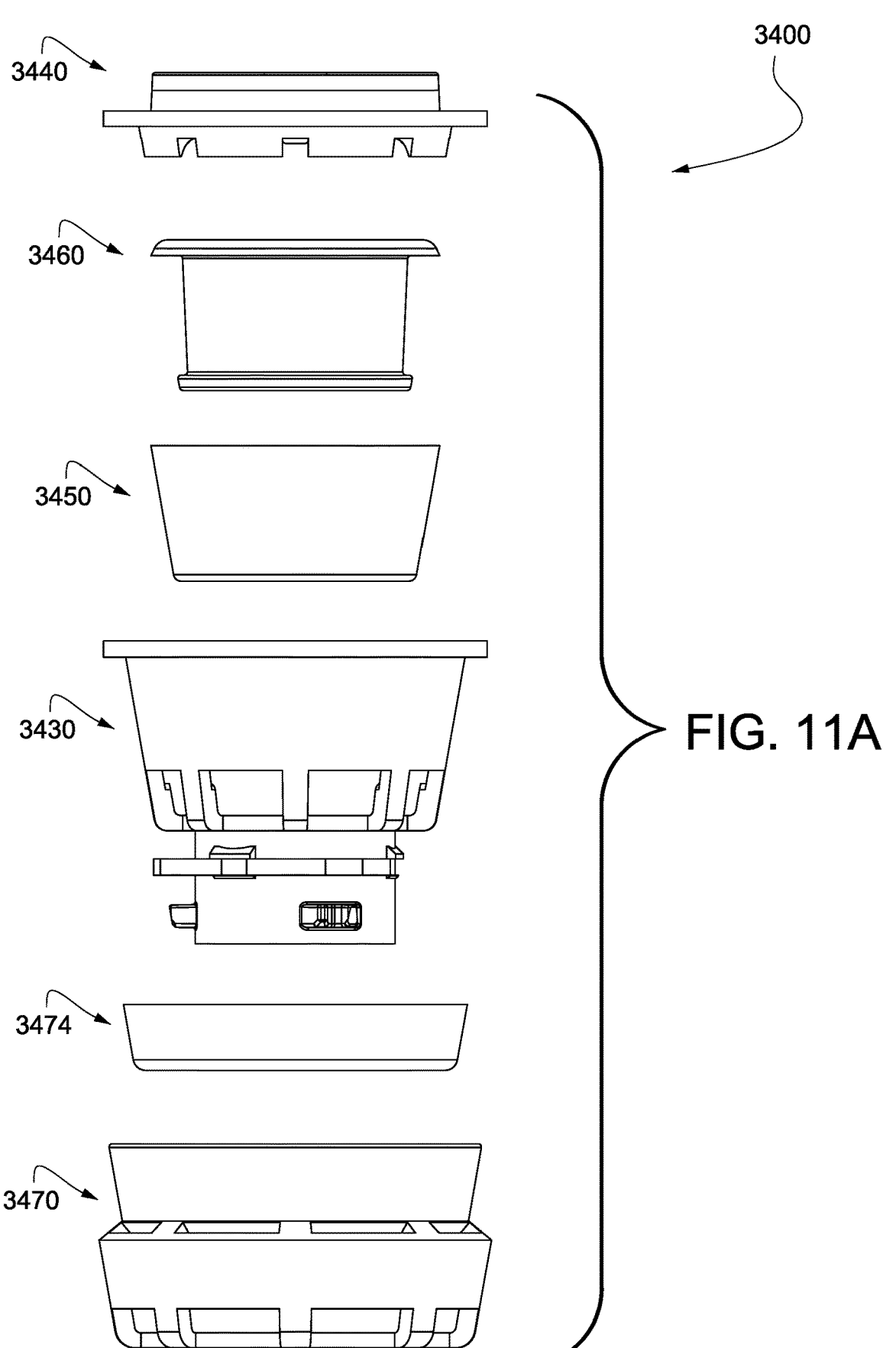

FIG. 11A shows an exploded view illustration of a vent system 3400 according to another example of the present technology.

Figure 11B:
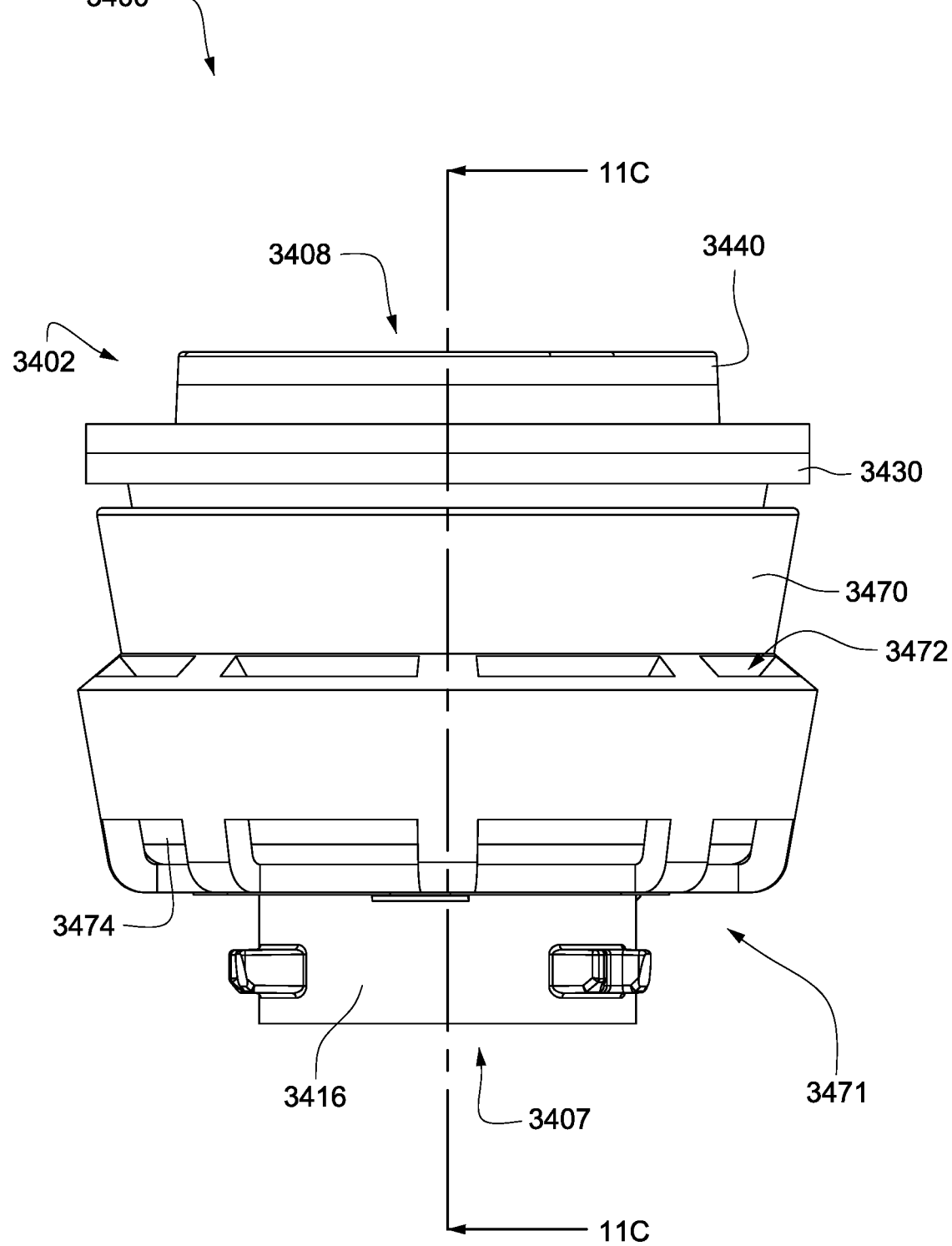

FIG. 11B shows a side view illustration of the vent system 3400 shown in FIG. 11A.

Figure 11C:
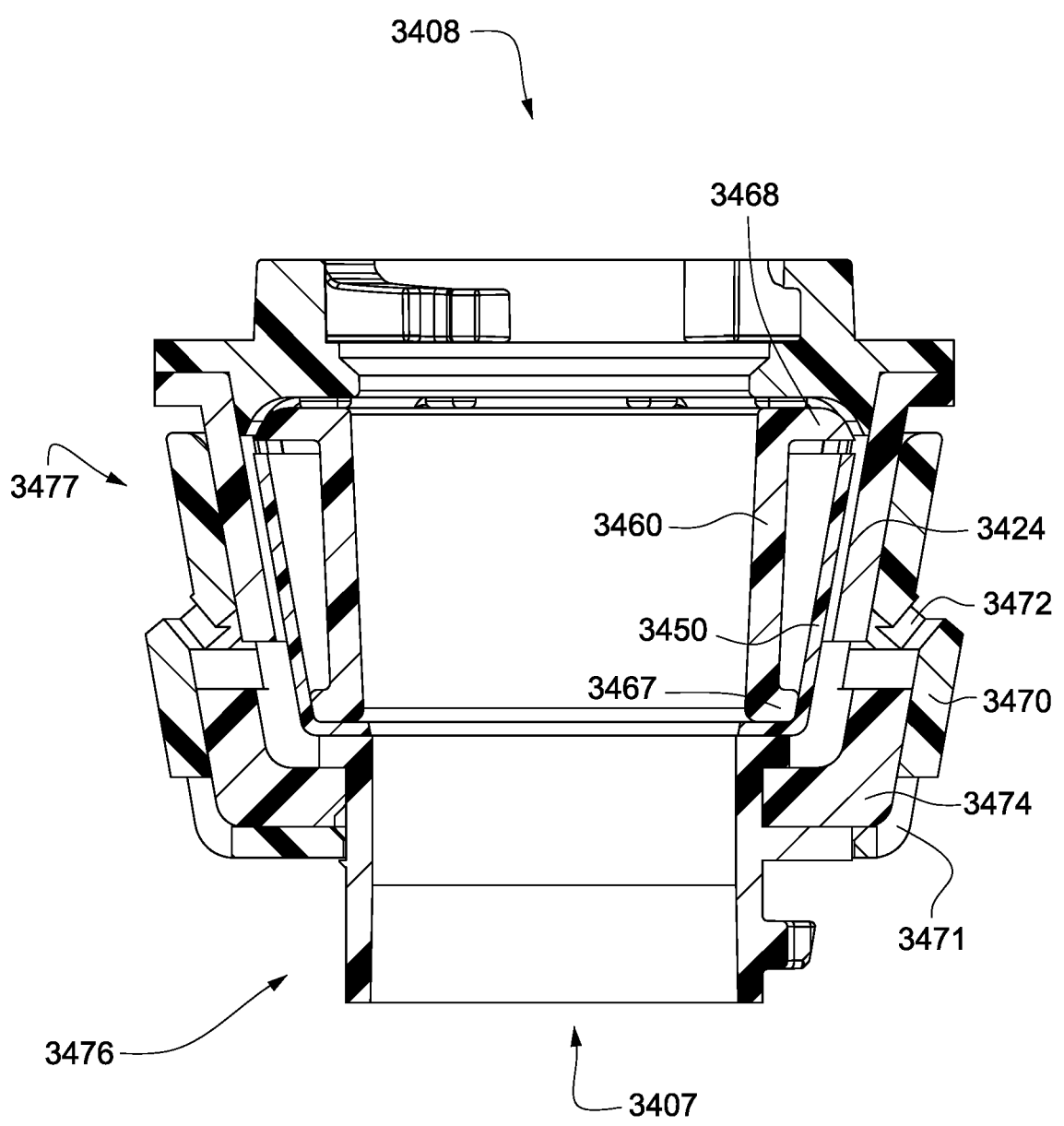

FIG. 11C shows a cross-section view illustration of the vent system 3400 shown in FIG. 11A.

Figure 11D:
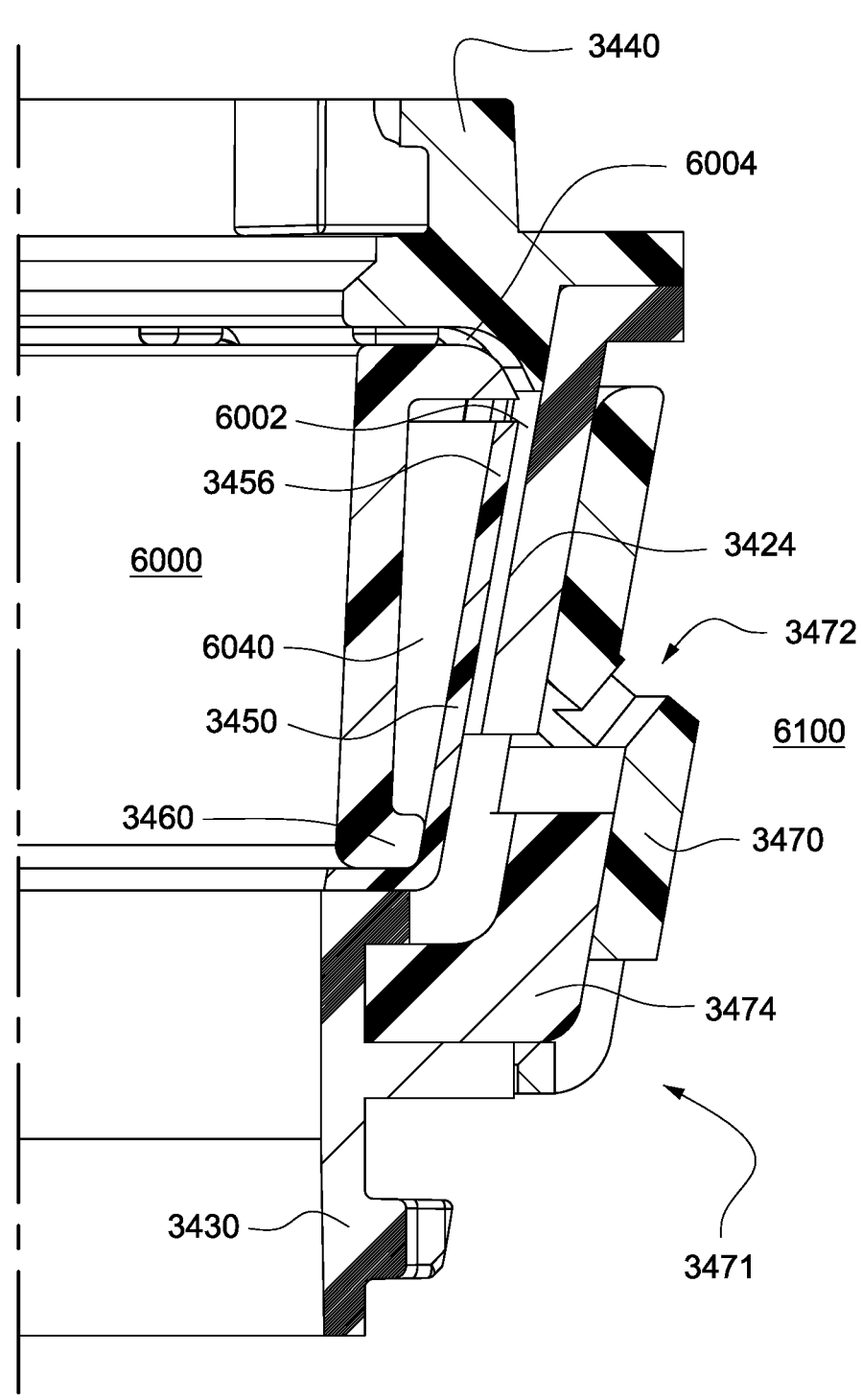

FIG. 11D shows another cross-section view illustration of the vent system 3400 shown in FIG. 11A.

Figure 12A:
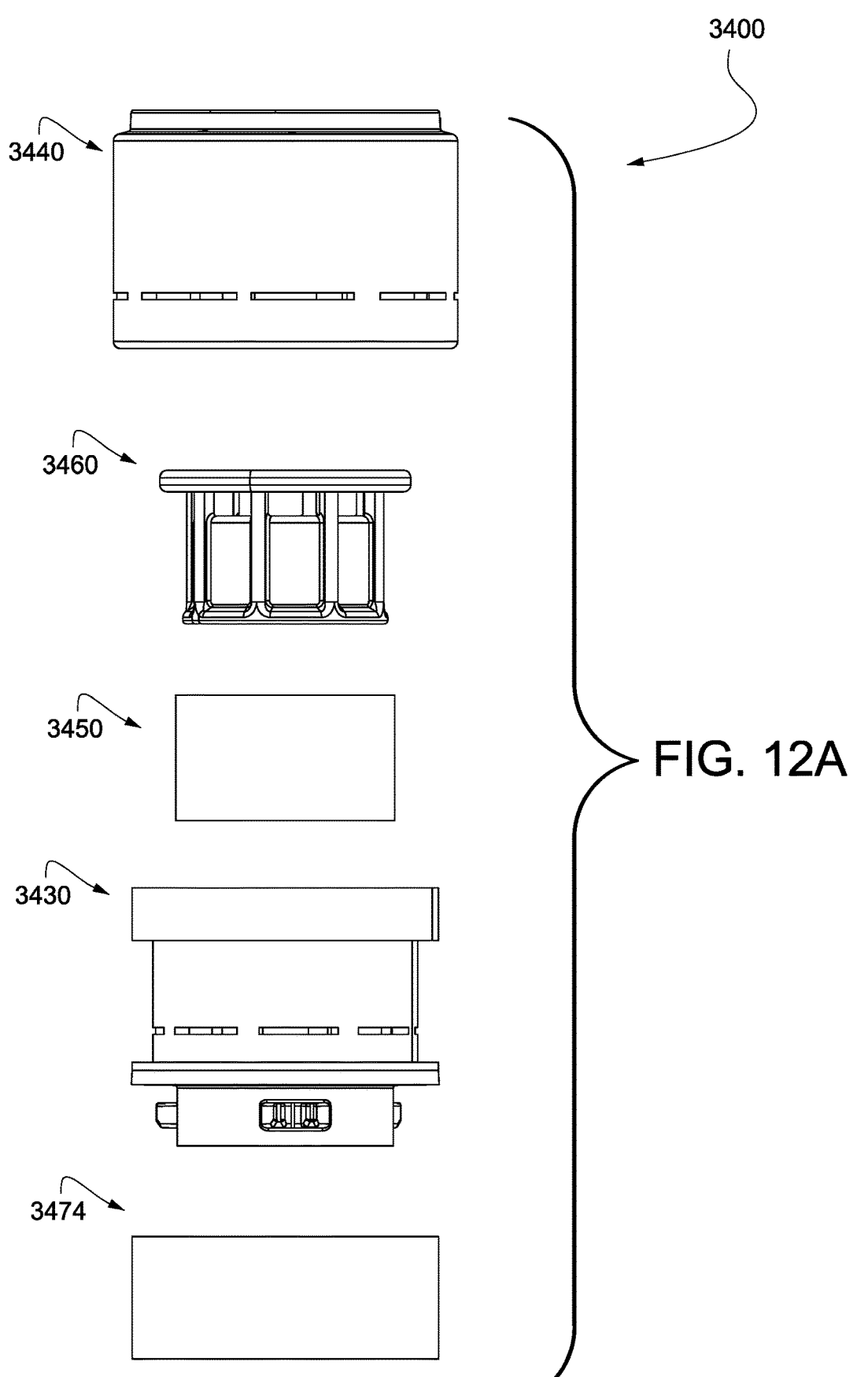

FIG. 12A shows an exploded view illustration of a vent system 3400 according to another example of the present technology.

Figure 12B:
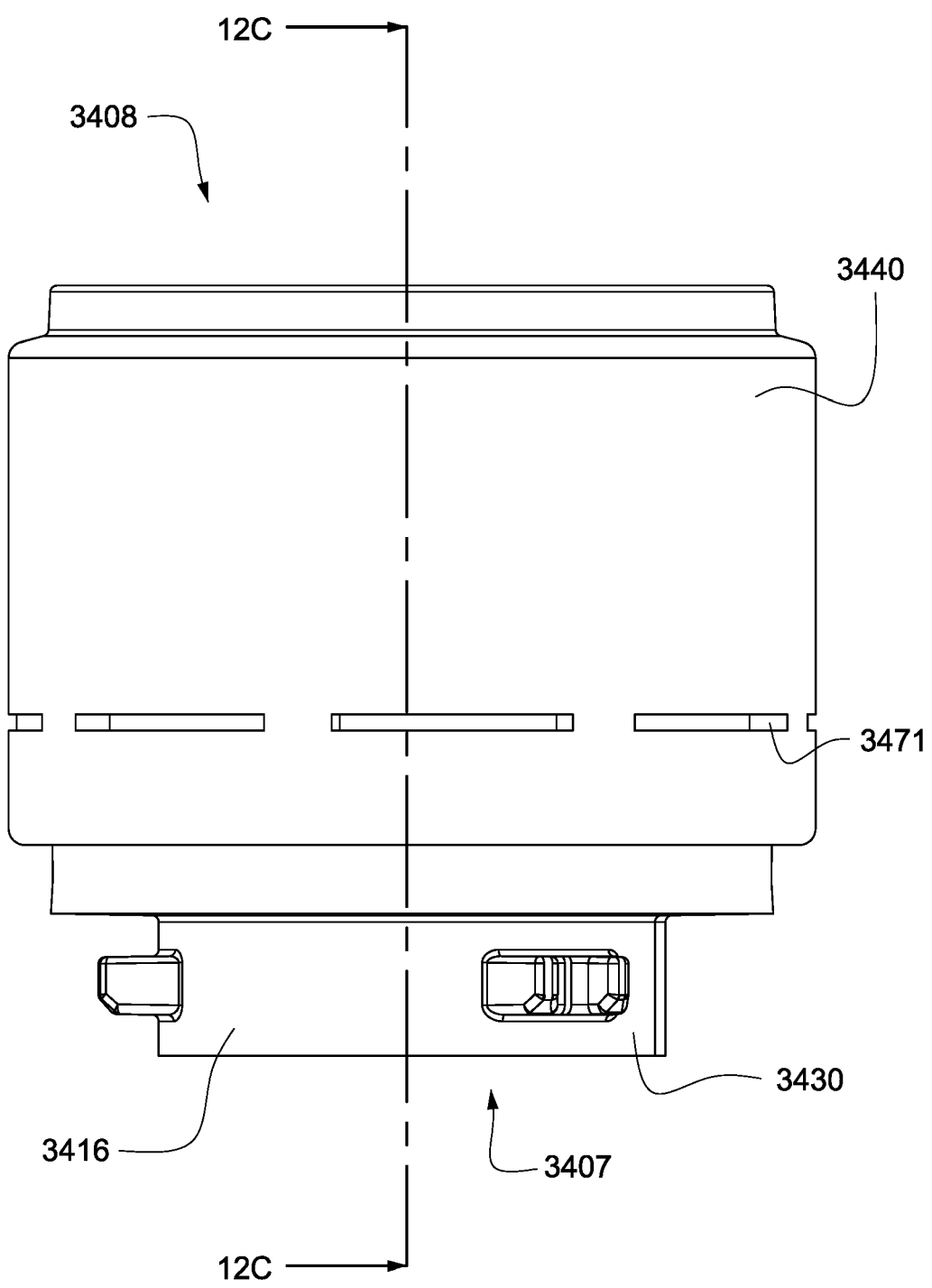

FIG. 12B shows a side view illustration of the vent system 3400 shown in FIG. 12A.

Figure 12C:
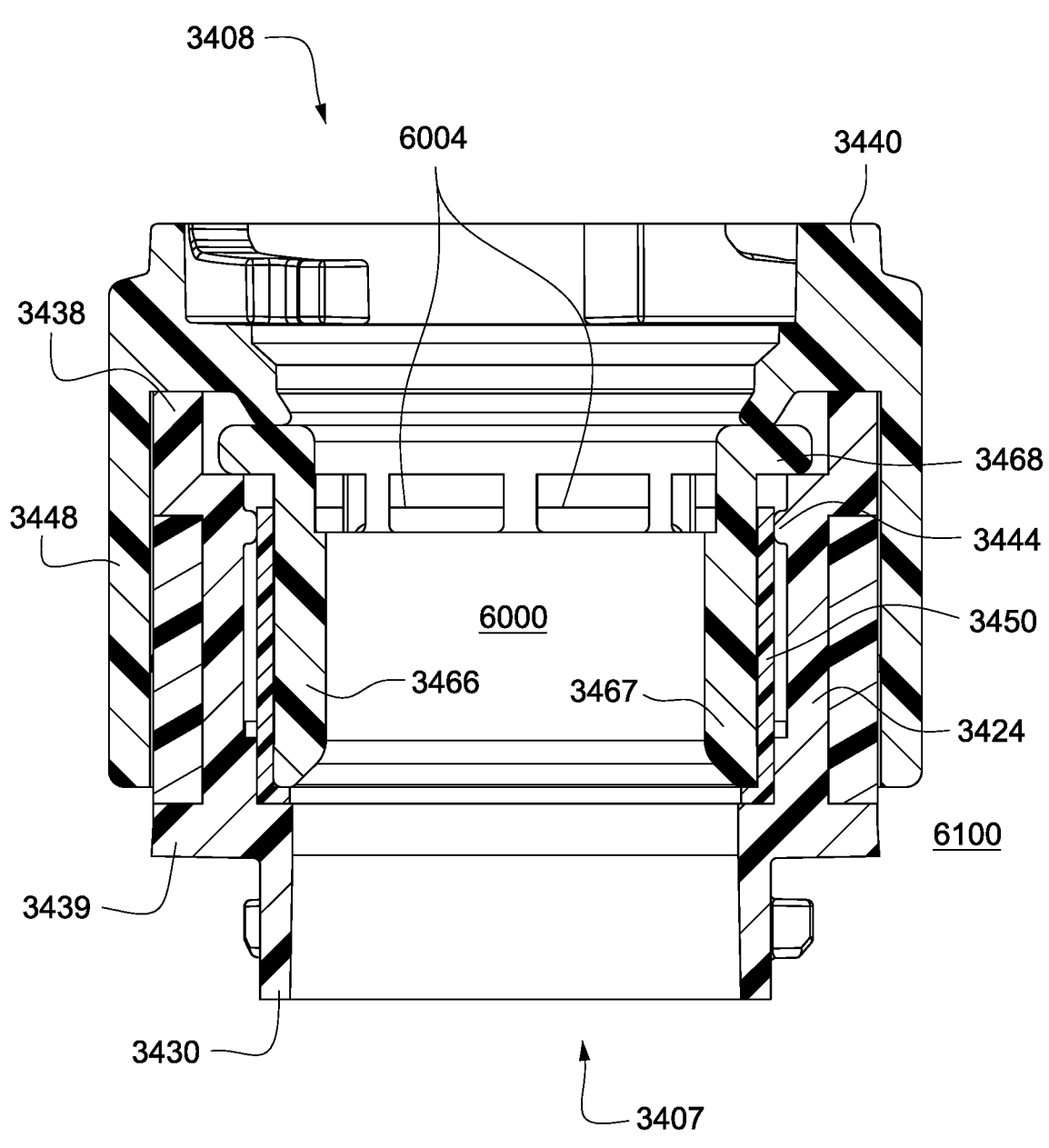

FIG. 12C shows a cross-section view illustration of the vent system 3400 shown in FIG. 12A.

Figure 12D:
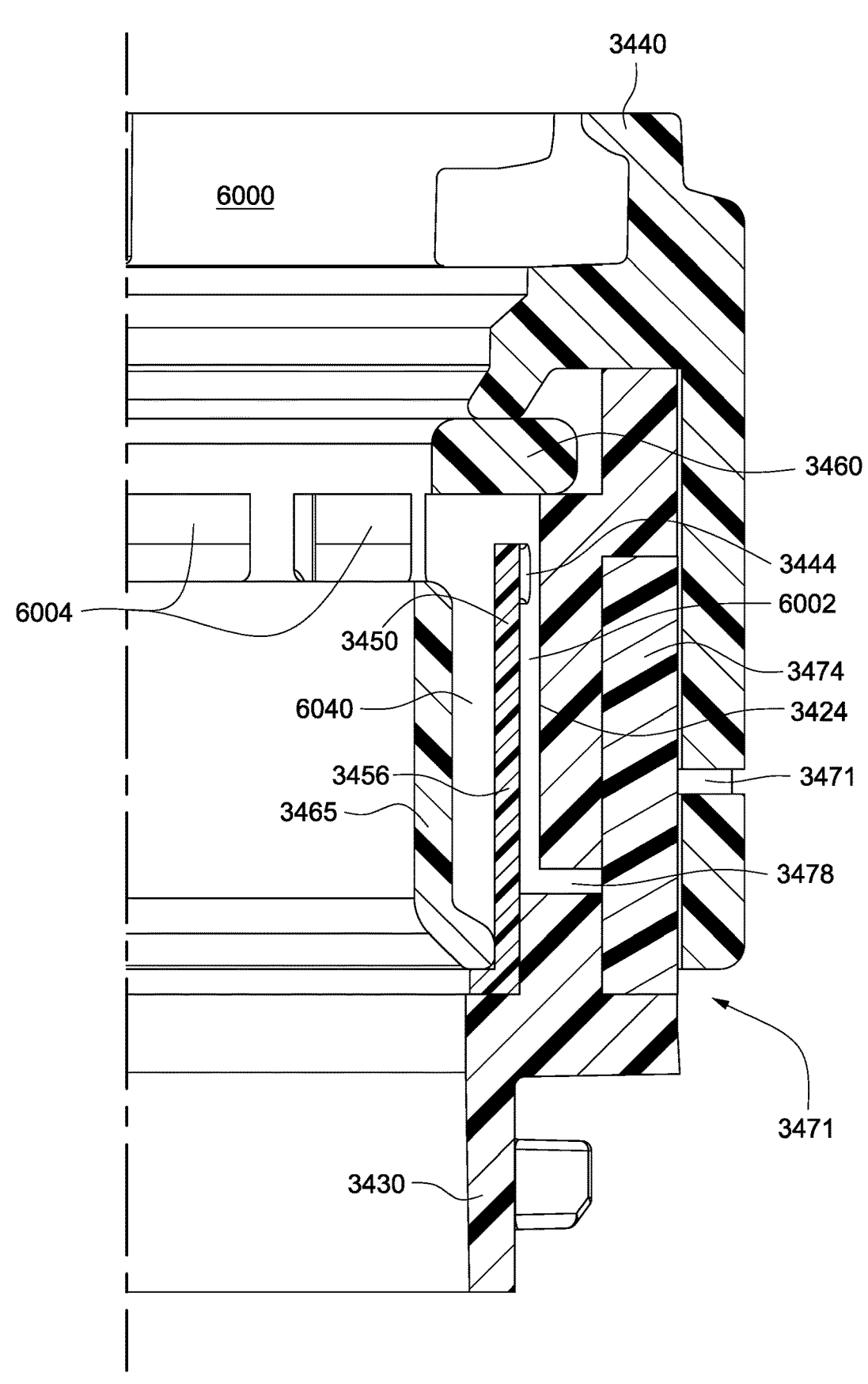

FIG. 12D shows another cross-section view illustration of the vent system 3400 shown in FIG. 12A.

Figure 13:
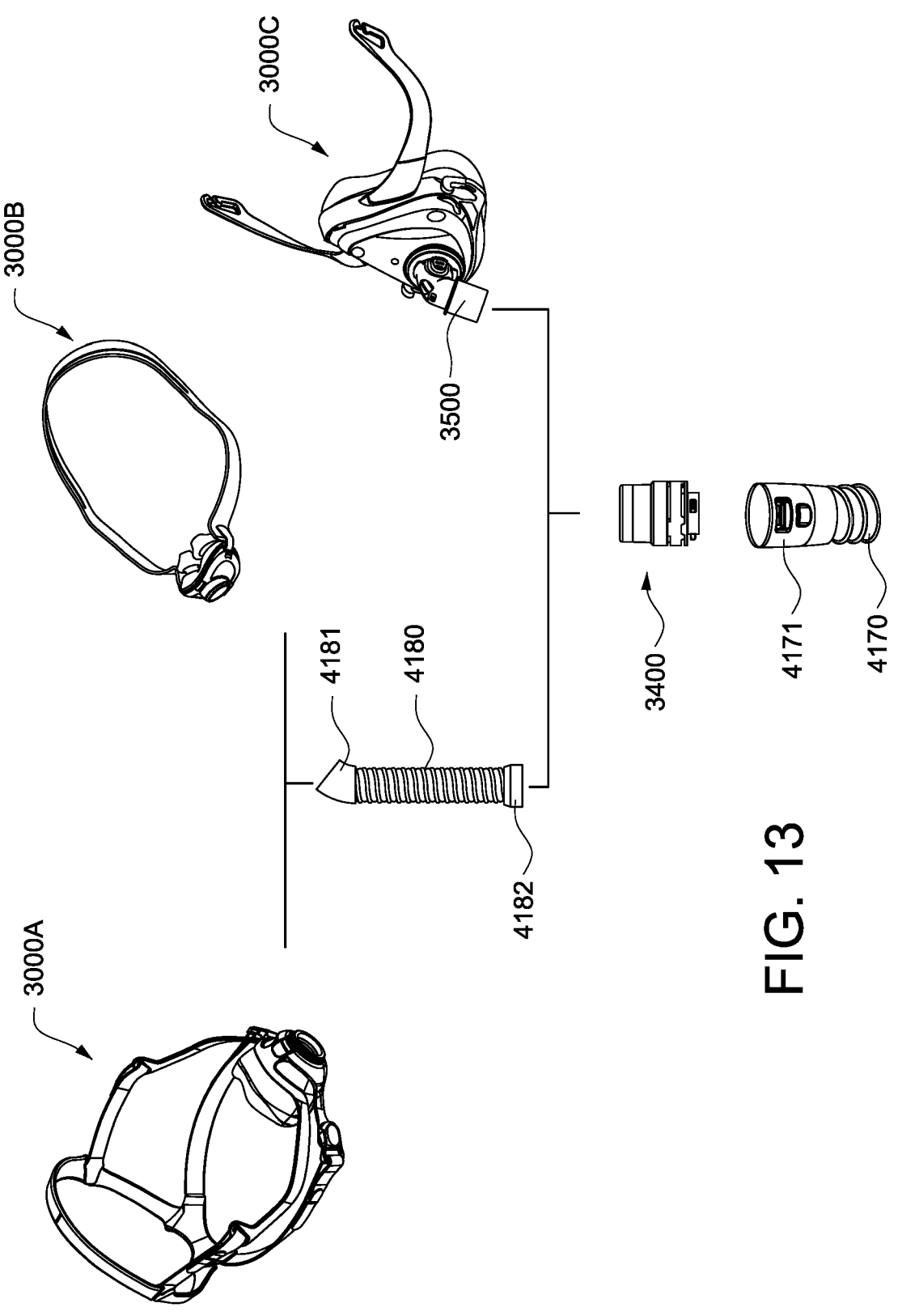

FIG. 13 depicts a schematic showing options for using vent systems of the present technology with various patient interfaces.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 THERAPY

In one form, the present technology comprises a method for treating a respiratory disorder comprising the step of applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 TREATMENT SYSTEMS

In one form, the present technology comprises an apparatus or device for treating a respiratory disorder. The apparatus or device may comprise an RPT device 4000 for supplying pressurised air to the patient 1000 via an air circuit 4170 to a patient interface 3000.

5.3 PATIENT INTERFACE

A non-invasive patient interface 3000 in accordance with one aspect of the present technology comprises the following functional aspects: a seal-forming structure 3100, a plenum chamber 3200, a positioning and stabilising structure 3300, a vent system 3400, one form of connection port 3600 for connection to air circuit 4170, and a forehead support 3700. In some forms, a functional aspect may be provided by one or more physical components. In some forms, one physical component may provide one or more functional aspects. In use, the seal-forming structure 3100 is arranged to surround an entrance to the airways of the patient so as to facilitate the supply of air at positive pressure to the airways.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form, the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example, the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form the seal-forming structure of the non-invasive patient interface 3000 comprises a pair of nasal puffs, or nasal pillows, each nasal puff or nasal pillow being con-structed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

5.3.3 Positioning and Stabilising Structure

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In certain forms of the present technology, a system is provided comprising more than one positioning and stabi-lizing structure 3300, each being configured to provide a retaining force to correspond to a different size and/or shape range. For example the system may comprise one form of positioning and stabilizing structure 3300 suitable for a large sized head, but not a small sized head, and another. suitable for a small sized head, but not a large sized head.

5.3.4 Vent System

In one form, the patient interface 3000 includes a vent system 3400 constructed and arranged to allow for the washout of exhaled gases, e.g. carbon dioxide. The patient interface 3000 may be configured for providing respiratory therapy to a patient with a therapy flow of gas pressured above ambient pressure within a therapeutic pressure range by the respiratory pressure therapy device 4000. The vent system 3400 may alternatively be identified as a vent structure, vent assembly and/or vent.

In certain forms the vent system 3400 is configured to allow a continuous vent flow from an interior of the plenum chamber 3200 to ambient whilst the pressure within the plenum chamber is positive with respect to ambient. The vent system 3400 is configured such that the vent flow rate has a magnitude sufficient to avoid or prevent a significant amount of rebreathing of exhaled $CO_2$ by the patient while maintaining the therapeutic pressure in the plenum chamber in use. The vent flow of gas from the vent system 3400 may be continuous throughout the patient's respiratory cycle.

The vent system/vent structure 3400 may be configured (e.g. sized, shaped and/or arranged) to maintain the thera-peutic pressure in the plenum chamber in use.

One form of vent system 3400 in accordance with the present technology comprises a plurality of holes, for example, about 20 to about 80 holes, or about 40 to about 60 holes, or about 45 to about 55 holes.

The vent system 3400 may be located in the plenum chamber 3200. Alternatively, the vent system 3400 is located in a decoupling structure, e.g., a swivel. In one example, as shown in FIG. 13, the vent system 3400 is located in an air circuit 4170. The vent system 3400 may fluidly connect a first portion of the air circuit 4170 to second portion of the air circuit 4170. For example, the vent system 3400 may fluidly connect a first portion of the air circuit 4170 that is connected to an RPT device 4000 to a second portion of the air circuit 4170, such as a vent connector tube 4180, that is connected to the patient interface 3000 and configured to make a connection with the vent system 3400. In another example, the vent system 3400 fluidly connects the patient interface 3000 with the air circuit 4170. The vent system 3400 may connect an end of an air circuit 4170 to a decoupling structure 3500, such as a swivel elbow, in some examples.

As shown in FIGS. 9A-12D, the vent system 3400 according to examples of the present technology may comprise a vent housing 3402 and a membrane 3450. The membrane 3450 may have a non-planar shape, for example the membrane 3450 may have a tubular shape, such as a cylindrical shape. The membrane 3450 may have, for example, a frustoconical shape. In some examples, the membrane 3450 may comprise one or more walls that curve from one end to the other end. The membrane 3450 may have the shape of a spherical section, in some examples.

In some embodiments, the membrane 3450 comprises axial symmetry, e.g. the membrane 3450 may comprise an axis about which the membrane 3450 is substantially symmetrical. For example, the membrane 3450 may comprise a longitudinal axis and the shape of the membrane 3450 may comprise axial symmetry around the longitudinal axis. The axial symmetry of membrane 3450 and vent housing 3402 also facilitates the use of a vent system 3400 as a connector between portions of an air circuit 4170 or between the air circuit 4170 and a patient interface 3000. Many air circuit connector components are tubular or are otherwise round, providing a central path through which a therapy flow of gas is able to pass. The axial symmetry of vent system 3400 may facilitate a connection between portions of an air circuit while maintaining a similar form to the air circuit 4170, such as a slim form that may not be considered excessively wide in comparison to the air circuit 4170. The vent system may provide a central passage for a therapy flow of gas to pass though the vent system 3400, while further features of the vent system 3400, such as an exhaust gas flow path and exhaust gas orifices, may be provided symmetrically around the axis of the vent system 3400 outwardly of the axis. The exhaust gas flow passage may also be axially symmetric and may occupy a contiguous space about an entire circumference in the vent housing.

The membrane 3450 may be configured to deform or deflect to alter a cross-sectional area of an exhaust gas flow passage through which a vent flow of gas flows from the plenum chamber 3200 to atmosphere.

By dynamically adjusting a cross-sectional area of the exhaust gas flow passage, the vent system 3400 may provide a substantially constant vent flow of gas throughout a range of typical therapeutic pressures. By structuring the vent system 3400 to maintain a constant rate of vent flow over most of the range of typical therapeutic pressures, the demands on the RPT device 4000 to provide a sufficient flow of air to maintain the desired therapeutic pressure within the plenum chamber 3200 despite losses, such as due to venting, are decreased compared to conventional vent systems. When the demands on the RPT device 4000 are decreased, it is possible to reduce the costs of manufacturing such devices because a less complex and less powerful RPT device 4000 is required to provide the same level of therapy. A number of exemplary configurations of the vent system 3400 and a more detailed functional explanation follow below.

5.3.4.1 Vent Housing

FIGS. 9A to 9F, 10A to 10D, 11A to 11D and 12A to 12D depict examples of different vent system 3400 configurations. The vent system 3400 comprises a vent housing 3402 in these examples. The vent housing 3402 may have a first end 3404 and a second end 3405. The first end 3404 of the vent housing 3402 and the second end 3405 of the vent housing 3402 are aligned along a longitudinal axis 3406 in these examples. Interior to the vent housing 3402 is a pressurised volume 6000. In some examples of the present technology the pressurised volume 6000 may be part of the plenum chamber 3200. In other examples, the pressurised volume 6000 may be in a different location where venting of a flow of gas may be required, such as in an air circuit 4170. The pressurised volume 6000 may be located between a first portion of the air circuit 4170 and a second portion of the air circuit 4170, e.g. the vent connector tube 4180.

The vent housing 3402 may be configured to receive a flow of gas from the RPT device 4000 from the first end 3404 of the vent housing 3402 and supply a therapy flow of gas to the patient interface 3000 from the second end 3405 of the vent housing 3402. For example, the vent housing 3402 may comprise an inlet 3407 to receive a flow of gas and an outlet 3408 to supply the therapy flow of gas. The vent housing 3402 includes at least one exhaust gas orifice to allow exhaust gas to be discharged to atmosphere (indicated by numeral 6100) from the pressurised volume 6000. The vent flow of gas may flow from the pressurised volume 6000 to atmosphere 6100 via at least one exhaust gas flow passage 6002.

The vent housing 3402 may be configured (e.g. sized, shaped and/or arranged) to maintain the therapeutic pressure in the plenum chamber 3200 in use.

The vent housing 3402 may include a plurality of diffused exhaust gas orifices 3471. In other examples, the vent housing 3402 may include one diffused exhaust gas orifice 3471, or any number, including zero. In these examples the vent housing 3402 may also comprise one or more undiffused exhaust gas orifices 3472, to be discussed in more detail below. In some examples the vent system 3400 may be configured to discharge exhaust gas to a region of lower pressure than the pressurised volume 6000, but not to atmosphere (or not directly to atmosphere), for example an expiratory limb of a patient circuit 4170.

The at least one exhaust gas orifice 3471 (e.g. a single exhaust gas orifice 3471 or a plurality thereof, as the case may be) may be sized and shaped to maintain the therapeutic pressure in the plenum chamber 3200 in use.

As will be described, the vent system includes a membrane-facing surface 3424 inside of the vent housing 3402. The membrane-facing surface 3424 may be a surface of the vent housing 3402.

The vent housing 3402 may comprise a first housing member 3430 at the first end 3404 of the vent housing 3402 and a second housing member 3440 at the second end 3405 of the vent housing 3402. The first housing member 3430 and the second housing member 3440 are configured to connect together in these examples. The first housing member 3430 and second housing member 3440 may be configured to be indirectly or directly connected to each other. In some examples of the present technology the first housing member 3430 and second housing member 3440 may be separable from one another, such as by a threaded connection, friction fit connection, snap fit connection, for example. In other examples, the first housing member 3430 and second housing member 3440 may be permanently connected together, such as by being integrally formed as one component, welding, permanent snap-fitting or the use of adhesive, for example.

FIG. 9E shows the vent system 3400 according to one example connected to components of an air circuit 4170. The vent system 3400 is connected between an air circuit 4170 and a vent connector tube 4180. The vent housing 3402 is connected at an upstream end to an air circuit connector 4171 of the air circuit 4170 and at a downstream end to a tube connector 4182. The vent system 3400 receives a flow of gas from a respiratory pressure therapy (RPT) device indicated by 6201 and delivers a therapy flow of gas indicated by 6202 to a downstream patient interface. The vent system 3400 also allows a vent flow of gas indicated by 6203 to be discharged to atmosphere 6100. In this example the vent flow of gas 6203 is discharged in a diffused vent flow of gas indicated by 6204 and in an undiffused vent flow of gas indicated by 6206.

5.3.4.1.1 First Housing Member

The first housing member 3430 comprises the inlet 3407 to the vent housing 3402 in these examples. The first housing member 3430 may comprise an inlet connection portion 3416 configured to fluidly connect the vent system 3400 to a supply conduit such as air circuit 4170. The inlet connection portion 3416 may be provided towards a first end 3431 of the first housing member 3430 (e.g. a first housing member upstream end), such as at or proximate the first end 3431 of the first housing member 3430. The inlet connection portion 3416 may comprise a bayonet fitting 3418 configured to engage a corresponding fitting of the air circuit 4170. In other examples, the inlet connection portion 3416 may be configured to fluidly connect with an air circuit 4170 by another means, such as by a snap-fit connection or a friction fit, for example. FIG. 9E shows the vent system 3400, in one example, connected to an air circuit 4170 by an air circuit connector 4171 which is engaged with the inlet connection portion.

The first housing member 3430 may comprise a shaft 3434 configured to project into the interior of the vent system 3400, as shown in FIGS. 9C and 10C. In other examples of the present technology the first housing member 3430 of the vent system 3400 does not include a shaft 3434. The shaft 3434 projects from a first end 3404 of the vent housing 3402 towards a second end 3405 of the vent housing 3402. The shaft 3434 may be centrally located within the vent housing 3402. In these examples, the shaft 3434 extends into the pressurised volume 6000. The shaft 3434 may terminate at a second end 3432 of the first housing member 3430 (e.g. a first housing member downstream end), within the pressurised volume. The shaft 3434 is hollow with an opening at each end to receive and supply the flow of gas from the RPT device 4000 to the pressurised volume 6000.

In these examples, the shaft 3434 is aligned with the longitudinal axis 3406 of the vent housing 3402. In other examples, the vent system 3400 may include a shaft 3434 that is not centred, and/or extends at angle, with respect to an axis of the first housing member 3430 and/or the second housing member 3440. For example, a vent system 3400 incorporated into a swivel elbow of a patient interface 3000 may include multiple parts with unaligned axes to form the elbow shape.

The inlet connection portion 3416 of the first housing member 3430 is provided on the shaft 3434. The shaft 3434 may include an outer substantially cylindrical surface at the first end 3431 of the first housing member 3430. The bayonet fitting 3418 extends radially outwards from the shaft 3434 in these examples.

The membrane-facing surface 3424 may be provided on the first housing member 3430. More particularly, the membrane-facing surface 3242 may be provided on an outer surface of the first housing member 3430 of the vent housing 3402, the outer surface being located within the vent housing 3402. The membrane-facing surface 3424 is provided on the shaft 3434 in the examples of FIGS. 9A to 9G and 10A to 10D. In these examples, the membrane-facing surface 3424 is provided on the outside of the shaft 3434 towards the second end 3432 of the first housing member 3430, such as at or proximate the second end 3432 of the first housing member 3430.

The membrane-facing surface 3424 may comprise a restrictor portion 3425 forming a region having a smaller cross-sectional area than adjacent regions in the exhaust gas flow passage 6002. The restrictor portion 3425 may form a restriction in the exhaust gas flow passage 6002. The significance of a smaller cross-sectional area and/or a restriction in the exhaust gas flow passage 6002 will be described below. The restrictor portion 3425 may be provided on an exterior portion of the shaft 3434 towards the second end 3432 of the first housing member 3430, such as at or proximate the second end 3432 of the first housing member 3430.

Examples of the present technology include various options for the restrictor portion. The membrane-facing surface 3424 may comprise contoured surfaces forming the restrictor portion 3425, as shown in FIGS. 9C-9G. Alternatively, or additionally, the restrictor portion 3425 may comprise a rib in the membrane-facing surface. The rib forming the restrictor portion 3425 may be provided around a circumference of the shaft 3434. Alternatively, or additionally, the restrictor portion 3425 may comprise a region of increased material thickness of the first housing member 3430. In other examples of the present technology the restrictor portion 3425 may be provided on an inwardly facing surface of the vent housing 3402, for example where the membrane 3450 is positioned inwardly of the membrane-facing surface 3424.

The first housing member 3430 may comprise a rounded surface 3433 towards the second end 3432 of the first housing member 3430, such as at or proximate the second end 3432 of the first housing member 3430. The rounded surface 3433 may be formed by a rounded edge at the periphery of the second end 3432 of the first housing member 3430. The rounded surface 3433 may provide a lower impedance to the vent flow of gas entering the exhaust gas flow passage 6002. A lower impedance to the vent flow of gas entering the exhaust gas flow passage 6002 may improve the efficiency of the vent system 3400. Additionally, the rounded surface 3433 before the entrance to the exhaust gas flow passage 6002 may help prevent regions of circulation of gas within the exhaust gas flow passage 6002 proximate the end of the shaft, which may form if there is a sharp corner at the outer edge of the shaft 3434. The smooth entrance to the exhaust gas flow passage 6002 may also be achieved by non-rounded geometry proximate the entrance, such as one or more chamfers at the outer circumference on the end of the shaft 3434, such as a bevelled edge.

The first housing member 3430 may comprise an outwardly projecting flange 3435. The flange 3435 may be located towards the first end 3431 of the first housing member 3430, such as at or proximate the first end 3431 of the first housing member 3430. The flange 3435 may be located proximate the first end 3431 of the first housing member 3430, approximately halfway between a central point along the shaft 3434 and the first end 3431 of the first housing member 3430. The flange 3435 may extend outwardly from the shaft 3434. The flange 3435 may be configured to connect to an exhaust gas orifice member 3470 of the vent system 3400. The side of the flange 3435 facing the second end of the vent housing 3402 may be configured to connect to the exhaust gas orifice member 3470.

The flange 3435 may comprise flange projections 3436 extending from the flange 3435 (as shown in FIG. 9B, in one example). The flange projections 3436 are configured to the connect to the exhaust gas orifice member 3470, in this example. The flange projections 3436 may project in a perpendicular direction to the flange 3435. The flange projections 3436, in this example, extend towards the exhaust gas orifice member 3470. The first housing member 3430 may comprise any number of flange projections 3436, such as one, two, three, or more. The flange projections 3436 may form a removable connection with the exhaust gas orifice member 3470, such as a snap fit or friction fit connection. Alternatively, the flange projections 3436 may be connected permanently to the exhaust gas orifice member 3470, such as by being integrally formed with the exhaust gas orifice member 3470 or by a bonded, welded or permanent snap fit connection.

The membrane-facing surface 3424 may alternatively be provided on an interior surface of the first housing member 3430, as shown in the examples of FIGS. 11A to 11D and 12A to 12D. The membrane-facing surface 3424 may have any suitable shape and structure. For example, the membrane-facing surface 3424 is frustoconical in the examples of FIGS. 11A to 11D and cylindrical in FIGS. 12A to 12D.

5.3.4.1.2 Second Housing Member

The second housing member 3440 may include a first end 3441 (e.g. a second housing member upstream end) and a second end 3442 (e.g. a second housing member downstream end) opposite the first end 3441.

The second housing member 3440 comprises the outlet 3408 to supply the therapy flow of gas in these examples. The second housing member 3440 may comprise an outlet connection portion 3420 configured to fluidly connect the vent system 3400 to the patient interface 3000. The outlet connection portion 3420 may be configured to connect directly or indirectly to the patient interface 3000. In some examples, the outlet connection portion 3420 may connect to a swivel elbow of a patient interface 3000 or to a portion of air circuit 4170 connected between the vent system 3400 and the patient interface 3000, e.g. a gas supply tube. In other examples, the outlet connection portion 3420 may be configured to connect to a patient interface 3000 or a vent connector tube 4180 of, or connected to, a patient interface 3000 (as shown in FIG. 13). The vent connector tube 4180 may be known as a "short tube". FIG. 9E shows the vent system 3400, in one example, connected to a vent connector tube 4180 by tube connector 4182 which is engaged with the outlet connection portion 3420.

The outlet connection portion 3420 may be configured to form a snap fit to engage a corresponding portion of the patient interface 3000, tube connector 4182 or vent connector tube 4180. In the examples of FIGS. 9A to 9G and 10A to 10D the outlet connection portion 3420 comprises a recess 3422 configured to receive a corresponding feature (not shown) provided on a patient interface 3000, short tube 4180, swivel elbow or other adaptor for connecting the outlet connection portion 3420 to the patient interface 3000. The corresponding feature may be, for example, a rib configured to snap fit into the recess 3422.

As will be described in more detail below, the second housing member 3440 may comprise a plurality of projections 3444 to limit movement of the membrane 3450. The second housing member 3440 may comprise an inwardly extending membrane stop flange 3446 on which the projections 3444 are provided.

5.3.4.2 Membrane

The membrane 3450 may have a first end 3451 and second end 3452 (e.g. a first membrane end 3451 and a second membrane end 3452). The first end 3451 of the membrane 3450 and second end 3452 of the membrane 3450 may be spaced apart along a longitudinal axis 3454, such as in examples where the membrane 3450 is cylindrical, has another axially symmetrical shape. The longitudinal axis 3454 of the membrane 3450 may be aligned with the longitudinal axis 3406 of the vent housing 3402.

5.3.4.2.1 Moveable Portion of the Membrane

The membrane 3450 also includes a moveable portion 3456, as shown in FIGS. 9A to 12D. The moveable portion 3456 of the membrane 3450 may be located between the first end 3451 of the membrane 3450 and the second end 3452 of the membrane 3450. The first end 3451 of the membrane 3450 and the second end 3452 of the membrane 3450 in these examples are spaced apart along a longitudinal axis of the membrane 3450. The moveable portion 3456 of the membrane 3450 may surround the longitudinal axis of the membrane 3450 between the first end 3451 of the membrane 3450 and the second end 3452 of the membrane 3450. The moveable portion 3456 may be located generally centrally between the first end 3451 of the membrane 3450 and the second end 3452 of the membrane 3450. The moveable portion 3456 may be provided circumferentially around the longitudinal axis of the membrane 3450. The membrane 3450 in these examples has an elongate shape, such as a tube or conical section. In other examples, the moveable portion 3456 may surround the longitudinal axis of the membrane 3450 with a cross-sectional shape that is not perfectly circular, for example having lobes or in the form of a triangle with rounded sides.

The moveable portion 3456 is spaced radially, with respect to the longitudinal axis of the membrane 3450, from the membrane-facing surface 3424 inside the vent housing 3402. An exhaust gas flow passage 6002 is formed between the membrane-facing surface 3424 and the moveable portion 3456 of the membrane 3450. The vent flow of gas may flow from the pressurised volume 6000 through the exhaust gas flow passage 6002 during use. In this example, the gas may flow to atmosphere 6100 via the diffused exhaust gas orifices 3471 or undiffused exhaust gas orifices 3472. The exhaust gas flow passage 6002 of the vent system 3400 shown in FIGS. 9A-9E may occupy a contiguous space about an entire circumference in the vent housing 3402. The circumference may be about the longitudinal axis of the membrane 3450. In other examples of the present technology, there may be multiple discrete exhaust gas flow passages 6002.

5.3.4.2.2 Operation of the Moveable Portion

The moveable portion 3456 of the membrane 3450 is configured to move with respect to the membrane-facing surface 3424. The moveable portion 3456 of the membrane 3450 may be elastically deformable in order to move. The moveable portion 3456 of the membrane 3450 is moveable in the sense that one or more areas or the moveable portion 3456 move(s). Translational movement of the moveable portion 3456 as a whole is not required for the moveable portion 3456 to be "moveable". In the examples of FIGS. 9A to 12D, the moveable portion 3456 is moveable because the material forming the moveable portion 3456 is able to move by deforming (e.g. constricting or expanding). In other examples of the present technology the moveable portion 3456 may not deform and may instead translate, rotate or otherwise move. In some examples, the moveable portion 3456 of the membrane 3450 is configured to move radially with respect to the membrane-facing surface 3424. In some examples, the moveable portion 3456 of the membrane 3450 is configured to move radially inward. In other examples, the moveable portion 3456 of the membrane 3450 is configured to move radially outward.

The moveable portion 3456 of the membrane 3450 is configured to move with respect to the membrane-facing surface 3424 to change a cross-sectional area of the exhaust gas flow passage 6002. The membrane 3450 is configured to regulate the vent flow of gas throughout the therapeutic pressure range.

The moveable portion 3456 of the membrane 3450 may be configured to move in response to differences in pressure between an interior side of the membrane 3450 and an exterior side of the membrane 3450. The moveable portion 3456 of the membrane 3450 is, in these examples, configured to move with respect to the membrane-facing surface 3424 in response to changes in pressure in the pressurised volume 6000 with respect to atmosphere. The membrane 3450 may be exposed on one side of the moveable portion 3456 (e.g. the exterior) to a force resulting from the pressure of the pressurised volume 6000, and exposed on the other side of the moveable portion 3456 (e.g. the interior) to a lower force, resulting from pressure of gas in the exhaust gas flow passage 6002. Differences in the forces on either side of the moveable portion 3456 of the membrane 3450 may cause the moveable portion 3456 to move. In particular, the vent flow of gas in the exhaust gas flow passage 6002 may have a higher velocity and a lower pressure than the gas in the pressurised volume 6000 in which case there will be a net force on the moveable portion 3456 of the membrane 3450 in the direction of the exhaust gas flow passage 6002, urging the moveable portion 3456 towards the membrane-facing surface.

The lower pressure in the exhaust gas flow passage 6002 in comparison to the pressurised volume 6000 may result at least in part by effects caused by the Bernoulli principle. The higher velocity of the gas in the exhaust gas flow passage 6002 in comparison to the pressurised volume 6000 results in a lower pressure being applied to the moveable portion 3456 of the membrane 3450 on the side of the exhaust gas flow passage 6002.

On the higher-pressure side of the moveable portion 3456 of the membrane 3450 (e.g. the exterior side in the examples shown in FIGS. 9C-9G, 10C and 10D, or the interior side in the examples shown in FIGS. 11C, 11D, 12C and 12D) the vent system 3400 may comprise a stagnant air cavity 6040 as shown in FIGS. 11C, 11D, 12C and 12D. In these examples, the stagnant air cavity 6040 is located on a first side of the moveable portion 3456 of the membrane 3450, and the exhaust gas flow passage 6002 is located on a second side of the moveable portion 3456 of the membrane 3450. The stagnant air cavity 6040 holds air (or other breathable gas) that is stationary or slow moving in comparison to the air flowing through the exhaust gas flow passage 6002, which may increase the effect of the Bernoulli principle. Additionally, the stagnant air in the stagnant air cavity may be less susceptible to turbulent movement of the air, reducing the chance of vibrations being induced in the moveable portion 3456 of the membrane 3450. A stagnant air cavity may also facilitate damping of vibrations in the moveable portion 3456 of the membrane 3450.

At a relatively high therapy pressure (e.g. 18 cmH$_2$O), the pressure difference between the pressurised volume 6000 and atmosphere 6100 (e.g. ambient pressure) will be relatively high. In the absence of any movement of the moveable portion 3456 of the membrane 3450 with respect to the membrane-facing surface 3424, the flow rate of the vent flow of gas through the exhaust gas flow passage 6002 would also be relatively high. However, a relatively high flow rate of exhaust gas results in a lower pressure acting on the moveable portion 3456 of the membrane 3450 on the side of the exhaust gas flow passage 6002 relative to the other side. As a result, the moveable portion 3456 of the membrane 3450 is urged into the exhaust gas flow passage 6002 towards the membrane-facing surface 3424. When this occurs, a spacing between the membrane 3450 and the membrane-facing surface 3424 is reduced, which reduces the cross-sectional area of the exhaust gas flow passage 6002 and through which the vent flow of gas must pass. The reduction in cross-sectional area impedes the flow of gas and prevents or minimises the increase in flow rate that would otherwise result from a higher pressure in the pressurised volume 6000 with respect to atmosphere 6100.

FIG. 9G shows deflection of the membrane 3450 in use during therapy with a high therapy pressure. As illustrated, during respiratory therapy a vent flow of gas 6203 flows past the moveable portion 3456 of the membrane 3450 between the moveable portion 3456 and the membrane-facing surface 3424 of the vent housing 3402. The lower pressure created by the higher velocity of the air in the exhaust gas flow passage 6002, in comparison to the air on the opposite side of the membrane 3450, results in the moveable portion 3456 of the membrane 3450 deflecting towards the membrane-facing surface 3424. As illustrated, the membrane 3450 constricts such that a central portion (along the length of the membrane 3450) is closer to the membrane-facing surface 3424 and the cross sectional area through which the vent flow of gas must pass is smaller, limiting the vent flow of gas.

At a lower therapy pressure (e.g. 6 cmH$_2$O), the pressure difference between the pressurised volume 6000 and atmosphere 6100, and the flow rate of the vent flow of gas, will be lower than for a higher therapy pressure. The velocity of the vent flow of gas through the exhaust gas flow passage 6002 will still result in a low-pressure region on one side of the moveable portion 3456 of the membrane 3450, but the pressure difference across the moveable portion 3456 will not be as large in comparison to a higher therapy pressure. Accordingly, the moveable portion 3456 of the membrane 3450 will be urged to move into the exhaust gas flow passage 6002 and towards the membrane-facing surface 3424 with a lower force than in comparison to if the therapy pressure was higher. This results in less impedance on the vent flow of gas at lower therapy pressures.

FIG. 9F shows deflection of the membrane 3450 in use during therapy with a lower therapy pressure than is shown in FIG. 9G. A region of low pressure is still created between the moveable portion 3456 of the membrane 3450 and the membrane-facing surface 3424, but the difference in pressure created between the interior and exterior of the membrane 3450 is not as large as would be created during use of the vent system 3400 with a higher therapy pressure. Accordingly, as illustrated, the moveable portion 3456 of the membrane 3450 does not deflect as much as it would during therapy with a higher pressure.

The moveable portion 3456 of the membrane 3450 is configured to impede the vent flow of gas to an extent dependent on the therapy pressure and regulate the vent flow of gas throughout the therapeutic pressure range. Thus, the vent system 3400 is capable of maintaining an approximately constant vent flow rate over the typical range of therapeutic pressures. The RPT device 4000 itself can be relied upon less to regulate and maintain the desired therapeutic pressure and vent flow rate, because the vent system 3400 can provide this functionality. Accordingly, the RPT device 4000 requires less complex hardware compared to RPT devices used with conventional vent systems, because it is not relied upon as much to regulate flow and pressure. Furthermore, the RPT device 4000 requires less complex control features, because, again, it is not relied upon as much regulate flow and pressure.

FIG. 8 shows a plot of the flow rate of the vent flow of gas through an exemplary vent system 3400 for a range of therapy pressures. As shown, in a range of therapy pressures between 4 and 25 cmH₂O, the flow rate of the vent flow of gas does not increase with pressure over the entire range of therapy pressures. Instead, the flow rate slightly increases and then slightly decreases over the therapy pressure range, regulating the vent flow of gas to approximate a constant flow rate across a range of therapy pressures.

5.3.4.2.3 Structure of the Moveable Portion

In the examples of the present technology shown in FIGS. 9A-D, the moveable portion 3456 of the membrane 3450 is substantially cylindrical. Forming the moveable portion 3456 of the membrane 3450 in the form of a cylinder may enable the vent housing 3402 to have a smaller overall diameter than a vent housing which includes a membrane having a planar form. In other forms of the present technology, such as the vent system 3400 shown in FIGS. 10A-D and 11A-D, the moveable portion 3456 of the membrane 3450 comprises a frustoconical shape. A frustoconical moveable portion 3456 of the membrane 3450 may also enable the vent housing 3402 to be narrower than if a planar membrane was incorporated. A tubular membrane may enable a lower overall diameter of the vent housing in comparison to a planar annular membrane, such as a disc-shaped membrane with a central hole.

In these examples of the present technology, the membrane 3450 and the moveable portion 3456 have a longitudinal axis 3454 which is aligned substantially parallel to the direction of the flow of gas received from the RPT device 4000 and/or supplied to the patient interface 3000. Additionally, the moveable portion 3456 of the membrane 3450 comprises a wall aligned parallel to the flow of gas through the vent housing 3402 from the first end 3404 of the vent housing 3402 to the second end 3405 of the vent housing 3402. In this example, the moveable portion 3456 of the membrane 3450 includes a single cylindrical wall having a longitudinal axis 3454 aligned parallel to the direction of the flow of gas through the vent housing 3402 from the first end 3404 of the vent housing 3402 to the second end 3405 of the vent housing 3402. In other examples the moveable portion 3456 of the membrane 3450 may comprise a plurality of walls such as two, three or more. The walls may be non-planar and comprise a number of discrete lobes connected at their edges, or may be planar and comprise a number of discrete planar walls forming a hexagonal shape, an octagonal shape or the like.

As the moveable portion 3456 of the membrane 3450 comprises wall(s) aligned parallel to the flow of gas through the vent housing 3402, the moveable portion 3456 may be less affected by acoustic noise travelling through the vent system 3400. Acoustic noise propagating parallel to the flow of gas (e.g. noise generated by the patient 1000 transmitted back along the flow path from the patient interface 3000 or noise generated by the RPT device 400 travelling downstream along the flow path) may generally propagate in a direction parallel to the walls of the moveable portion 3456 of the membrane 3450. A moveable portion 3456 of the membrane 3450, comprising wall(s) aligned parallel to the direction in which pressure oscillations caused by acoustic noise propagate, may be less susceptible to vibration caused by the noise, in comparison to wall(s) aligned perpendicular to the direction of propagation. That is, wall(s) aligned parallel to the flow of gas through the vent system 3400 may be less affected by noise than wall(s) aligned perpendicular to the flow through the vent system 3400. The moveable portion 3456 of the membrane 3450 may therefore transmit low acoustic noise levels, at least in comparison to a moveable portion 3456 of the membrane 3450 that has wall(s) perpendicular to the flow, such as a planar annular membrane (e.g. in the shape of a disc with a central hole). The vent system 3400 may therefore be relatively quiet or at least quieter than alternative arrangements.

The moveable portion 3456 of the membrane 3450 may be formed from silicone. In other examples, the moveable portion 3456 of the membrane 3450 may be formed from another suitable material such as a rubber or thermoplastic elastomer.

The membrane 3450 may be mounted outwardly of the membrane-facing surface 3424, as shown in FIGS. 9C-9G, 10C and 10D. In these examples, the moveable portion 3456 of the membrane 3450 is provided around the membrane-facing surface 3424. The membrane 3450 and the membrane-facing surface 3424 are concentric in these examples, e.g. they share a common axis.

The moveable portion 3456 of the membrane 3450 is configured to move inwardly to restrict the vent flow of gas in the examples of FIGS. 9A to 9G and 10A to 10D. More particularly, the moveable portion 3456 of the membrane 3450 may be configured to constrict to move inwardly towards the membrane-facing surface 3424. In other examples of the present technology, such as the examples of FIGS. 11A to 11D and 12A to 12D, the moveable portion 3456 of the membrane 3450 is configured to move outwards towards the membrane-facing surface. However, in a vent system 3400 with a cylindrical or frustoconical membrane 3450, an advantage of the moveable portion 3456 of the membrane 3450 moving inwards (e.g. constricting) is that the movement does not induce hoop stress in the moveable portion 3456 of the membrane 3450. That is, a cylindrical membrane 3450 may deform into an hour-glass shape when the moveable portion 3456 moves radially inward. Accordingly, it may require a lower force (e.g. a lower difference in pressure across the membrane 3450) to effect movement of the membrane 3450 inwards in comparison to outwards. The added hoop stress may also make the moveable portion 3456 of the membrane 3450 more unstable when moving outwards than when moving inwards. FIGS. 9F and 9G show deflection of the membrane 3450 by different amounts. As shown in FIG. 9F, the moveable portion 3456 of the membrane 3450 has moved towards the membrane-facing surface 3424 by a smaller amount (as may occur during therapy with a lower therapy pressure), while in FIG. 9G the moveable portion 3456 of the membrane 3450 has moved towards the membrane-facing surface 3424 by a larger amount (as may occur during therapy with a higher therapy pressure).

While there may be advantages to inwards movement of the membrane 3450, the present technology includes vent systems 3400 including a membrane 3450 having a moveable portion 3456 which moves outwardly to move towards the membrane-facing surface. In such example, such as those shown in FIGS. 11A to 11D and 12A to 12D, the moveable portion 3456 of the membrane 3450 may be supported inwardly of the membrane-facing surface 3424. Accordingly, the moveable portion 3456 of the membrane 3450 may move outwardly to restrict the vent flow of gas. The moveable portion 3456 of the membrane 3450 may be configured to expand to move towards the membrane-facing surface 3424. Where the membrane 3450 has a cylindrical form, the membrane 3450 may bulge outwards when the moveable portion 3456 moves radially outward.

In some examples, the membrane 3450 may comprise a planar structure. While a generally tubular membrane 3450 provides some advantages to the vent system 3400, other advantageous features of a vent system 3400 according to the present technology may be applied in a vent system 3400 that has a planar membrane 3450. For example, a stagnant air cavity 6040, a damping chamber 6050 and/or a vent housing 3402 that reduces vibration of the membrane 3450 in modes higher than the first mode, as described here, are features which may be applied to a vent system 3400 having a planar membrane. One example of a planar membrane 3450 is a disc with a central hole (e.g. in the shape of a flat washer).

5.3.4.3 Membrane Stops

The vent housing 3402 may be configured to limit movement of the moveable portion 3456 of the membrane 3450 towards the membrane-facing surface 3424. Preventing the moveable portion 3456 of the membrane 3450 from moving too far towards the membrane-facing surface 3424 may advantageously prevent excessive impedance on the vent flow of gas or occlusion of the exhaust gas flow passage 6002.

The vent housing 3402 may contact an end of the membrane 3450 and prevent the end of the membrane 3450 from moving towards the membrane-facing surface 3424. The vent housing 3402 may comprise or provide one or more membrane stops configured to limit movement of the moveable portion 3456 of the membrane 3450. In the examples shown in FIGS. 9A to 9G, 10A to 10D, 11A to 11D and 12A to 12D, the vent housing 3402 contacts the second end 3452 of the membrane 3450 and prevents the second end 3452 of the membrane 3450 from moving towards the membrane-facing surface 3424. In this example, the vent housing 3402 comprises at least one projection 3444 configured to contact an end of the membrane 3450 to limit movement of the end of the membrane 3450, e.g. the second end 3452 of the membrane 3450.

The vent housing 3402 may comprise a plurality of projections 3444. The projections 3444 may be known as stoppers. In other examples, the vent housing 3402 may comprise other types of membrane stops, such as an internal ring that contacts the movable portion before 56 of the membrane 3450 and which has a plurality of holes or other openings to allow for the flow of air into the exhaust gas flow passage 6002 or into the damping chamber 6050. In further examples, membrane stops may be provided to the membrane 3450 itself. Further still, in some examples the membrane 3450 may be configured to limit its own movement or have an end that is substantially unable to move or deform. In one example, a free end of the membrane 3450 may comprise a substantially rigid portion that is unable to deform and move towards the membrane-facing surface 3424.

In the examples shown in FIGS. 9A to 9G and 10A to 10D, the one or more projections 3444 are provided outside of the exhaust gas flow passage 6002. As the projections 3444 are located outside of the exhaust gas flow passage 6002, in these examples, the vent flow of gas does not pass around or between the projections 3444 when flowing to atmosphere 6100. An advantage of projections 3444 provided outside of the exhaust gas flow passage 6002 is that the projections 3444 are not able to disrupt the flow. In examples in which the projections 3444 are located within the flow of exhaust gas, there is the possibility that projections 3444 in the flow path may create a wake in the vent flow of gas downstream of the projections creating turbulence which may increase the noise of the vent system 3400. Additionally, turbulent vent flow may induce the moveable portion 3456 of the membrane 3450 to resonate or otherwise vibrate, which may further increase noise level of the vent system 3400.

In the example vent systems 3400 shown in FIGS. 9A to 9G and 10A to 10D, the second housing member 3440 comprises a plurality of projections 3444. The projections 3444 may be located inwardly of the membrane 3450. In these examples, the projections 3444 project towards the first end 3404 of the vent housing 3402. The second housing member 3440 may comprise an inwardly extending membrane stop flange 3446 on which the projections 3444 are provided. The projections 3444 may project from the membrane stop flange 3446 in a direction towards the first end 3404 of the vent housing 3402. The one or more projections 3444 may contact an inside surface of the membrane 3450 at the second end 3452 of the membrane 3450. In this way, the inwards movement of the second end 3452 of the membrane 3450 is limited by the projections 3444.

In alternative examples of the technology, the vent housing 3402 may include only one projection 3444, for example in the form of one or more lips configured to fit within or around the second end of the membrane 3450. However, an advantage of multiple projections 3444 is that the multiple projections 3444 can define openings between adjacent pairs. The projections 3444 may comprise damping orifices 6055 between them, which will be discussed in more detail below.

The advantages of the projections 3444 being positioned outside of the vent flow of gas notwithstanding, in some examples the projections 3444 or other membrane stops may be positioned inside of the vent flow, for example within the exhaust gas flow passage 6002. The vent system 3400 examples shown in FIGS. 11C, 11D, 12C and 12D include projections 3444 provided on the membrane-facing surface 2424. The projections 3444 may be in the form of stops, protrusions, bumps, standoffs, tongues and the like. The projections 3444 contact respective portions of the moveable portion 3456 of the membrane 3450 to hold the moveable portion 3456 away from the membrane-facing surface 3424, preventing occlusion of the exhaust gas flow passage 6002.

The at least one projection 3444 may be provided on the first housing member 3430. In the examples of FIGS. 11A to 12D, a plurality of projections 3444 are provided on an inner surface of the first housing member 3430 to limit movement of the second end 3452 of the membrane 3450 towards the membrane-facing surface 3424 of the first housing member 3430. The projections 3444, in these examples, project radially inward from a cylindrical (in the example of FIGS. 12A to 12D) or conical (in the example of FIGS. 11A to 11D) surface of the first housing member 3430. The projections 3444 may contact an outside surface of the membrane 3450 at the second end 3452 of the membrane 3450.

5.3.4.4 Membrane Support

The vent system 3400 may comprise a membrane support 3460 on which the membrane 3450 is supported within the vent housing 3402. The membrane support 3460 may be a rigid structure supported by or in the vent housing 3402 configured to support the membrane and hold the first end 3451 of the membrane 3450 in place. The membrane 3450 may be moulded to the membrane support 3460 at the first end 3451 of the membrane 3450 in these examples. In other examples, the membrane 3450 may be moulded to the membrane support 3460 at the second end of the membrane 3450. In some examples of the technology the membrane 3450 may be fitted to the membrane support 3460 without a permanent connection thereto. The membrane 3450 may be fitted around a circumference of a cage or other substantially rigid structure, for example.

The membrane support 3460 may be configured to connect to the vent housing 3402 in these examples. The membrane support 3460 is configured to connect to the vent housing 3402 between the first end 3404 of the vent housing 3402 and the second end 3405 of the vent housing 3402 in these examples. The membrane support 3460 may be configured to connect to a central portion of the vent housing 3402, as shown in FIGS. 9C-9G, 10C and 10D. Alternatively, the membrane support 3460 may be configured to connect the vent housing 3402 towards the first end 3404 of the vent housing 3402, such as at or proximate the first end 3404 of the vent housing 3402, as shown in FIGS. 11C, 11D, 12C and 12D. In some forms of the present technology, where the orientation of the membrane 3450 is reversed, the membrane support 3460 may be configured to connect to the vent housing 3402 towards the second end 3405 of the vent housing 3402, such as at or proximate the second end 3405 of the vent housing 3402.

As shown in the example of FIGS. 9A to 9G, the membrane support 3460 may comprise a connection portion 3462 for connection to the vent housing 3402. The connection portion 3462 may be configured to connect directly or indirectly to the vent housing 3402. The connection portion 3462 may be cylindrically shaped and configured to fit around an exterior of the second housing member 3440. The connection portion 3462 may be concentric with the membrane 3450.

The membrane support 3460 may comprise a membrane support flange 3464 extending inwardly from an inside surface of the connection portion 3462 of the membrane support 3460, configured to support the membrane 3450. The membrane support flange 3464 may be spaced from the ends of the connection portion 3462. The membrane 3450 may be moulded to the membrane support flange 3464. As shown in the example of FIGS. 9A to 9G, the membrane support flange 3464 supports the membrane 3450 inwardly of the vent housing. The first end 3451 of the membrane 3450 is fixed to and supported on the membrane support flange 3464 in this example. Accordingly, the membrane support flange 3464 supports the first end 3451 of the membrane 3450 inside of the vent housing 3402 and the membrane 3450 extends from the membrane support flange 3464 towards the second end 3405 of the vent housing 3402.

The membrane support 3460 may comprise a baffle portion 3465, as shown in the examples of FIGS. 11A to 11D and 12A to 12D. The baffle portion 3465 is configured to shield one side of the membrane 3450 from flow of gas through the centre of the vent housing 3402. In these examples, the moveable portion 3456 of the membrane 3450 moves outwards towards the membrane-facing surface 3424 to restrict the flow of gas through the exhaust gas flow passage 6002. The baffle portion 3465 is cylindrical in these examples. In other examples, the baffle portion 3465 may be frustoconical, bell-shaped, or any other suitable shape. The baffle portion 3465 may be concentric with the moveable portion 3456 of the membrane 3450. In these examples, the baffle portion 3465 is provided radially interior to the moveable portion 3456 of the membrane 3450. As shown in the example of FIGS. 11A to 12D, the baffle portion 3465 has a first end 3466 connected to the moveable portion 3456 of the membrane 3450 at the first end 3451 of the membrane 3450. Additionally, the baffle portion 3465 has a second end 3467 provided towards the second end 3452 of the membrane 3450, such as at or proximate the second end 3452 of the membrane 3450.

In the example shown in FIGS. 11A to 11D, the baffle portion 3465 comprises a baffle flange 3468 at the second end 3467 of the baffle portion 3465. In this example, the baffle flange 3468 extends outwardly from the baffle portion 3465. The baffle flange 3468 may partially define an exhaust gas flow passage inlet 6004 to the exhaust gas flow passage 6002.

The rounded surface 3433 at or proximate the exhaust gas flow passage inlet 6004 may be a rounded edge of the membrane support 3460 at a second end thereof. The rounded surface 3433 may be provided on the baffle flange 3468 of the membrane support 3460, as shown in FIGS. 11A to 11D.

A damping chamber 6050 may be partially defined by the baffle portion 3465 of the membrane support 3460. The damping chamber 6050 may be partially defined by the outwardly extending flange of the baffle portion 3465.

5.3.4.5 Exhaust Gas Flow

The vent flow of gas may flow radially outwards at or proximate an entrance to the exhaust gas flow passage 6002. In the examples of FIGS. 9A to 9G, 10A to 10D, 11A to 11D, and 12A to 12D, and with particular reference to FIG. 9E in which various flows of gas are illustrated, a flow of gas 6201 from the RPT device 4000 to the patient interface 3000 flows in an axial direction through the vent housing 3402. Additionally, a portion of the flow of gas 6201 into the vent housing 3402 becomes a vent flow of gas 6203 which flows in a radial direction at or proximate the entrance to the exhaust gas flow passage 6002. The direction of the flow of gas within the vent housing 3402 may change from an axial direction to a radial direction to create a vent flow of gas 6203. The vent flow of gas 6203 may change direction from the radial direction to an axial direction aligned with the longitudinal axis of the vent system 3400 while or before passing through the entrance to the exhaust gas flow passage 6002. The vent flow of gas in the exhaust gas flow passage 6002 may flow parallel to the longitudinal axis 3406 of the vent housing 3402 and/or the longitudinal axis 3454 of the membrane 3450.

As discussed in more detail above, the vent housing 3402 may comprise a rounded surface 3433 at or proximate the entrance to the exhaust gas flow passage 6002, e.g. at the exhaust gas flow passage inlet 6004. The rounded surface 3433 may be configured to facilitate the change in direction of the vent flow of gas before the entrance to the exhaust gas flow passage 6002. More generally, the vent housing 3402 may comprise an exhaust gas flow passage 6002 having an exhaust gas flow passage inlet 6004 which is shaped to avoid large resistance to the flow of gas entering the exhaust gas flow passage 6002. This shape may be achieved by a rounded surface 3433 on the first housing member 3430 or a rounded or otherwise contoured surface on another portion of the vent housing 3402 or one of the components of the vent system 3400 (such as the second housing member 3440 in the example of FIGS. 11A to 11D).

The exhaust gas flow passage inlet 6004 may be an annular opening within the vent housing 3402. For example, in the examples of FIGS. 9A to 10D, the exhaust gas flow passage inlet 6004 is a single opening into the exhaust gas flow passage 6002 around the outside of the first housing member 3430. The first housing member 3430 and the membrane 3450 are concentric with each other, yet at the second end 3432 of the first housing member 3430 the membrane 3450 has a larger inner diameter than the outer diameter of the first housing member 3430, providing a gap forming the exhaust gas flow passage inlet 6004.

In some examples, the exhaust gas flow passage inlet 6004 may also be defined by an axial spacing between parts. In the examples shown in FIGS. 9A to 10D, an opening forming the exhaust gas flow passage inlet 6004 is also provided by an axial spacing between a portion of the first housing member 3430 and a portion of the second housing member 3440 in the interior of the vent housing 3402. In the example shown in FIGS. 11A to 11D, the exhaust gas flow passage inlet 6004 is formed primarily by an axial spacing between a portion of the membrane support 3460 and the vent housing 3402. In particular, the exhaust gas flow passage inlet 6004 is formed by a spacing in the axial direction between the membrane support 3460 and the second housing member 3440, in the examples of FIGS. 11A to 11D.

In the example shown in FIGS. 12A to 12D, the vent housing 3402 comprises a plurality of exhaust gas flow passage inlets 6004. The plurality of exhaust gas flow passage inlets 6004, in this example, are formed in the membrane support 3460, specifically in the baffle portion 3465. In other examples, a plurality of exhaust gas flow passage inlets 6004 could be provided elsewhere. A plurality of exhaust gas flow passage inlets 6004 may be provided by openings formed in the baffle flange 3468, for example. In further examples, a plurality of exhaust gas flow passage inlets 6004 may be provided by openings formed in the first housing member 3430, such as in the shaft 3434.

The vent housing 3402 may comprise a plurality of exhaust gas orifices 3471, 3472 configured to allow exhaust gas to pass to atmosphere 6100. The exhaust gas orifices may be spaced apart around a circumference of the vent housing 3402. The vent housing 3402 may comprise at least one diffused exhaust gas orifice 3471 and at least one undiffused exhaust gas orifice 3472. In the examples of FIGS. 9 and 11, the vent housing 3402 comprises a plurality of diffused exhaust gas orifices 3471 and a plurality of undiffused exhaust gas orifices 3472.

The vent system 3400 may comprise a diffuser member 3474 configured to diffuse and/or audibly muffle the exhaust gas as it leaves the vent system 3400. In other examples the vent system 3400 may comprise a plurality of diffuser members 3474. The diffuser member 3474 may be formed from a network of fibres through which the exhaust gas may be forced to follow a tortuous path, such as a felt material. Other materials which diffuse and/or audibly muffle the vent flow of gas may be used in the vent system 3400, such as open-cell foams.

The diffuser member 3474 may be located in series with the diffused exhaust gas orifice 3471 (e.g. over or behind) so as to require gas flowing through the at least one diffused exhaust gas orifice 3471 to flow through the diffuser member 3474. The at least one undiffused exhaust gas orifice 3472 may be open (e.g. not blocked by a diffuser member).

As shown in FIGS. 9A to 9G, 11A to 11D and 12A to 12D, and with particular reference to FIG. 9E which illustrates particular gas flow paths and a diffuser member 3474, the vent system 3400 provides a diffused vent flow path through which exhaust gas is able to be vented through the diffuser member 3474 and the at least one diffused exhaust gas orifice 3471. A diffused flow of gas is indicated in FIG. 9E by 6204. Additionally, the vent system 3400 provides an undiffused vent flow path through which exhaust gas is able to be vented through the at least one undiffused exhaust gas orifice 3472 in the examples of FIGS. 9A to 9G and 11A to 11D. An undiffused flow of gas is indicated in FIG. 9E by 6205.

The vent system 3400 may be configured to allow exhaust gas to flow through the at least one undiffused exhaust gas orifice 3472 in the event the exhaust gas is unable to flow through the diffuser member 3474 and the at least one diffused exhaust gas orifice 3471. Advantageously, the vent system 3400 in the examples of FIGS. 9A to 9G and 11A to 11D is able to vent exhaust gas in the event the diffuser member 6474 becomes clogged, blocked or otherwise unable to allow a sufficient vent flow of gas to pass through. As shown in FIG. 9E, a vent flow of gas 6203 flows through the exhaust gas flow passage 6002. The vent flow of gas 6203 is then able to flow either through the diffuser member 3474 and to atmosphere 6100 as a diffused vent flow of gas 6204 or directly to atmosphere 6100, bypassing the diffuser member 3474, as an undiffused vent flow of gas 6205. Which path the vent flow of gas takes may depend on whether or not the diffuser member 3474 is clogged or not.

In the example of FIGS. 9A to 9G and 11A to 11D, when the diffuser member 3474 is not clogged and is able to allow sufficient vent flow through the diffused exhaust gas orifices 3471, the vent housing 3402 provides a relatively high resistance to vent flow through the undiffused exhaust gas orifices 3472, in comparison to the diffused exhaust gas orifices 3471. Accordingly, when the diffuser member 3474 is in working condition (e.g. unblocked), the majority of vent flow passes through the diffuser member 3474 and through the diffused exhaust gas orifices 3471 as a diffused vent flow of gas 6204. When the diffuser member 3474 is clogged and its resistance to the flow of gas increases, the vent housing is still able to allow the vent flow of gas to pass through the undiffused exhaust gas orifices 3472 as an undiffused vent flow of gas 6205.

The vent housing 3402 may be shaped to require the flow of exhaust gas to change direction to a greater extent to flow through the at least one undiffused exhaust gas orifice 3472 than to flow through the diffused exhaust gas orifice 3471. The additional change in direction required to flow out the undiffused exhaust gas orifices 3472 provides enough resistance that the gas instead flows through the diffuser member 3474 instead of the undiffused exhaust gas orifices 3472. That is, the vent housing 3402 may be shaped to require the flow of exhaust gas to change direction to flow through the undiffused exhaust gas orifice 3472 to a sufficient degree that a majority of the flow of exhaust gas passes through the diffuser member 3474 and through the diffused exhaust gas orifice 3471 unless the diffuser member 3474 becomes clogged.

The vent housing 3402 may be shaped to require the flow of exhaust gas to change direction by approximately 90 degrees to flow through the one or more diffused exhaust gas orifices 3471, as shown in FIGS. 9C and 9D. The vent housing 3402 may be shaped to require the flow of exhaust gas to change direction by greater than 90 degrees to flow through the one or more undiffused exhaust gas orifices 3472, also as shown in FIGS. 9C and 9D. In various examples, the vent housing 3402 may be shaped to require the flow of exhaust gas to change direction by greater than 110, 130 or 150 degrees to flow through the one or more undiffused exhaust gas orifices 3472.

The diffused exhaust gas orifices 3471 and the undiffused exhaust gas orifices 3472 may be longitudinally spaced apart along the length of the vent housing 3402. In the examples of FIGS. 9A to 9G and 11A to 11D, the diffused exhaust gas orifices 3471 are located towards the first end 3404 of the vent housing 3402, such as at or proximate the first end 3404 of the vent housing 3402. In these examples, the undiffused exhaust gas orifices 3472 are located centrally between the first end 3404 of the vent housing 3402 and the second end 3405 of the vent housing 3402.

The diffused exhaust gas orifices 3471 may open in a lateral (i.e. radial) direction with respect the vent housing 3402. The exhaust gas may be highly diffused after venting from orifices that open laterally from a circumference of the vent housing 3402, as the exhaust gas may spread out over a progressively larger area as the exhaust gas travels away from the vent housing 3402. The undiffused exhaust gas orifices 3472 may open in a direction partially laterally and partially towards the second end 3405 of the vent housing 3402, i.e. at an oblique angle to the longitudinal axis of the vent housing 3402.

In some examples, the vent system 3400 may comprise a diffuser member 3474 configured to diffuse and/or audibly muffle the vent flow of gas, and may include one or more common exhaust gas orifices 3473 through which the vent flow gas is able to pass to atmosphere 6100 regardless of whether the diffuser member 3474 permits the flow within itself or not.

As shown in FIGS. 10A to 10D, the vent system 3400 comprises a first housing member 3430 including a flange 3435 and a diffuser retaining rim 3437. Held in place by the flange 3435 and the diffuser retaining rim 3437 is a diffuser member 3474. The diffuser member 3474 is positioned proximate to but spaced from a membrane support 3460 in the path of the flow of gas through the exhaust gas flow passage 6002 downstream of the membrane 3450. The vent system 3400 in this example comprises a low resistance flow path through the material of the diffuser member 3474 and then out the common exhaust gas orifices 3473, when the diffuser member 3474 is not clogged. Additionally, the vent system 3400 in this example comprises a high resistance flow path (when the diffuser member 3474 is not clogged) in which the flow of gas must make an abrupt change of direction downstream of the membrane 3450 (at the first end 3451 of the membrane 3450 in this example) and flow past the diffuser member 3474 and out to atmosphere through the common exhaust gas orifices 3473.

During normal operation of the vent system 3400 shown in FIGS. 10A to 10D, when the diffuser member 3474 is not clogged, the majority of the vent flow of gas will take the low resistance flow path through the diffuser member 3474. If the diffuser member 3474 becomes clogged or otherwise does not permit sufficient flow therethrough, the vent system 3400 is still able to function as exhaust gas is able to flow through the other flow path past the diffuser member 3474 which, when the diffuser member 3474 is clogged, becomes a lower resistance flow path.

The vent system 3400 may comprise at least one intermediate exhaust gas orifice 3478 upstream of the diffuser member 3474. In the examples of FIGS. 12A to 12D, the first housing member 3430 comprises a plurality of intermediate exhaust gas orifices 3478. The intermediate exhaust gas orifices 3478 are provided upstream of the diffuser member 3474. The intermediate exhaust gas orifices 3478 may or may not be covered by the diffuser member 3474. In the example shown in FIGS. 11A to 11D, the diffuser member 3474 does not cover the intermediate exhaust gas orifices 3478 so that the vent flow of gas may flow through either the diffuser member 3474 and then the diffused exhaust gas orifices 3471 or past the diffuser member 3474 and then through the undiffused exhaust gas orifices 3472.

In the example shown in FIGS. 12A to 12D, the diffuser member 3474 covers the intermediate exhaust gas orifices 3478. In this example, the diffuser member 3474 is substantially cylindrically-shaped to fit around a portion of the vent housing 3402. The diffuser member 3474 covers the intermediate exhaust gas orifices 3478 to diffuse and/or audibly muffle the vent flow of gas released therefrom. The gas is able to vent to atmosphere through the diffuser member 3474 through the diffused exhaust gas orifices 3471.

In the example shown in FIGS. 12A to 12D, a diffused exhaust gas orifice 3471 is also formed by a gap between a portion of the first housing member 3430 and the first end 3441 of the second housing member 3440. In general in any examples of the technology, exhaust gas orifices (diffused or undiffused) may be formed either by holes or openings formed in a single component of the vent housing 3402 (e.g. the first housing member or second housing member) or by gaps formed between multiple components of the vent housing 3402.

The second housing member 3440 may comprise a diffuser retaining portion 3448. In this example, the diffuser retaining portion 3448 is in the form of a cylindrical sleeve configured to fit over the first housing member 3430. The first housing member 3430 also has a substantially cylindrical second housing member connection portion 3438, in this example, at the second end 3432 of the first housing member 3430 and a diffuser retaining rim 3437 in the form of a flange at the second end 3432 of the first housing member 3430. In this example, the diffuser member 3474 is retained in a channel of the first housing member 3430 between the diffuser retaining rim 3437 and the second housing member connection portion 3449, while held in place radially by the diffuser retaining portion 3448 of the second housing member 3440.

In the example of FIGS. 12A to 12D the diffused exhaust gas orifice 3471 that is formed by a gap between the first housing member 3430 and the second housing member 3440 is formed by a gap between the diffuser retaining portion 3448 of the second housing member 3440 and the diffuser retaining rim 3437 of the first housing member 3430.

5.3.4.6 Exhaust Gas Orifice Member

The vent system 3400 may comprise an exhaust gas orifice member 3470 including the one or more exhaust gas orifices through which the vent flow of gas is able to pass out of the vent system 3400 to atmosphere 6100.

The vent systems 3400 shown in FIGS. 9A to 9G and 11A to 11D include an exhaust gas orifice member 3470. In these examples, the exhaust gas orifice member 3470 comprises a plurality of exhaust gas orifices. The at least one diffused exhaust gas orifice 3471 may be provided towards a first end 3476 of the exhaust gas orifice member 3470, such as at or proximate the first end 3476 of the exhaust gas orifice member 3470. In these examples, the diffused exhaust gas orifices 3471 are provided substantially at the first end 3476 of the exhaust gas orifice member 3470. The one or more undiffused exhaust gas orifices 3472 may be provided towards a second end 3477 of the exhaust gas orifice member 3470 opposite the first end 3476 of the exhaust gas orifice member 3470, such as at or proximate the second end 3477 of the exhaust gas orifice member 3470. The exhaust gas orifice member 3470 of the vent systems 3400 shown in FIGS. 9A to 9G comprises a plurality of diffused exhaust gas orifices 3471 towards the first end 3476 of the exhaust gas orifice member 3470 (e.g. at or proximate the first end 3476) and a plurality of undiffused exhaust gas orifices 3472 towards the second end 3477 of the exhaust gas orifice member 3470 (e.g. at or proximate the second end 3477).

The exhaust gas orifice member 3470 may be configured to connect to the first housing member 3430, as shown in FIGS. 9A to 9G and 11A to 11D examples. The exhaust gas orifice member 3470 may be formed in the shape of a ring. In the FIG. 9 example, the diffused exhaust gas orifices 3471 are formed in the exhaust gas orifice member 3470 to open laterally, radially outward from an axis of the exhaust gas orifice member 3470. Additionally, the undiffused exhaust gas orifices 3472 are formed in the exhaust gas orifice member 3470 to open in a direction partially radially and partially axially with respect to the exhaust gas orifice member 3470. The undiffused exhaust gas orifices 3472 open in an oblique direction to the lateral direction to which the diffused exhaust gas orifices 3471 open in this example. The different opening directions of the exhaust gas orifices contribute to the resistances of the different flow paths that the vent flow may take to pass out of the vent system 3400, as described in more detail above.

In the examples of FIGS. 9A to 9G and 11A to 11D, the diffuser member 3474 is retained in the vent system 3400 by the exhaust gas orifice member 3470. The diffuser member 3474 is housed between the exhaust gas orifice member 3470 and the first housing member 3430, in these examples.

In the example vent system 3400 shown in FIGS. 9A to 9G, the exhaust gas orifice member 3470 and the membrane support 3460 are configured to connect together to connect the first housing member 3430 and the second housing member 3440. In particular, the connection portion 3462 of the membrane support 3460 is configured to connect to the exhaust gas orifice member 3470. The connection portion 3462 of the membrane support may be configured to form press fit connection with the exterior of the exhaust gas orifice member 3470. When the membrane support 3460 is connected to both the exhaust gas orifice member 3470 and the second housing member 3440, the membrane support flange 3464 may lie between the exhaust gas orifice member 3470 and the second housing member 3440.

5.3.4.7 Vibration Reduction

5.3.4.7.1 Damping Structure

The vent system 3400 in the example of FIGS. 9A to 10D includes a damping structure configured to damp vibration of the moveable portion 3456 of the membrane 3450. In these examples, the damping structure comprises a damping chamber 6050 within the vent housing 3402. By damping vibration of the moveable portion 3456 the damping chamber 6050 may reduce the noise generated by the membrane 3450 and emitted by the vent system 3400. The damping chamber 6050 may contain stagnant air (or other breathable gas). The damping chamber 6050 in these examples is a stagnant air cavity.

The vent housing 3402 may partially define the damping chamber 6050. In addition, the membrane 3450 may partially define the damping chamber 6050. As shown in FIGS. 9C-9G, 10C and 10D, the damping chamber 6050 is a cavity provided on the exterior side of the membrane 3450, in fluid communication with the pressurised volume 6000 in use and, when the membrane 3450 is stationary, is filled with gas having the same pressure as the pressurised volume 6000. The moveable portion 3456 of the membrane comprises a first side facing the membrane-facing surface 3424 and a second side opposite the first side partially defining the damping chamber 6050. The damping chamber 6050 may be further defined by one or more walls of the second housing member 3440. In various examples, one of the interior and the exterior of the moveable portion 3456 of the membrane 3450 faces the membrane-facing surface 3424 and the other of the interior and the exterior of the moveable portion 3456 of the membrane 3450 partially defines the damping chamber 6050.

The vent system 3400 may be configured such that movement of the moveable portion 3456 of the membrane 3450 increases or decreases a volume of the damping chamber 6050. Altering the volume of the damping chamber 6050 reduces the amount of air that can occupy the damping chamber 6050 at a particular pressure.

In these examples, the vent housing 3402 and damping chamber 6050 are configured to damp vibration of the moveable portion 3456 of the membrane 3450 by restricting gas exchange between the damping chamber 6050 and the pressurised volume 6000. A restriction in the exchange of gas between the damping chamber 6050 and the pressurised volume 6000 provides a damping effect to the membrane 3450 when the moveable portion 3456 of the membrane 3450 moves, causing an increase or decrease in the volume of the damping chamber 6050. As shown in FIGS. 9C-9G, the vent system 3400 may comprise at least one damping orifice 6055 through which gas is able to flow into and out of the damping chamber 6050. A damping chamber flow of gas into the damping chamber 6050 is indicated by 6206 in FIGS. 9F and 9G. The damping orifice 6055 may be shaped and/or sized to resist gas exchange between the damping chamber 6050 and the pressurised volume 6000.

If the moveable portion 3456 of the membrane 3450 begins to move away from the membrane-facing surface 3424, which would cause a reduction in the volume of the damping chamber 6050, a restriction on gas flow out of the damping chamber 6050 results in an increase in gas pressure within the damping chamber 6050. This increase in pressure in the damping chamber 6050 acts on the moveable portion 3456 of the membrane 3450 to slow its movement away from the membrane-facing surface 3424.

Conversely, if the moveable portion 3456 of the membrane 3450 begins to move towards the membrane-facing surface 3424, which would cause an increase in the volume of the damping chamber 6050, a restriction on gas flow into the damping chamber 6050 results in reduction in gas pressure within the damping chamber 6050. This reduction in pressure in the damping chamber 6050 acts on the moveable portion 3456 of the membrane 3450 to slow its movement towards the membrane-facing surface 3424.

In these examples, the restriction on gas flow between the pressurised volume 6000 and the damping chamber 6050 is not total occlusion preventing all gas exchange. The restriction on gas exchange into or out of the damping chamber 6050 may slow and/or smooth the movement of the moveable portion 3456 of the membrane 3450. However, the restriction on gas exchange will permit movement of the moveable portion 3456 of the membrane 3450 that results from non-vibratory forces, since pressure differences between the pressurised volume 6000 and the damping chamber 6050 will equalise over time. For example, if constant force is applied on the moveable portion 3456 of the membrane 3450 towards the membrane-facing surface 3424, the damping chamber 6050 may initially slow and/or smooth the movement of the moveable portion 3456 of the membrane 3450 towards the membrane-facing surface 3424. As gas slowly enters the damping chamber 6050, as illustrated in FIG. 9G by the damping chamber flow of gas 6206, the pressure in the damping chamber 6050 will equalise with the pressure in the pressurised volume 6000. The moveable portion 3456 of the membrane 3450 will then occupy a position closer to the membrane-facing surface 3424 without being pulled back by lower pressure in the damping chamber 6050. Accordingly, a damping effect is provided which resists and/or smooths unwanted movement of the moveable portion 3456 of the membrane 3450, such as vibrations which may be noisy.

As discussed above, the vent system 3400 may comprise at least one damping orifice 6055. The at least one damping orifice 6055 may be of a sufficiently small size to resist some gas exchange between the damping chamber 6050 and pressurised volume 6000. The damping orifices 6055 in a vent system 3400 may be of a particular size that is small enough to provide sufficient resistance to gas exchange but not so small as to reduce the functionality of the vent system 3400 (e.g. the ability of the moveable portion 3456 of the membrane 3450 to move towards or away from the membrane-facing surface 3424).

The actual size of each damping orifice 6055 in a particular vent system 3400 may be determined based on a number of factors such as: number of damping orifices 6055, dimensions of the damping chamber 6050 and membrane 3450, shape and dimensions of the vent housing 3402, shape and stiffness of the membrane 3450 and therapy pressure. An appropriate size for each damping orifice 6055 may be determined based on simulation, simple experimentation and/or trial-and-error. The vent system 3400 may comprise a plurality of damping orifices 6055 through which gas is able to flow into an out of the damping chamber 6050. The plurality of damping orifices 6055 may together define a sufficiently small combined cross-sectional area through which gas can flow, to resist gas exchange between the damping chamber 6050 and pressurised volume 6000.

As discussed above, the vent housing 3402 comprises a plurality of projections 3444 configured to prevent a free end of the membrane 3450 from moving towards the membrane-facing surface 3424. The vent housing 3402 may comprise a plurality of projections 3444 and a plurality of damping orifices 6055 defined between the plurality of projections 3444. Gas is able to flow through the damping orifices 6055 between the projections 3444 into and out of a damping chamber 6050 from the pressurised volume 6000, the damping orifices 6055 resisting gas exchange between the damping chamber 6050 and the pressurised volume 6000 to damp vibration of the moveable portion 3456 of the membrane

3450. FIGS. 9C to 9G and 10C to 10D show that the projections 3444 have small gaps between them, which form the damping orifices 6055 in these examples.

5.3.4.7.2 Restriction in Exhaust Gas Flow Path

In the exemplary vent system 3400 shown in FIGS. 9A to 9G, the exhaust gas flow passage 6002 comprises a region having a smaller cross-sectional area than adjacent regions in the exhaust gas flow passage 6002. In this example, the exhaust gas flow passage 6002 comprises a restriction 6006 in the exhaust gas flow path forming the region having a smaller cross-sectional area. The exhaust gas flow passage 6002 has a smaller cross-sectional area at the restriction 6006 than at other locations in the exhaust gas flow passage 6002. The membrane-facing surface 3424 may be closer to the moveable portion 3456 of the membrane 3450 at the restriction 6006 than at other locations in the exhaust gas flow passage 6002, resulting in a smaller cross-sectional area through which exhaust gas can flow through the exhaust gas flow passage 6002.

The restriction 6006 in the exhaust gas flow passage 6002 may be formed by a restrictor portion 3425, such as has been described above. In the example of FIGS. 9A to 9G, the restriction 6006 is formed by a restrictor portion 3425 in the form of contoured surfaces forming a rib on the first housing member 3430. The restrictor portion 3425 may be located centrally between a first end of the membrane 3450 and the second end of the membrane 3450.

The damping chamber 6050 may comprise a first end 6051 proximate the first end 3451 of the membrane 3450 and a second end 6052 proximate the second end 3452 of the membrane 3450. In the example of FIGS. 9A to 9G, the restriction 6006 in the exhaust gas flow passage 6002 is aligned centrally between the first end 6051 and the second end 6052 of the damping chamber 6050. Additionally, in this example the restriction 6006 in the exhaust gas flow passage 6005 is aligned centrally between the first end 3451 of the membrane 3450 and the second end 3452 of the membrane 3450. In this example, the restriction 6006 is aligned centrally along the longitudinal length of the moveable portion 3456 of the membrane 3450.

The restriction 6006 creates a region of the exhaust gas flow passage 6002 of minimum pressure compared to the pressure at other regions of the exhaust gas flow passage 6002 (which results from it having the smallest cross-sectional area in accordance with Bernoulli's Principle). Since the pressure in the exhaust gas flow passage 6002 is at a minimum at the restriction 6006, the force on the membrane 3450 towards the membrane-facing surface 3424 is larger at the restriction 6006 than elsewhere along the length of the membrane 3450. This point of maximum force on the membrane 3450 urges the moveable portion 3456 of the membrane 3450 to deform in a predictable manner. The moveable portion 3456 of the membrane 3450 may predictably deflect to a greater extent alongside the restriction 6006 than in comparison to elsewhere in the exhaust gas flow passage 6002. A membrane 3450 which deforms in this particular manner may be less susceptible to vibrations along the length of the membrane 3450, in comparison to a membrane 3450 provided alongside an exhaust gas flow passage 6002 of constant cross section and pressure along its length. Low vibration of the membrane 3450 may result in low noise levels emitted by the vent system 3400 and low fluctuations in pressure within the air circuit 4170 and/or patient interface 3000.

The vent housing 3402 may be configured such that any vibration of the moveable portion 3456 of the membrane 3450 that does occur, occurs predominantly in a first mode of vibration. The central location of the restriction 6006 with respect to the membrane 3450 may tune vibrations in the membrane 3450 to be predominantly in the first-mode of vibration. While vibrations in the membrane 3450 are to be minimised, it may be advantageous for any vibrations of the membrane 3450 that do occur to be predominantly first mode vibrations rather than higher mode vibrations.

The damping chamber 6050 extends substantially along the entire length of the membrane 3450 with the first end 6051 of the damping chamber 6050 proximate the first end 3451 of the membrane 3450 and a second end 6052 of the damping chamber 6050 proximate the second end 3452 of the membrane 3450, in the example of FIGS. 9A to 9G. An effect of this exemplary configuration is that first mode vibration of the membrane 3450 causes a change in volume of the entire damping chamber 6050 and acts to force gas into and out of the damping chamber 6050 during vibration through the damping orifices 6055.

If the membrane 3450 were to vibrate in higher modes, the change in the volume of the damping chamber 6050, if any, may be less pronounced. For example, if the membrane 3450 vibrates in its second mode, there may be little or no overall change in volume of the damping chamber 6050. The portion of the membrane 3450 between the first end 3451 of the membrane 3450 and a central point would move in one direction while the portion of the membrane 3450 between the central point and the second end 3452 of the membrane 3450 moves in the other direction. Any increase in volume of one half of the damping chamber 6050 may be accompanied by a corresponding reduction in volume of the other half of the damping chamber 6050. The gas inside the damping chamber 6050 would move from one end of the damping chamber 6050 to the other rather than being forced through the damping orifices 6055. There may be less of a damping effect in such a configuration, given less gas is forced in and out of the damping chamber 6050.

A vent system 3400 that is configured so that the membrane 3450 tends to vibrate predominantly in its first mode, if at all, may be relatively quiet due to the damping effect provided by the damping chamber 6050. In practice, some damping of vibration may still be achieved even if the vent system 3400 tolerates some second or higher mode vibrations. The damping chamber 6050 in the vent system 3400 shown in FIGS. 10A to 10D, even without a restriction in the exhaust gas flow passage 6002, may provide a damping effect due to any first mode vibrations of the membrane 3450 that do occur. Additionally, third mode vibrations may affect the volume of the damping chamber 6050, resulting in a damping effect. Furthermore, even without a restriction in the exhaust gas flow passage 6002, the damping chamber 6050 may function as a stagnant air cavity that is not largely affected by the flow of gas through the vent system 3400. Even if no damping is occurring, the damping chamber 6050 provides a higher pressure on the membrane 3450 opposite the low pressure region in the exhaust gas flow passage 6002, enabling the moveable portion to move towards the membrane-facing surface 3424 to regulate the vent flow of gas.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplemental oxygen. In one form, this allows for the direct measurement of a property of gases within the plenum chamber 3200, such as the pressure.

5.4 RPT DEVICE

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4100 capable of supplying air at positive pressure (e.g., a blower 4142), an outlet muffler 4124 and one or more transducers 4270, such as pressure sensors 4272 and flow rate sensors 4274.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a central controller, a therapy device controller 4240, a pressure generator 4100, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

As mentioned above, in some forms of the present technology, the central controller may be configured to implement one or more algorithms 4300 expressed as computer programs stored in a non-transitory computer readable storage medium, such as memory 4260. The algorithms 4300 are generally grouped into groups referred to as modules.

An RPT device in accordance with one form of the present technology may include an air filter 4110, or a plurality of air filters 4110.

In one form, an outlet air filter 4114, for example an antibacterial filter, is located between an outlet of the pneumatic block 4020 and a patient interface 3000.

An RPT device in accordance with one form of the present technology may include a muffler 4120, or a plurality of mufflers 4120.

In one form of the present technology, an anti-spillback valve 4160 is located between the humidifier 5000 and the pneumatic block 4020. The anti-spillback valve is constructed and arranged to reduce the risk that water will flow upstream from the humidifier 5000, for example to the motor 4144.

5.4.1.1 Pre-Processing Module

A pre-processing module 4310 in accordance with one form of the present technology receives as an input a signal from a transducer 4270, for example a flow rate sensor 4274 or pressure sensor 4272, and performs one or more process steps to calculate one or more output values that will be used as an input to another module, for example a therapy engine module 4320.

In one form of the present technology, the output values include the interface or mask pressure Pm, the respiratory flow rate Qr, and the leak flow rate Ql.

In various forms of the present technology, the pre-processing module 4310 comprises one or more of the following algorithms: pressure compensation 4312, vent flow rate estimation 4314, leak flow rate estimation 4316, and respiratory flow rate estimation 4318.

5.4.1.1.1 Pressure Compensation

In one form of the present technology, a pressure compensation algorithm 4312 receives as an input a signal indicative of the pressure in the pneumatic path proximal to an outlet of the pneumatic block. The pressure compensation algorithm 4312 estimates the pressure drop through the air circuit 4170 and provides as an output an estimated pressure, Pm, in the patient interface 3000.

5.4.1.1.2 Vent Flow Rate Estimation

In one form of the present technology, a vent flow rate estimation algorithm 4314 receives as an input an estimated pressure, Pm, in the patient interface 3000 and estimates a vent flow rate of air, Qv, from a vent system 3400 in a patient interface 3000.

5.4.1.1.3 Leak Flow Rate Estimation

In one form of the present technology, a leak flow rate estimation algorithm 4316 receives as an input a total flow rate, Qt, and a vent flow rate Qv, and provides as an output an estimate of the leak flow rate Ql. In one form, the leak flow rate estimation algorithm estimates the leak flow rate Ql by calculating an average of the difference between total flow rate Qt and vent flow rate Qv over a period sufficiently long to include several breathing cycles, e.g. about 10 seconds.

In one form, the leak flow rate estimation algorithm 4316 receives as an input a total flow rate Qt, a vent flow rate Qv, and an estimated pressure, Pm, in the patient interface 3000, and provides as an output a leak flow rate Ql, by calculating a leak conductance, and determining a leak flow rate Ql to be a function of leak conductance and pressure, Pm. Leak conductance is calculated as the quotient of low pass filtered non-vent flow rate equal to the difference between total flow rate Qt and vent flow rate Qv, and low pass filtered square root of pressure Pm, where the low pass filter time constant has a value sufficiently long to include several breathing cycles, e.g. about 10 seconds. The leak flow rate Ql may be estimated as the product of leak conductance and a function of pressure, Pm.

5.4.1.1.4 Respiratory Flow Rate Estimation

In one form of the present technology, a respiratory flow rate estimation algorithm 4318 receives as an input a total flow rate, Qt, a vent flow rate, Qv, and a leak flow rate, Ql, and estimates a respiratory flow rate of air, Qr, to the patient, by subtracting the vent flow rate Qv and the leak flow rate Ql from the total flow rate Qt.

5.4.1.2 Therapy Engine Module

In one form of the present technology, a therapy engine module 4320 receives as inputs one or more of a pressure, Pm, in a patient interface 3000, and a respiratory flow rate of air to a patient, Qr, and provides as an output one or more therapy parameters.

5.4.1.3 Therapy Control Module

The therapy control module 4330 in accordance with one aspect of the present technology receives as inputs the therapy parameters from the therapy parameter determination algorithm 4329 of the therapy engine module 4320, and controls the pressure generator 4100 to deliver a flow of air in accordance with the therapy parameters.

In one form of the present technology, the therapy parameter is a treatment pressure Pt, and the therapy control module 4330 controls the pressure generator 4100 to deliver a flow of air whose mask pressure Pm at the patient interface 3000 is equal to the treatment pressure Pt.

5.5 AIR CIRCUIT

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

FIG. 13 depicts various configurations for incorporating the exemplary vent systems 3400 with various patient interfaces 3000A-C.

The first housing member 3430 of the vent housing 3402 may provide an interface for connecting the vent system 3400 to an air circuit connector 4171 to join the vent system 3400 with the air circuit 4170 and locate the vent system 3400 within the flow path. In this example, the inlet connection portion 3416 of the first housing member 3430 enables the vent housing 3402 to be fluidly connect to the air circuit 4170.

The second housing member 3440 of the vent housing 3402 may provide an interface for connecting the vent system 3400 to a vent connector tube 4180 at a tube connector 4182. The vent connector tube 4180 may be known as a short tube. In this example, the outlet connection portion 3420 of the second housing member 3440 is configured to fluidly connect the vent housing 3402 to the vent connector tube elbow 4181.

The vent connector tube 4180 may be connected to a nasal patient interface 3000A, which may be configured to seal against at least a lower periphery of the patient's nose or which may be configured to receive at the least the tip of the patient's nose to seal around the nose, or a nasal pillows patient interface 3000B, which may include a pillow on a stalk for sealing with each naris, opposite the tube connector 4182 via a vent connector tube elbow 4181. The vent connector tube 4180 may be lighter and/or have a smaller diameter than the air circuit 4170, because such a configuration allows the vent system 3400 to be spaced away from the patient interface 3000A/3000B to reduce tube drag. In the case of a full-face patient interface 3000C, which may be configured to seal against the patient's face around the nose and mouth together such that gas directed to the patient's nose and mouth through a single opening or which may be configured as an ultra-compact full-face patient interface with one or two openings to direct gas to the patient's nares and another opening to direct gas to the patient's mouth, the vent connector tube 4180 may be excluded and the outer wall of the vent housing 3402 may be joined to the decoupling structure 3500.

In any of these configurations, a heat and moisture exchanger (HMX) (not shown) may also be included. For example, an HMX may be provided between the patient interface 3000 and the vent connector tube 4180 or between the tube connector 4182 and the vent system 3400. Alternatively, an HMX may be positioned within the plenum chamber 3200. In any of these HMX configurations, the HMX may be positioned between the patient's airways and the vent system 3400 so that exhaled gas can deposit its heat and moisture to the HMX material before being vented to atmosphere.

5.6 HUMIDIFIER

5.6.1 Humidifier Overview

Figure 1A:
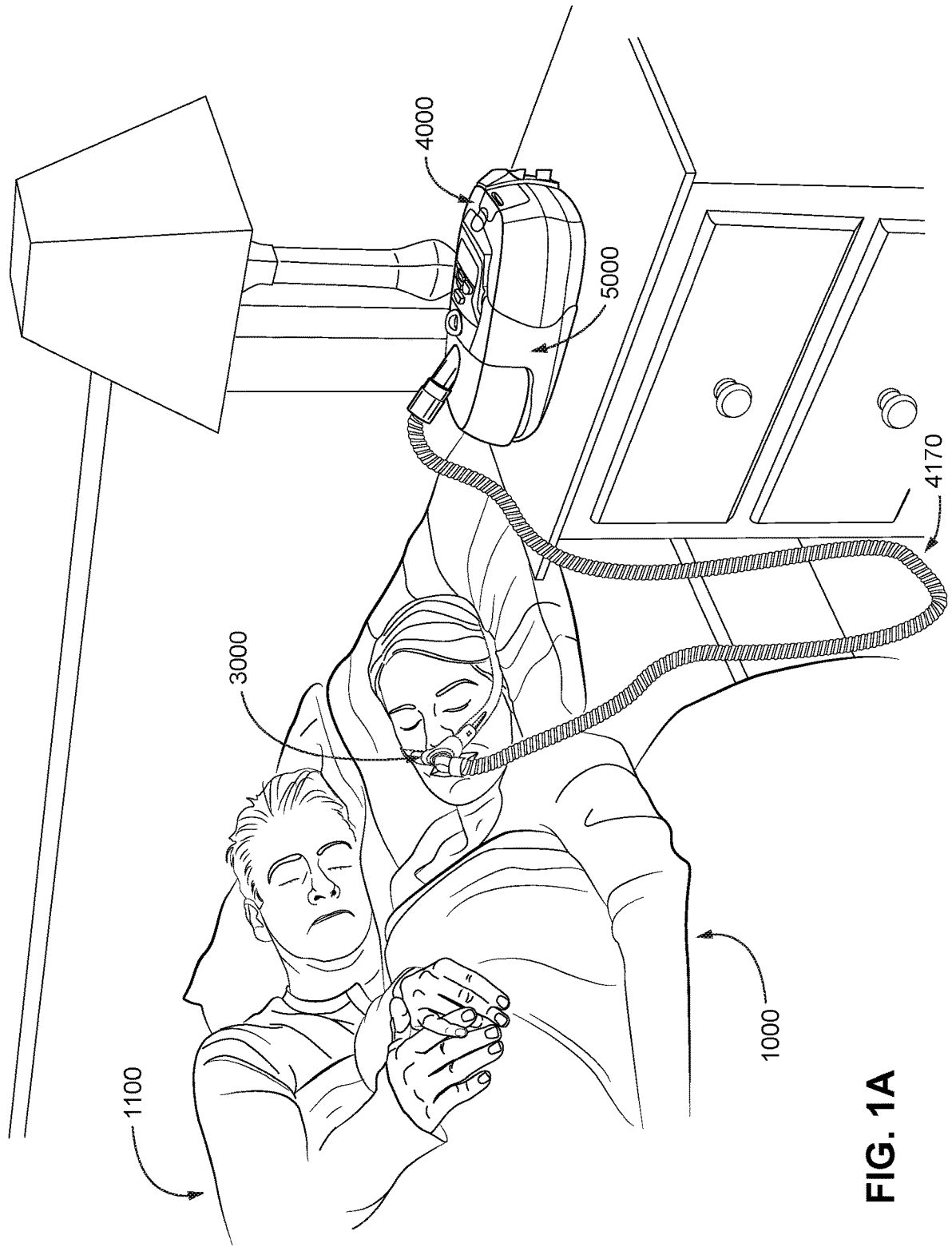
Figure 1B:
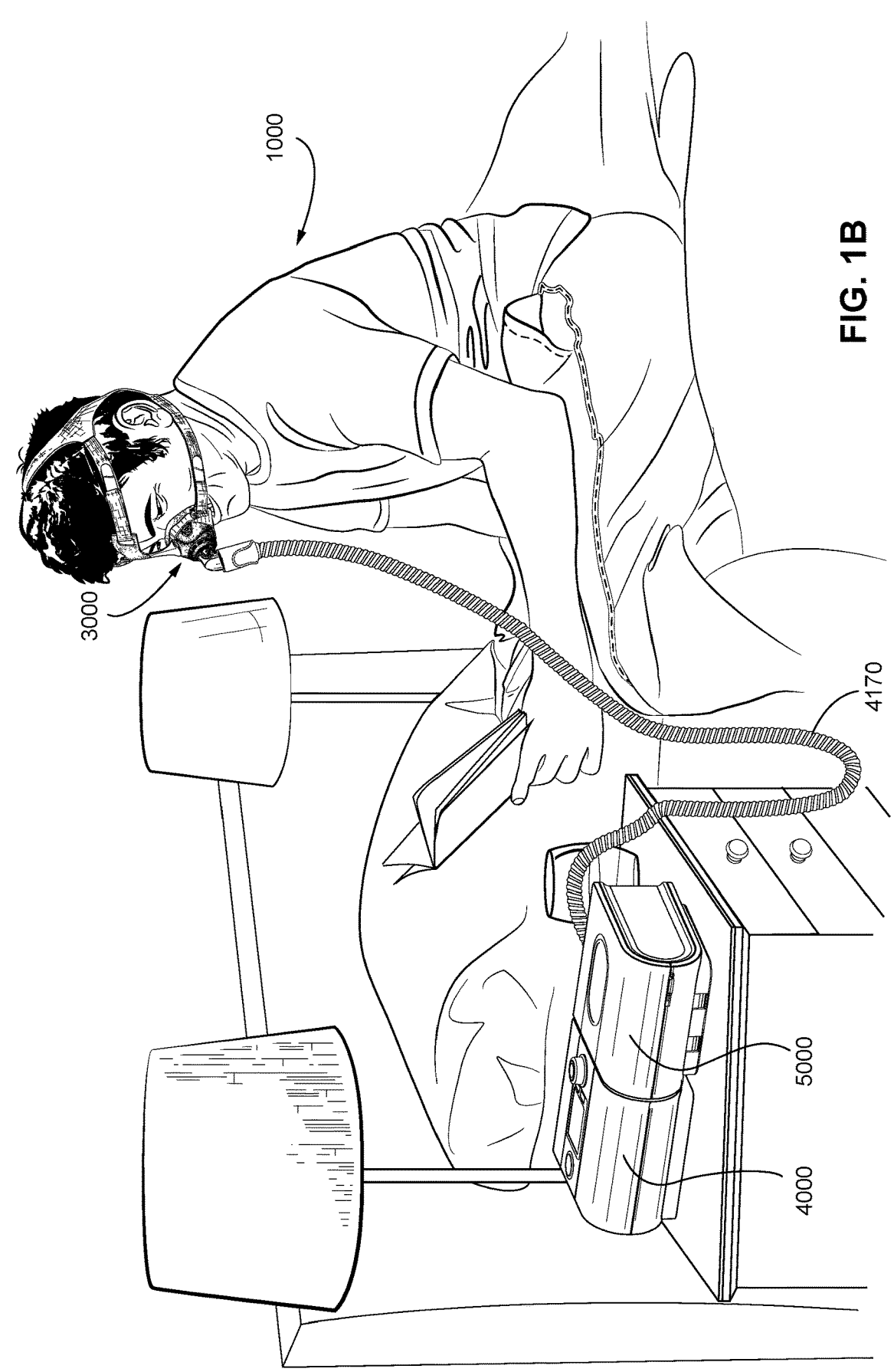
Figure 1C:
Figure 2A:
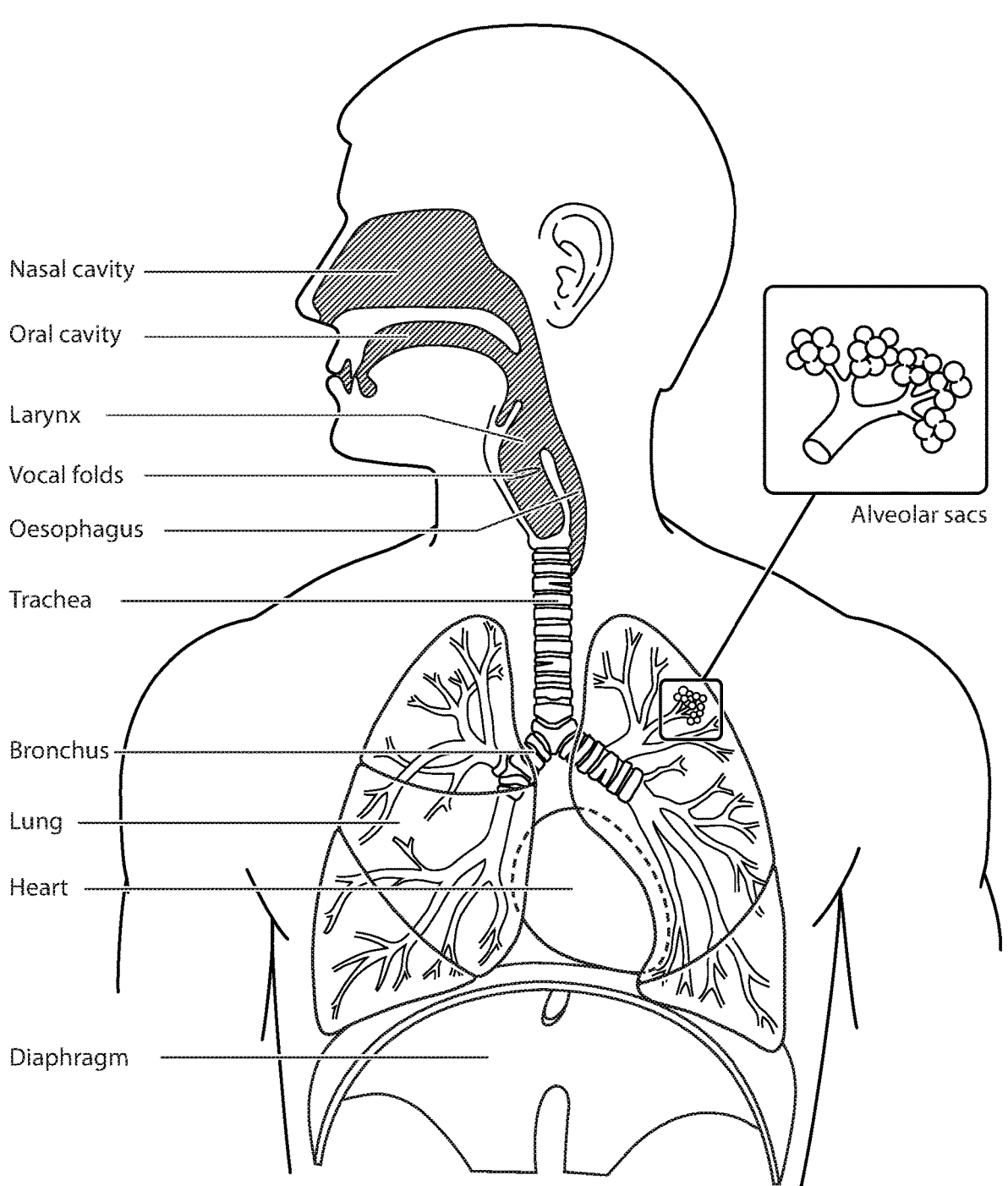
Figure 3A:
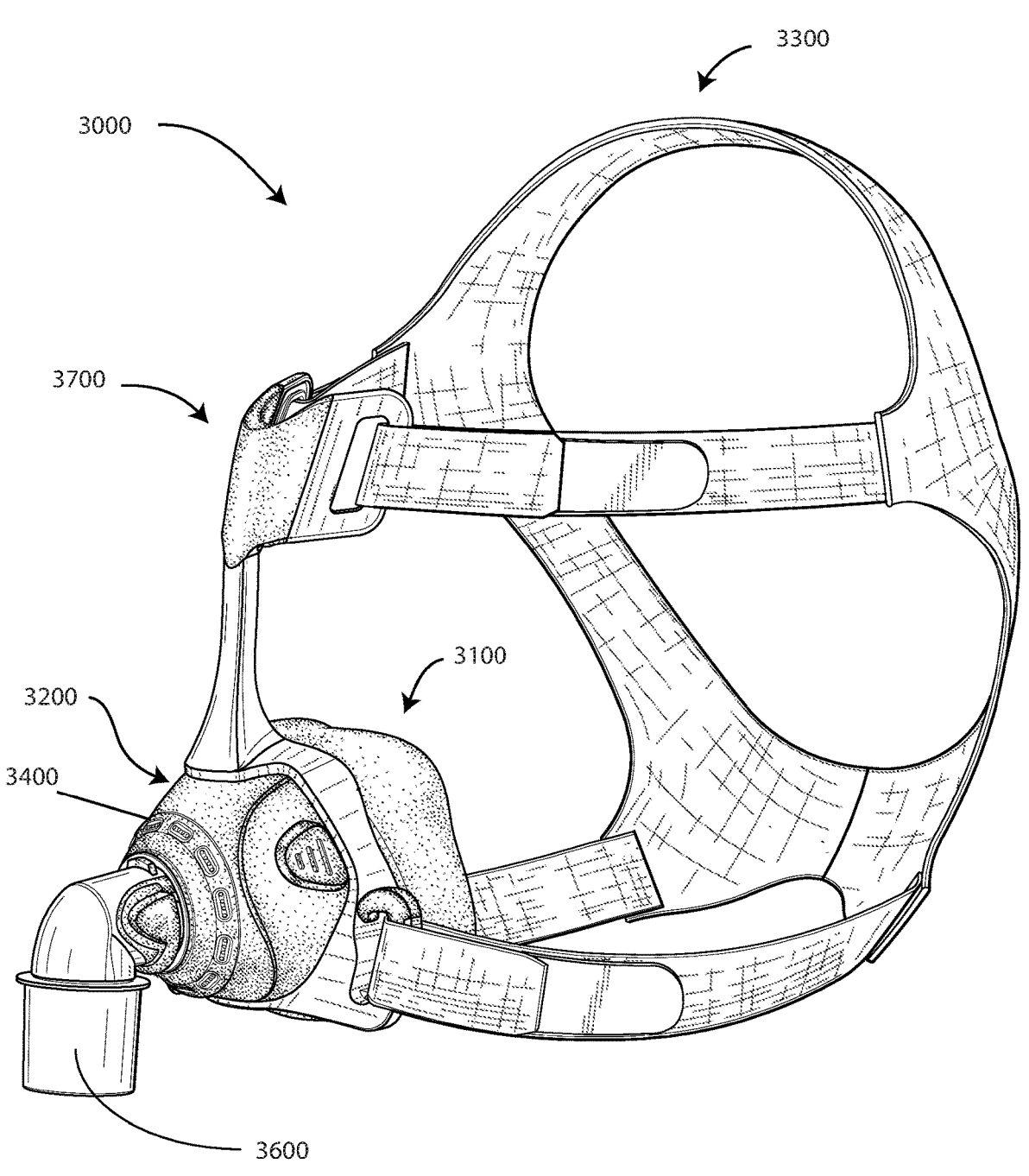
Figure 4A:
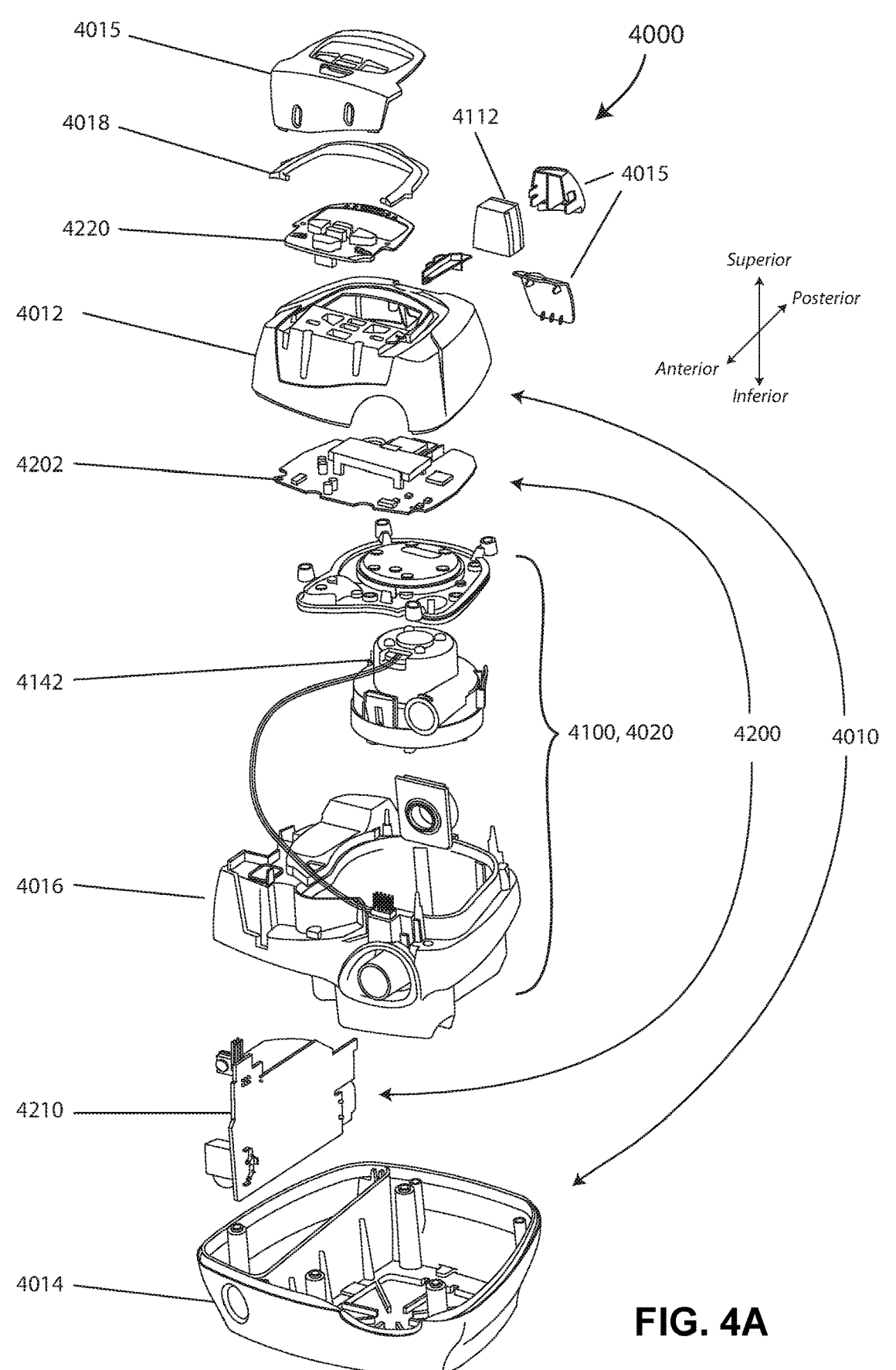
Figure 4B:
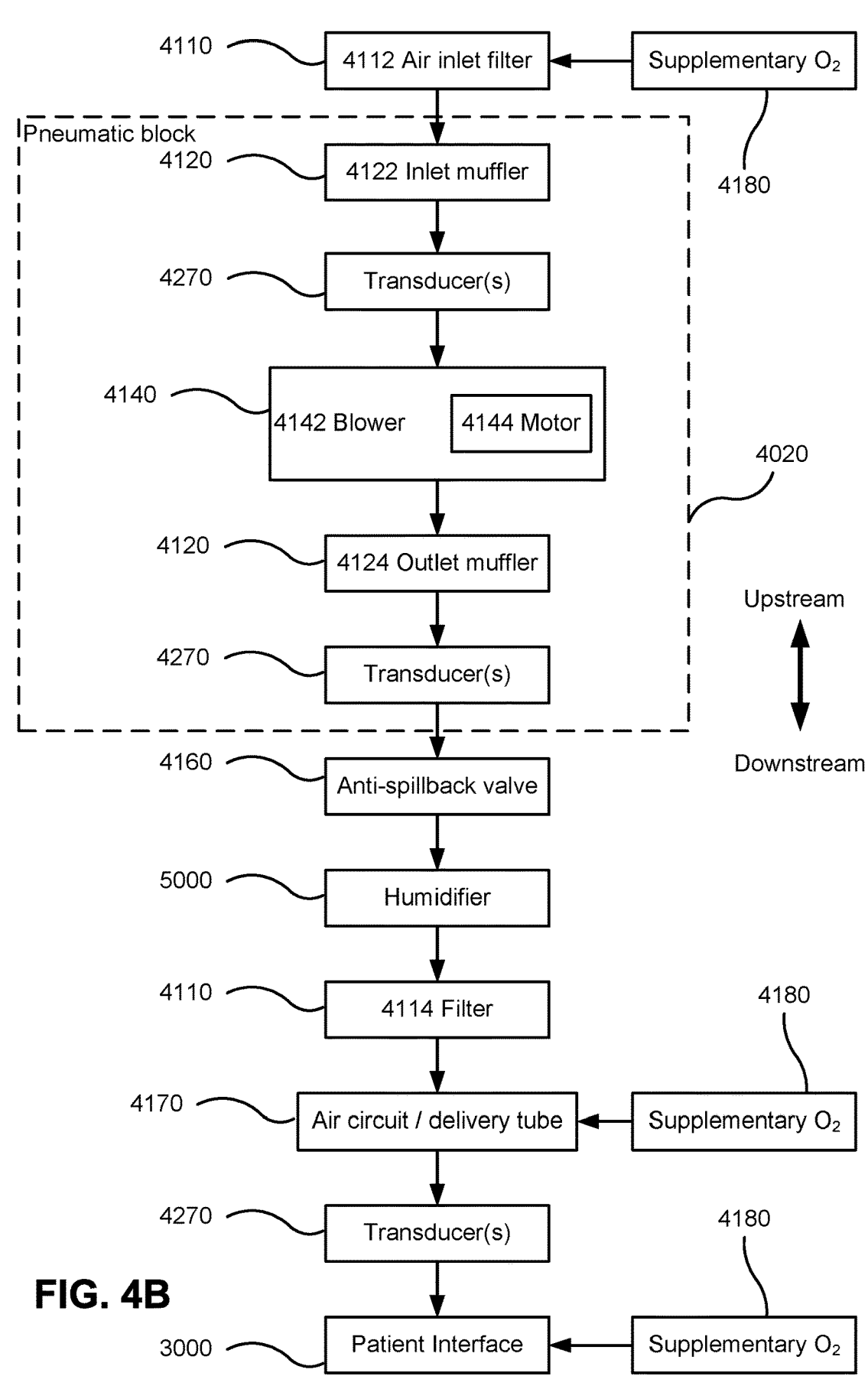
Figure 5A:
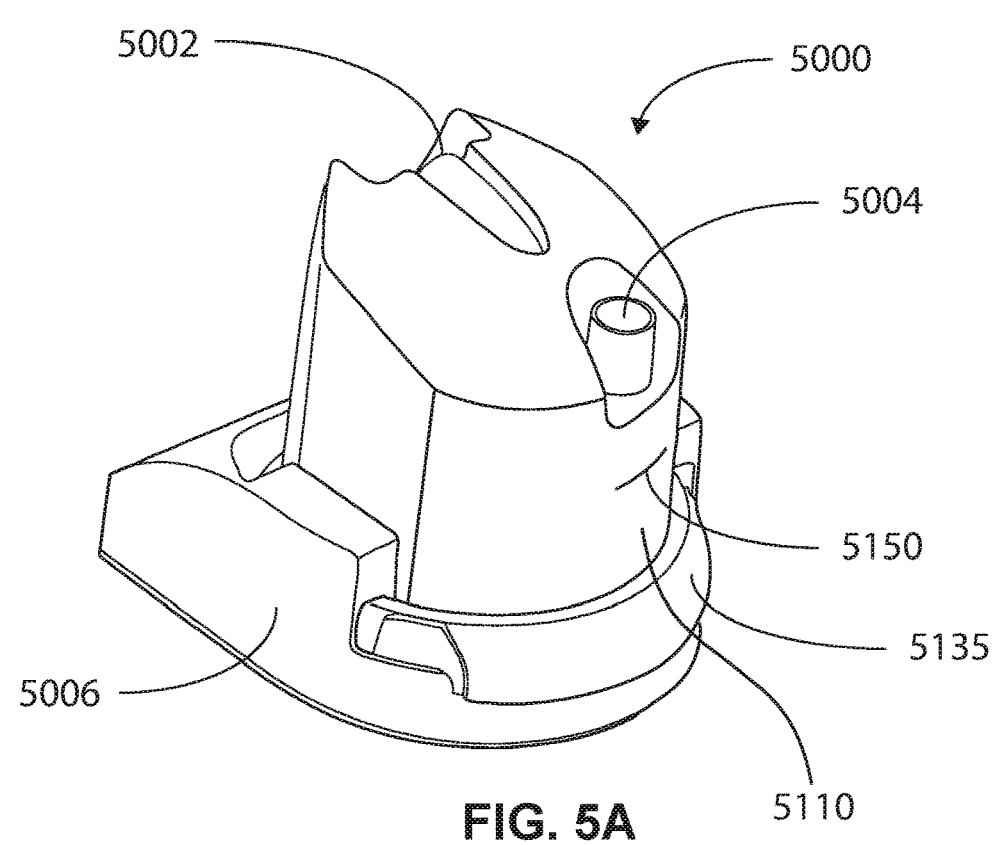
FIG. 5A shows an isometric view of a humidifier in accordance with one form of the present technology.

In one form of the present technology there is provided a humidifier 5000 (e.g. as shown in FIG. 5A) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

Figure 5B:
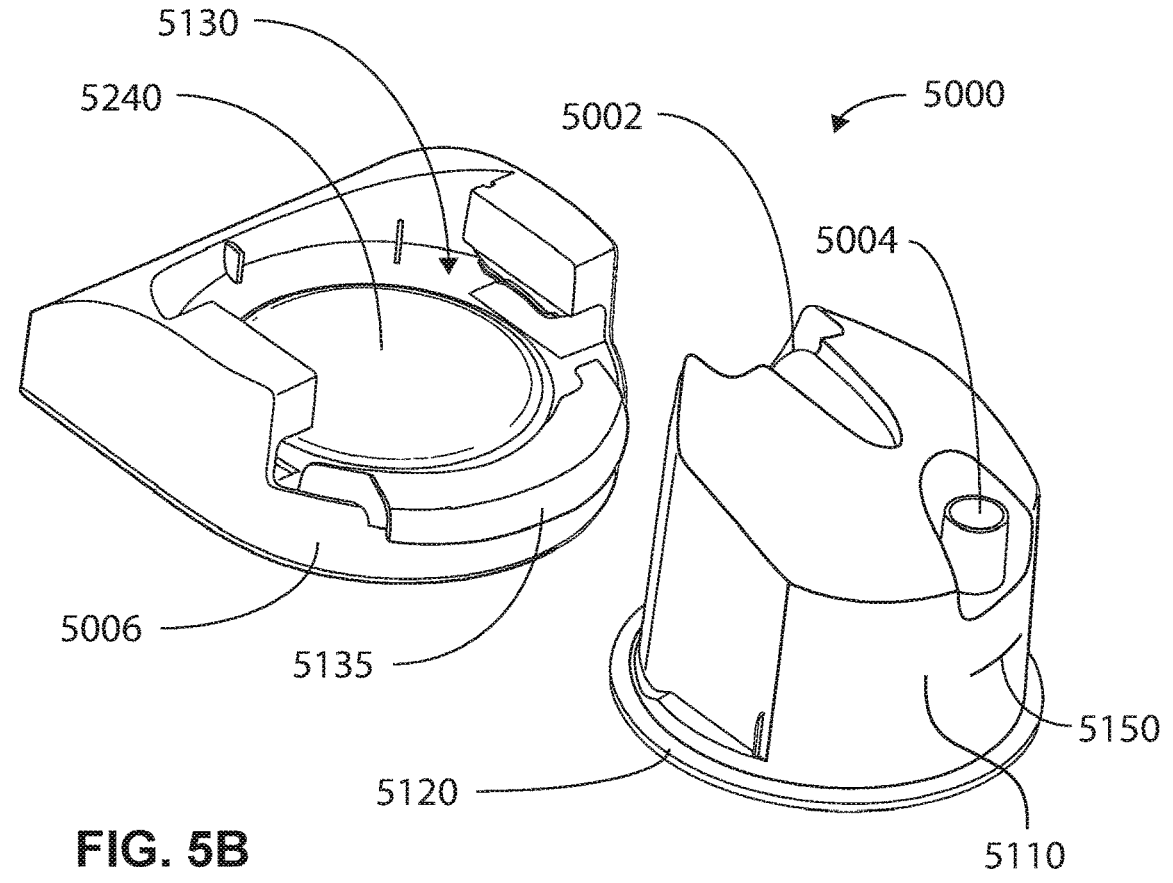
FIG. 5B shows an isometric view of a humidifier in accordance with one form of the present technology, showing a humidifier reservoir 5110 removed from the humidifier reservoir dock 5130.
Figure 5C:
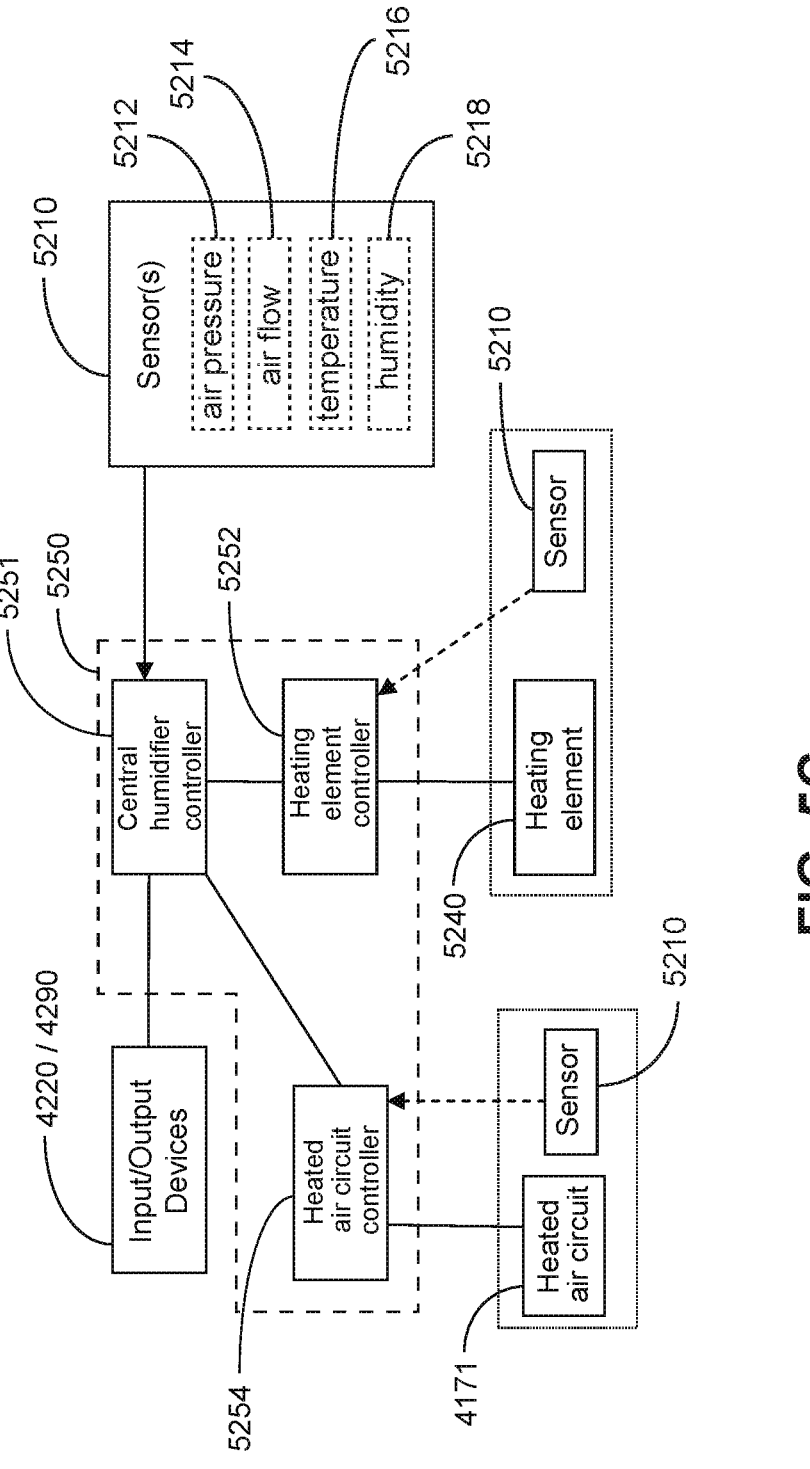
FIG. 5C shows a schematic of a humidifier in accordance with one form of the present technology.

The humidifier 5000 may comprise a humidifier reservoir 5110, a humidifier inlet 5002 to receive a flow of air, and a humidifier outlet 5004 to deliver a humidified flow of air. In some forms, as shown in FIG. 5A and FIG. 5B, an inlet and an outlet of the humidifier reservoir 5110 may be the humidifier inlet 5002 and the humidifier outlet 5004 respectively. The humidifier 5000 may further comprise a humidifier base 5006, which may be adapted to receive the humidifier reservoir 5110 and comprise a heating element 5240.

5.6.2 Humidifier Components

5.6.2.1 Water Reservoir

According to one arrangement, the humidifier 5000 may comprise a water reservoir 5110 configured to hold, or retain, a volume of liquid (e.g. water) to be evaporated for humidification of the flow of air. The water reservoir 5110 may be configured to hold a predetermined maximum volume of water in order to provide adequate humidification for at least the duration of a respiratory therapy session, such as one evening of sleep. Typically, the reservoir 5110 is configured to hold several hundred millilitres of water, e.g. 300 millilitres (ml), 325 ml, 350 ml or 400 ml. In other forms, the humidifier 5000 may be configured to receive a supply of water from an external water source such as a building's water supply system.

According to one aspect, the water reservoir 5110 is configured to add humidity to a flow of air from the RPT device 4000 as the flow of air travels therethrough. In one form, the water reservoir 5110 may be configured to encourage the flow of air to travel in a tortuous path through the reservoir 5110 while in contact with the volume of water therein.

According to one form, the reservoir 5110 may be removable from the humidifier 5000, for example in a lateral direction as shown in FIG. 5A and FIG. 5B.

The reservoir 5110 may also be configured to discourage egress of liquid therefrom, such as when the reservoir 5110 is displaced and/or rotated from its normal, working orientation, such as through any apertures and/or in between its sub-components. As the flow of air to be humidified by the humidifier 5000 is typically pressurised, the reservoir 5110 may also be configured to prevent losses in pneumatic pressure through leak and/or flow impedance.

5.6.2.2 Conductive Portion

According to one arrangement, the reservoir 5110 comprises a conductive portion 5120 configured to allow efficient transfer of heat from the heating element 5240 to the volume of liquid in the reservoir 5110. In one form, the conductive portion 5120 may be arranged as a plate, although other shapes may also be suitable. All or a part of the conductive portion 5120 may be made of a thermally conductive material such as aluminium (e.g. approximately 2 mm thick, such as 1 mm, 1.5 mm, 2.5 mm or 3 mm), another heat conducting metal or some plastics. In some cases, suitable heat conductivity may be achieved with less conductive materials of suitable geometry.

5.6.2.3 Humidifier Reservoir Dock

In one form, the humidifier 5000 may comprise a humidifier reservoir dock 5130 (as shown in FIG. 5B) configured to receive the humidifier reservoir 5110. In some arrangements, the humidifier reservoir dock 5130 may comprise a locking feature such as a locking lever 5135 configured to retain the reservoir 5110 in the humidifier reservoir dock 5130.

5.6.2.4 Water Level Indicator

The humidifier reservoir 5110 may comprise a water level indicator 5150 as shown in FIG. 5A-5B. In some forms, the water level indicator 5150 may provide one or more indications to a user such as the patient 1000 or a care giver regarding a quantity of the volume of water in the humidifier reservoir 5110. The one or more indications provided by the water level indicator 5150 may include an indication of a maximum, predetermined volume of water, any portions thereof, such as 25%, 50% or 75% or volumes such as 200 ml, 300 ml or 400 ml.

5.7 BREATHING WAVEFORMS

FIG. 6A shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak –0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 SCREENING, DIAGNOSIS, MONITORING SYSTEMS

5.8.1 Polysomnography

FIG. 7A shows a patient 1000 undergoing polysomnography (PSG). A PSG system comprises a headbox 2000 which receives and records signals from the following sensors: an EOG electrode 2015; an EEG electrode 2020; an ECG electrode 2025; a submental EMG electrode 2030; a snore sensor 2035; a respiratory inductance plethysmogram (respiratory effort sensor) 2040 on a chest band; a respiratory inductance plethysmogram (respiratory effort sensor) 2045 on an abdominal band; an oro-nasal cannula 2050 with oral thermistor; a photoplethysmograph (pulse oximeter) 2055; and a body position sensor 2060. The electrical signals are referred to a ground electrode (ISOG) 2010 positioned in the centre of the forehead.

5.8.2 Non-Obtrusive Monitoring System

One example of a monitoring apparatus 7100 for monitoring the respiration of a sleeping patient 1000 is illustrated in FIG. 7B. The monitoring apparatus 7100 contains a contactless motion sensor generally directed toward the patient 1000. The motion sensor is configured to generate one or more signals representing bodily movement of the patient 1000, from which may be obtained a signal representing respiratory movement of the patient.

5.9 GLOSSARY

For the purposes of the present technology disclosure, in certain forms of the present technology, one or more of the following definitions may apply. In other forms of the present technology, alternative definitions may apply.

5.9.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Total flow rate, Qt, is the flow rate of air leaving the RPT device. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Patient: A person, whether or not they are suffering from a respiratory condition.

Pressure: Force per unit area. Pressure may be expressed in a range of units, including $cmH_2O$, g-f/cm$^2$ and hectopascal. $1 cmH_2O$ is equal to $1 g-f/cm^2$ and is approximately 0.98 hectopascal. In this specification, unless otherwise stated, pressure is given in units of $cmH_2O$.

The pressure in the patient interface is given the symbol Pm, while the treatment pressure, which represents a target value to be achieved by the mask pressure Pm at the current instant of time, is given the symbol Pt.

Respiratory Pressure Therapy (RPT): The application of a supply of air to an entrance to the airways at a treatment pressure that is typically positive with respect to atmosphere.

Ventilator: A mechanical device that provides pressure support to a patient to perform some or all of the work of breathing.

5.9.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240.

Polycarbonate: a thermoplastic polymer of Bisphenol-A Carbonate.

5.9.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions.

Floppy structure or component: A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 $cmH_2O$ pressure.

As an example, an I-beam may comprise a different bending stiffness (resistance to a bending load) in a first direction in comparison to a second, orthogonal direction. In another example, a structure or component may be floppy in a first direction and rigid in a second direction.

5.9.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:

(i) Flattened: Having a rise followed by a relatively flat portion, followed by a fall.

(ii) M-shaped: Having two local peaks, one at the leading edge, and one at the trailing edge, and a relatively flat portion between the two peaks.

(iii) Chair-shaped: Having a single local peak, the peak being at the leading edge, followed by a relatively flat portion.

(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peakflow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.9.3 Anatomy

5.9.3.1 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.9.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear: Headgear will be taken to mean a form of positioning and stabilizing structure designed for use on a head. For example the headgear may comprise a collection of one or more struts, ties and stiffeners configured to locate and retain a patient interface in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.10 OTHER REMARKS

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.11 REFERENCE SIGNS LIST

1000 Patient
1100 Bed partner

3000 Patient interface
3100 Seal-forming structure
3200 Plenum chamber
3300 Positioning and stabilising structure
3400 Vent system
3402 Vent housing
3404 First end of the vent housing
3405 Second end of the vent housing
3406 Longitudinal axis of the vent housing
3407 Inlet
3408 Outlet
3416 Inlet connection portion
3418 Bayonet fitting
3420 Outlet connection portion
3422 Internal channel
3424 Membrane-facing surface
3425 Restrictor portion
3430 First housing member
3431 First end of the first housing member
3432 Second end of the first housing member
3433 Rounded surface
3434 Shaft
3435 Flange
3436 Flange projections
3437 Diffuser retaining rim
3438 Second housing member connection portion
3440 Second housing member
3441 First end of the second housing member
3442 Second end of the second housing member
3444 Projection
3446 Membrane stop flange
3448 Diffuser retaining portion
3450 Membrane
3451 First end of the membrane
3452 Second end of the membrane
3454 Longitudinal axis of the membrane
3456 Moveable portion of the membrane
3460 Membrane support
3462 Connection portion
3464 Membrane support flange
3465 Baffle portion
3466 First end of the baffle portion
3467 Second end of the baffle portion
3468 Baffle flange
3470 Exhaust gas orifice member
3471 Diffused exhaust gas orifice
3472 Undiffused exhaust gas orifice
3473 Common exhaust gas orifice
3474 Diffuser member
3475 Intermediate exhaust gas flow orifice
3476 First end of the exhaust gas orifice member
3477 Second end of the exhaust gas orifice member
3478 Intermediate exhaust gas orifice
3600 Connection port
3700 Forehead support
4000 RPT device
4010 External housing
4012 Upper portion
4014 Lower portion
4015 Panel
4016 Chassis
4018 Handle
4020 Pneumatic block
4100 Pressure generator
4110 Air filter
4112 Inlet air filter
4114 Outlet air filter 4120 Muffler
4122 Inlet muffler
4124 Outlet muffler
4142 Blower
4144 Motor
4160 Anti-spill back valve
4170 Air circuit
4171 Air circuit connector
4180 Vent connector tube
4181 Vent connector tube elbow
4182 Tube connector
4200 Electrical components
4202 Printed Circuit Board Assembly (PCBA)
4210 Electrical power supply
4220 Input device
4240 Therapy device controller
4250 Protection circuit
4260 Memory
4270 Transducer
4272 Pressure sensor
4274 Flow rate sensor
4280 Data communication interface
4290 Output devices
4300 Algorithm
4310 Pre-processing module
4312 Pressure compensation
4314 Vent flow rate estimation
4316 Leak flow rate estimation
4318 Respiratory flow rate estimation
4320 Therapy engine module
4330 Therapy control module
4329 Therapy parameter determination algorithm
5000 Humidifier
5002 Humidifier inlet
5004 Humidifier outlet
5006 Humidifier base
5110 Humidifier reservoir
5120 Conductive portion
5130 Humidifier reservoir dock
5135 Locking lever
5150 Water level indicator
5240 Heating element
6000 Pressurised volume
6002 Exhaust gas flow passage
6004 Exhaust gas flow passage inlet
6006 Restriction
6040 Stagnant air cavity
6050 Damping chamber
6051 First end of the damping chamber
6052 Second end of the damping chamber
6055 Damping orifice
6100 Atmosphere
6201 Flow of gas from RPT device
6202 Therapy flow of gas
6203 Vent flow of gas
6204 Diffused vent flow of gas
6205 Undiffused vent flow of gas
6206 Damping chamber flow of gas

The invention claimed is:

1. A patient interface comprising:
a plenum chamber at least partially forming a volume pressurisable to a therapeutic pressure of at least 6 cmH$_2$O above ambient air pressure throughout a patient's respiratory cycle in use, and the plenum chamber including a plenum chamber inlet port sized and structured to receive a therapy flow of gas for breathing by a patient, a seal-forming structure constructed and arranged to seal with a region of the patient's face surrounding an entrance to the patient's airways, the seal-forming structure having a hole to deliver the therapy flow of gas to the entrance to the patient's airways during use, and the seal-forming structure being constructed and arranged to maintain the therapeutic pressure in the plenum chamber throughout the patient's respiratory cycle in use;

a positioning and stabilising structure comprising a strap configured to hold the seal-forming structure in a therapeutically effective position on the patient's head;

a vent structure comprising:

a vent housing comprising an inlet configured to be connected to a supply conduit to receive a flow of gas from a respiratory pressure therapy device, an outlet configured to supply the therapy flow of gas to the plenum chamber inlet port, and at least one exhaust gas orifice configured to discharge a vent flow of gas to atmosphere, and the at least one exhaust gas orifice being sized and shaped to discharge a vent flow of gas to atmosphere continuously throughout the patient's respiratory cycle and maintain the therapeutic pressure in the plenum chamber in use; and a membrane positioned within the vent housing and extending circumferentially around a longitudinal axis of the vent housing, the membrane having a first end and a second end spaced apart along a longitudinal axis of the membrane, and the membrane having a moveable portion positioned between the first end of the membrane and the second end of the membrane and surrounding the longitudinal axis of the membrane;

wherein the moveable portion of the membrane is spaced radially, with respect to the longitudinal axis of the membrane, from a membrane-facing surface extending circumferentially around an inside of the vent housing to form an exhaust gas flow passage between the moveable portion of the membrane and the membrane-facing surface, and the exhaust gas flow passage being configured to allow gas to flow from the volume at least partially formed by the plenum chamber through the exhaust gas flow passage to atmosphere via the at least one exhaust gas orifice during use, wherein the moveable portion of the membrane is elastically deformable and is configured to move radially relative to the membrane-facing surface in response to differences in pressure throughout a therapeutic pressure range between an interior side of the membrane and an exterior side of the membrane to change a cross-sectional area of the exhaust gas flow passage; and wherein the patient interface is configured to allow the patient to breathe from ambient through their mouth in the absence of a flow of pressurised air through the plenum chamber inlet port, or the patient interface is configured to leave the patient's mouth uncovered.

2. The patient interface of claim 1, wherein the moveable portion of the membrane is an annulus that is substantially cylindrical or frustoconical in shape.

3. The patient interface of claim 1, wherein the vent housing comprises a first end and a second end aligned along a longitudinal axis of the vent housing, the longitudinal axis of the membrane being aligned with the longitudinal axis of the vent housing.

4. The patient interface of claim 3, wherein the moveable portion of the membrane comprises one or more walls aligned parallel to the flow of gas through the vent housing from the first end of the vent housing to the second end of the vent housing.

5. The patient interface of claim 3, wherein the vent housing comprises a first housing member at the first end of the vent housing and a second housing member at the second end of the vent housing, and the first housing member and the second housing member being configured to connect together.

6. The patient interface of claim 5, wherein the first housing member comprises an inlet connection portion configured to fluidly connect the vent structure to the supply conduit.

7. The patient interface of claim 5, wherein the second housing member comprises an outlet connection portion configured to fluidly connect the vent structure to the patient interface or to a tube configured to be connected to the patient interface.

8. The patient interface of claim 1, wherein the membrane is joined to a membrane support at the first end of the membrane.

9. The patient interface of claim 1, wherein the moveable portion of the membrane is formed from silicone rubber.

10. The patient interface of claim 1, wherein the vent structure comprises a damping structure comprising a damping chamber within the vent housing configured to damp vibration of the moveable portion of the membrane.

11. The patient interface of claim 10, wherein the vent housing at least partially forms the damping chamber.

12. The patient interface of claim 10, wherein one of the interior side and the exterior side of the membrane faces the membrane-facing surface and the other of the interior side and the exterior side of the membrane at least partially forms the damping chamber.

13. The patient interface of claim 10, wherein the damping chamber is in fluid communication with the volume at least partially formed by the plenum chamber.

14. The patient interface of claim 10, wherein the vent structure is configured such that movement of the moveable portion of the membrane increases or decreases a volume of the damping chamber.

15. The patient interface of claim 14, wherein the vent housing and damping chamber are configured to damp vibration of the moveable portion of the membrane by restricting gas exchange between the damping chamber and the volume at least partially formed by the plenum chamber.

16. The patient interface of claim 1, wherein the exhaust gas flow passage comprises a restriction region having a smaller cross-sectional area than adjacent regions of the exhaust gas flow passage.

17. The patient interface of claim 16, wherein the membrane-facing surface is closest to the moveable portion of the membrane at the restriction region.

18. The patient interface of claim 16, wherein the membrane-facing surface comprises a restrictor portion forming the restriction region in the exhaust gas flow passage.

19. The patient interface of claim 18, wherein the membrane-facing surface comprises contoured surfaces forming the restrictor portion.

20. The patient interface of claim 18, wherein the restrictor portion comprises a rib in the membrane-facing surface.

21. The patient interface of claim 18, wherein the restrictor portion is located centrally between the first end of the membrane and the second end of the membrane.

22. The patient interface of claim 18, comprising a damping chamber within the vent housing configured to damp vibration of the moveable portion of the membrane, wherein the damping chamber comprises a first end proximal to the first end of the membrane and a second end proximal to the second end of the membrane, and the restriction region in the exhaust gas flow passage being aligned centrally between the first end of the damping chamber and the second end of the damping chamber.

23. The patient interface of claim 1, wherein the vent housing is configured to reduce vibration of the moveable portion of the membrane in modes of vibration higher than a first mode of vibration.

24. The patient interface of claim 1, wherein the vent housing is configured to limit movement of the moveable portion of the membrane towards the membrane-facing surface during use.

25. The patient interface of claim 24, wherein the vent housing is configured to contact an end of the membrane and prevent the end of the membrane from moving towards the membrane-facing surface during use.

26. The patient interface of claim 25, wherein the vent housing comprises at least one projection configured to contact the end of the membrane to limit movement of the end of the membrane during use.

27. The patient interface of claim 26, wherein the at least one projection is positioned outside of the exhaust gas flow passage.

28. The patient interface of claim 26, wherein the vent housing comprises a plurality of projections, and wherein a plurality of damping orifices are formed between the plurality of projections, the plurality of damping orifices being configured to allow gas to flow therethrough and into and out of a damping chamber from the volume at least partially formed by the plenum chamber, and plurality of damping orifices being configured to resist gas exchange between the damping chamber and the volume at least partially formed by the plenum chamber to damp vibration of the moveable portion of the membrane.

29. The patient interface of claim 1, wherein the vent housing comprises a rounded surface at or proximal to an entrance to the exhaust gas flow passage to facilitate a change in direction of the vent flow of gas proximal to the entrance to the exhaust gas flow passage.

30. The patient interface of claim 1, wherein the vent housing comprises a plurality of exhaust gas orifices.

31. The patient interface of claim 30, wherein the vent housing comprises at least one diffused exhaust gas orifice and at least one undiffused exhaust gas orifice.

32. The patient interface of claim 31, wherein the at least one diffused exhaust gas orifice is located at or proximal to a first end of the vent housing and the at least one undiffused exhaust gas orifice is located between the first end of the vent housing and a second end of the vent housing.

33. The patient interface of claim 31, wherein the at least one diffused exhaust gas orifice opens in a lateral direction and the at least one undiffused exhaust gas orifice opens in at an oblique angle relative to the lateral direction partially towards the second end of the vent housing.

34. The patient interface of claim 31, comprising a diffuser member comprising a network of fibres and configured to diffuse and/or audibly muffle noise from gas that contacts the diffuser member during use.

35. The patient interface of claim 31, wherein the vent structure is configured to allow gas to flow through the at least one undiffused exhaust gas orifice if the gas is unable to flow through the at least one diffused exhaust gas orifice.

36. The patient interface of claim 35, wherein the vent structure is shaped such that the flow of gas changes direction to a greater extent to flow through the at least one undiffused exhaust gas orifice than to flow through the at least one diffused exhaust gas orifice.

37. The patient interface of claim 31, comprising an exhaust gas orifice member at least partly forming the at least one exhaust gas orifice, and the exhaust gas orifice member being configured to connect to a first housing member of the vent housing.

38. The patient interface of claim 37, wherein the at least one diffused exhaust gas orifice is positioned at or proximal to a first end of the exhaust gas orifice member and the at least one undiffused exhaust gas orifice is provided at or proximate a second end of the exhaust gas orifice member opposite the first end of the exhaust gas orifice member.

39. The patient interface of claim 37, comprising a diffuser member comprising a network of fibres and configured to be retained in the vent structure by the exhaust gas orifice member.

40. The patient interface of claim 1, wherein the moveable portion of the membrane is positioned radially outward from the membrane-facing surface, with respect to the longitudinal axis of the membrane.

41. The patient interface of claim 1, wherein the moveable portion of the membrane is configured to be constricted to move radially inwardly towards the membrane-facing surface.

42. The patient interface of claim 1, wherein the membrane-facing surface is provided on an outer surface of a first housing member of the vent housing, and the outer surface is located within the vent housing.

43. The patient interface of claim 42, wherein the first housing member comprises a shaft configured to project from a first end of the first housing member into an interior of the vent structure, and the membrane-facing surface being positioned on an outside surface of the shaft at or proximal to the second end of the first housing member.

44. The patient interface of claim 43, wherein the first housing member comprises a rounded surface on the shaft at the second end of the first housing member at or proximal to an entrance to the exhaust gas flow passage.

45. The patient interface of claim 1, wherein the exhaust gas flow passage extends contiguously around an entire circumference in the vent housing.

46. The patient interface of claim 1, further comprising a swivel elbow or a vent connector tube, wherein the outlet of the vent housing and the plenum chamber inlet port are configured to be fluidly connected by the swivel elbow or the vent connector tube.

\*  \*  \*  \*  \*